US009630996B2

(12) United States Patent
Kang et al.

(10) Patent No.: US 9,630,996 B2
(45) Date of Patent: Apr. 25, 2017

(54) ATTENUATED RECOMBINANT VESICULAR STOMATITIS VIRUSES COMPRISING MODIFIED MUTANT MATRIX PROTEINS

(71) Applicant: THE UNIVERSITY OF WESTERN ONTARIO, London (CA)

(72) Inventors: Chil-Yong Kang, London (CA); Gyoung Nyoun Kim, London (CA)

(*) Notice: Subject to any disclaimer, the term of this patent is extended or adjusted under 35 U.S.C. 154(b) by 102 days.

(21) Appl. No.: 14/368,102

(22) PCT Filed: Dec. 21, 2012

(86) PCT No.: PCT/CA2012/001185
§ 371 (c)(1),
(2) Date: Jun. 23, 2014

(87) PCT Pub. No.: WO2013/091080
PCT Pub. Date: Jun. 27, 2013

(65) Prior Publication Data
US 2014/0370043 A1    Dec. 18, 2014

Related U.S. Application Data

(60) Provisional application No. 61/579,902, filed on Dec. 23, 2011.

(51) Int. Cl.
*A61K 39/205* (2006.01)
*A61K 39/00* (2006.01)
*C07K 14/145* (2006.01)
*C12N 7/04* (2006.01)
*C07K 14/005* (2006.01)
*A61K 39/12* (2006.01)
*C12N 7/00* (2006.01)

(52) U.S. Cl.
CPC .......... *C07K 14/005* (2013.01); *A61K 39/12* (2013.01); *A61K 39/205* (2013.01); *C12N 7/00* (2013.01); *A61K 2039/5252* (2013.01); *A61K 2039/5254* (2013.01); *A61K 2039/5256* (2013.01); *A61K 2039/545* (2013.01); *C12N 2740/16134* (2013.01); *C12N 2740/16234* (2013.01); *C12N 2740/16334* (2013.01); *C12N 2760/20222* (2013.01); *C12N 2760/20234* (2013.01); *C12N 2760/20243* (2013.01); *C12N 2760/20262* (2013.01)

(58) Field of Classification Search
CPC ................ C07K 14/005; C12N 7/00; C12N 2760/20243; C12N 2760/20234; C12N 2760/20262; A61K 39/205; A61K 2039/5256; A61K 2039/5254
See application file for complete search history.

(56) References Cited

U.S. PATENT DOCUMENTS 6,174,530 B1    1/2001   Rose et al.
6,184,344 B1    2/2001   Kent et al.
2010/0272687 A1  10/2010  Bell et al.

OTHER PUBLICATIONS

Kim, G. N. and Kang, C. Y, Matrix Protein of VSV New Jersey serotype containing methionine to arginine substitutions at positions 48 and 51 allows near-normal host cell gene expression, Virology, 2007, p. 41-53, 357, Elsevier Inc.
Fields, B. N., and Hawkins, K, Human Infection with the Virus of Vesicular Stomatitis During an Epizootic, N. Engl J Med, 1967, p. 989-994, vol. 277:19.
Johnson, K. M. et al, Clinical and Serological Response to Laboratory-Acquired Human Infection by Indiana Type Vesicular Stomatitis Virus, Am J Trop Med Hyg, 1966, p. 244-246, vol. 15 No. 3.
Rabinowitz, S. et al, Comparative neurovirulence of selected vesicular stomatits virus temperature-sensitive mutants of complementation groups II and III, Infection and Immunity, 1981, p. 120-125, vol. 33(1).
Flood, E. et al, Role of M Protein Aggregation in Defective Assembly of Temperature-Sensitive M Protein Mutants of Vesicular Somatitis Virus, Virology, 2000, p. 520-533, vol. 278.
Lyles, D. et al, Complementation of M Gene Mutants of Vesicular Stomatitis Virus by Plasmid-Derived M Protein Converts Spherical Extracellular Particles into Native Bullet Shapes, Virology, 1995, p. 76-87, vol. 217.
Morita, K. et al, Phenotypic revertants of temperature-sensitive M protein mutants of vesicular stomatitis virus: sequence analysis and functional characterization, J. Virol, 1984, p. 256-263, vol. 61(2).
Li, Y et al, Site-specific mutations in vectors that express antigenic and temperature-sensitive phenotypes of the M gene of vesicular stomatitis virus, J. Virol, 1988, p. 3729-3737, vol. 62(10).
Kahn, J et al, Replication-Competent or Attenuated, Nonpropagating Vesicular Stomatitis Viruses Expressing Respiratory Syncytial Virus (RSV) Antigens Protect Mice against RSV Challenge, J. Virol, 2001, p. 11079-11087, vol. 75 (22).

(Continued)

*Primary Examiner* — Jeffrey Parkin
(74) *Attorney, Agent, or Firm* — Eduardo Krupnik; Miller Thomson LLP

(57) ABSTRACT

The present invention relates to vesicular stomatitis virus (VSV) matrix (M) protein mutants. One mutant M protein includes a glycine changed to a glutamic acid at position (21), a leucine changed to a phenylalanine at position (111) and a methionine changed to an arginine at position (51). Another M protein mutant includes a glycine changed to a glutamic acid at position (22) and a methionine changed to an arginine at positions (48) and (51). Yet another VSV M protein mutant includes a glycine changed to a glutamic acid at position (22), a leucine changed to a phenylalanine at position (110) and a methionine changed to an arginine at positions (48) and (51). The present invention is directed also to recombinant VSVs (rVSV) having these M mutants and to vaccines based on the rVSV having the M mutants of the present invention. These new rVSVs having the mutant M were significantly attenuated and lost virulence, including neurovirulence, and are capable of inducing an immune responses against an antigen of interest. In addition, a rVSV serotype Indiana having the first described M mutant is capable of efficient replication at 31° C., and of poor replication or incapable of replication at about 37° C. or higher.

14 Claims, 35 Drawing Sheets

(56) References Cited

OTHER PUBLICATIONS

Schwartz, J et al, Vesicular Stomatitis Virus Vectors Expressing avian influenza H5 HA induce cross-neutralizing antibodies and long-term protection, Virology, 2007 p. 166-173, vol. 366.
IUPAC-IUB Commission on Biochemical Nomenclature Symbols for Amino-Acid Derivatives and Peptides Recommendations, Biochemistry, 1972, p. 1726-1732, vol. 11(9).
Muir, T. and Kent, S., The Chemical synthesis of proteins, Biotech, 1993, p. 420-427, vol. 4.
Wlodawer, A et al, Conserved folding in retroviral proteases: crystal structure of a synthetic HIV-1 protease, Science, Aug. 11, 1989, p. 616-621, vol. 245(4918).
Huang, L. et al, Sequence Specific H NMR Assignments, Secondary Structure, and Location of the Calcium Binding Site in the First Epidermal Growth Factor Like Domain of Blood Coagulation Factor IX, Biochemistry, 1991, p. 7402-7409, vol. 30, American Chemical Society.
Schnolzer, M et al, In situ neutralization in boc-chemistry solid phase peptide synthesis, Int J. Pept Prot Res, 1992, p. 180-193, vol. 40.
Rajarathnam, K. et al, Neutrophil Activation by Monomeric Interleukin-8, Science, 1994, p. 90-92, vol. 264(5155).
Wallace, C. et al, Functional role of heme ligation in cytochrome c, J. Biol. Chem., 1992, p. 3852-3861, vol. 267(6).
Abrahmsen, L. et al, Engineering Subtilisin and Its Substrates for Efficient Ligation of Peptide Bonds in Aqueous Solution, Biochemistry, 1991, p. 4151-4159, vol. 30.
Chang, T. et al, Subtiligase: A tool for semisynthesis of proteins, Proc. Natl Acad. Sci. USA, Aug. 1994, p. 12544-12548, vol. 91.
Schnolzer, M. et al, Constructing Proteins by Dovetailing Unprotested Synthetic Peptides: Backbone-Engineered HIV Protease, Science, 1992, p. 221-225, vol. 256(5054).
Akaji, K. et al, Studies on Peptides, CXXVII. Synthesis of a Tripentacontapeptide with Epidermal Growth Factor Activity, Chem. Pharm. Bull., 1985, p. 184-201, vol. 33(1).
Li, Y. et al, Effects of inefficient cleavage of the signal sequence of HIV-1 gp120 on its association with calnexin, folding, and intracellular transport, PNAS, 1996, p. 9606-9611, vol. 93.
Wu, K. et al, Expression and processing of human immunodeficiency virus type 1 gp160 using the vesicular stomatitis virus New Jersey serotype vector system, Journal of General Viral, 2009, p. 1135-1140, vol. 90.
Blanchard, E. et al, Hepatitis C Virus-Like Particle Morphogenesis, J. Virol, 2002, p. 4073-4079, vol. 76(8).
Steinmann, E. et al, Hepatitis C Virus p7 Protein is Crucial for Assembly and Release of Infectious Virions, PLoS Pathogens, 2007, p. 962-972, vol. 3(7).
Diepolder, H. et al, Immunodominant CD4+ T-cell epitope within nonstructural protein 3 in acute hepatitis C virus infection, J. Virol, 1997, p. 6011-6019, vol. 71(8).
Lamonaca, V. et al, Conserved Hepatitis C Virus Sequences are highly immunogenic for CD4+ T Cells: Implications for Vaccine Development, Hepatology, 1999, p. 1088-1098, vol. 30(4).
Shoukry, N. et al, Conserved Hierarchy of Helper T Cell Responses in a Chimpanzee during Primary and Secondary Hepatitis C Virus Infections, J. Immunol, 2004, p. 482-492, vol. 172.
Satoh, S. et al, The N-terminal region of hepatitis C virus nonstructural protein 3 (NS3) is essential for stable complex formation with NS4A, J. Virol., 1995, p. 4255-4260, vol. 69(7).
Failla, C. et al, An amino-terminal domain of the hepatitis C virus NS3 protease is essential for interaction with NS4A, J. Virol, 1995, p. 1769-1777, vol. 69(3).
Shirota, Y. et al, Hepatitis C Virus (HCV) NS5A Binds RNA-dependent RNA Polymerase (RdRP) NS5B and Modulates RNA-dependent RNA Polymerase Activity, J. Biol. Chem, 2002, p. 11149-11155, vol. 277.
Shimakami, T. et al, Effect of Interaction between Hepatitis C Virus NS5A and NS5B on Hepatitis C Virus RNA Replication with the Hepatitis C Virus Replicon, J. Virol, 2004, p. 2738-2748, vol. 78(6).
Behrens, S. et al, Identification and properties of the RNA-dependent RNA polymerase of hepatitis C virus, EMBO Journal, 1996, p. 12-22, vol. 15(1).
Yamashita, T. et al, RNA-dependent RNA Polymerase Activity of the Soluble Recombinant Hepatitis C virus NS5B Protein Truncated at the C-terminal Region, J. Biol. Chem., 1998, p. 15479-15486, vol. 273.
Hagedorn, C. et al, Hepatitis C Virus RNA-Dependent RNA Polymerase (NS5B Polymerase), Curr. Top. Microbial. Immunol., 2000 p. 225-260 vol. 242.
Gopalakrishna, Y et al, Sequence alternations in temperature-sensitive M-protein mutants of vesicular stomatitis virus, J. Virology, 1985, p. 665-659, vol. 56(3).

pVSV_NJ with Mutations in The M Gene

[pT7] — N — P — M — G — L — [HDV T7δ]

Pac I  Not I     Pac I, Fse I, Pme I, Xho I, Mlu I, Pac I, Kpn I

| Construct | Label |
|---|---|
| (wild type) | WT |
| M48R+M51R | M48R+M51R |
| G22E | G22E |
| G22EM48R+M51R | G22E/M48R+M51R (GM) |
| G22E  L110F | G22E/L110F (GL) |
| G22EM48R+M51R L110F | G22E/L110F/M48R+M51R (GLM) | pT7; Bacteriophage T7 transcriptional promoter, HDV; Ribozyme from hepatitis D virus, T7δ; Transcriptional terminator

FIGURE 2

Recovery of Recombinant VSV By Reverse Genetics pVSV: Full length cDNA clone of VSV genome, BHK-T7: BHK21 cells constitutive expressing T7 DNA dependent RNA polymerase, pN: A plasmid expressing VSV nucleocapsid protein, pP: A plasmid expressing VSV phosphoprotein, pL: A plasmid expressing VSV large protein, IRES: Internal ribosomal entry site

FIGURE 3

Mutations in the M Gene of rVSV$_{NJ}$, G22E and L110F Do Not Reduce the Burst Size of the rVSV$_{NJ}$ at 37 °C

| rVSV$_{NJ}$ | Burst Size (PFU/ml) | |
|---|---|---|
| | 31°C | 37°C |
| WT | 1.53X10$^9$ | 3.03X10$^9$ |
| M48R+M51R | 2.05X10$^8$ | 4.23X10$^8$ |
| G22E | 1.43X10$^9$ | 1.9X10$^9$ |
| G22E/M48R+M51R | 5.78X10$^8$ | 3.48X10$^8$ |
| G22E/L110F | 1.20X10$^9$ | 1.85X10$^9$ |
| G22E/L110F/M48R+M51R | 3.15X10$^8$ | 2.98X10$^8$ |

FIGURE 5

Assembly Defectiveness at Semi-Permissive Temperature by L111F Mutation in The M Gene of rVSV$_{Ind}$ Does not Affect the Expression of VSV proteins A) rVSV$_{Ind}$ 1. WT 2. M51R 3. G21E 4. G21E/M51R (GM)
5. G21E/L111F (GL) 6. G21E/M51R/L111F (GLM)

B) rVSV$_{NJ}$

1. WT 2. M48R+M51R 3. G22E
4. G22E/M48R+M51R (GM) 5. G22E/L110F (GL)
6. G22E/L110F/M48R+M51R (GLM)

Gag expression in BHK cells infected with rVSV$_{NJ}$(GM)-HIV-1 Gag

A: NJ(GM)-HIV-1 Gag A
B: NJ(GM)-HIV-1 Gag B
C: NJ(GM)-HIV-1 Gag C
E: NJ(GM)-HIV-1 Gag En
R: NJ(GM)-HIV-1 Gag RT
V: NJ(GM)

Generation of rVSV$_{Ind}$(GLM) and rVSV$_{NJ}$(GM) Expressing HCV Non-Structural Proteins pT7 — N — P — M — G — [Mlu I] — L — HDV T7δ rVSV-NS3: NS3 rVSV-NS34AB: NS3 | NS4A | NS4B rVSV-NS5A: NS5A rVSV-NS5B: NS5B rVSV-NS5AB: NS5A | NS5B

HCV Genes

1 — C | E1 | E2 | P7 | NS2 | NS3 | NS4A | NS4B | NS5A | NS5B — 3000

C; Core, E1; Glycoprotein E1, E2; Glycoprotein E2, P7, viroporin, NS; Nonstructural protein

ATTENUATED RECOMBINANT VESICULAR STOMATITIS VIRUSES COMPRISING MODIFIED MUTANT MATRIX PROTEINS

CROSS REFERENCE TO RELATED APPLICATIONS

This application is a national stage application under 35 U.S.C. 371 of international Application No. PCT/CA2012/001185, filed Dec. 21, 2012, which in turn claims the benefit under 35 U.S.C. 119(e) of U.S. Provisional Ser. No. 61/579,902; filed Dec. 23, 2011, the contents of which are hereby incorporated by reference into the present disclosure.

REFERENCE TO A "SEQUENCE LISTING" A TABLE, OR A COMPUTER PROGRAM LISTING APPENDIX SUBMITTED ON A COMPACT DISK

A paper copy of the Sequence Listing and a Sequence Listing in computer readable form in .txt format titled "118494_106SequenceListing.txt", which was submitted online on Jun. 23, 2014, and is 22.1 KB in size are hereby incorporated by reference. Applicants assert that the paper copy of the Sequence Listing is identical to the Sequence Listing in computer readable form.

FIELD OF THE INVENTION

The present invention relates, in general, to biotechnology and immunology. In particular, the present invention relates to novel matrix (M) proteins of vesicular stomatitis virus (VSV), to attenuated recombinant VSVs expressing the novel M proteins and to VSV based prime-boost vaccines that induce long-lasting humoral, cell-mediated and mucosal immune responses against foreign antigens expressed by the recombinant VSV carrying foreign genes.

BACKGROUND OF THE INVENTION

Vesicular stomatitis virus (VSV) is a negative stranded RNA virus which infects most mammalian cells and expresses viral proteins up to 60% of total proteins in infected cells [Kim, G. N., and C. Y. Kang. Virology 357:41, 2007]. In nature VSV infects pigs, cattle, and horses, and causes vesicular disease around the mouth and foot. Although human infection by VSV has been reported, VSV does not cause any serious symptoms in humans [Fields, B. N., and K. Hawkins. N Engl J Med 277:989, 1967; Johnson, K. M. et al. Am J Trop Med Hyg 15:244, 1966].

VSV encodes five proteins, nucleocapsid protein (N), phosphoprotein (P), matrix protein (M), surface glycoprotein (G), and RNA dependent RNA polymerase (L). The N, P, and L proteins of VSV are required for synthesis of positive sense and negative sense genomic RNAs and mRNA, which are necessary for the synthesis of VSV proteins.

Blocking the host cellular protein synthesis by VSV matrix (M) protein induces cell death. Changing a methionine residue at position 51 of the M protein to arginine (M51R) in the vesicular stomatitis virus Indiana serotype ($VSV_{Ind}$), and changing methionines at position 48 (Met48) and 51 (Met51) to Arg in the vesicular stomatitis virus New Jersey serotype ($VSV_{NJ}$) M gene could negate this function of VSV M protein (Kim, G. and Kang, C., Virology, 357: 41-53, 2007). While the VSVs with these Met to Arg mutations in the M protein have significantly reduced cytopathic effects, they still replicate and produce progeny viruses in the cell and in the infected animal. One of the temperature sensitive (ts) M gene mutants of $VSV_{Ind}$ Orsay strain, tsO23 has shown limited replication in a mouse glial cell line at 37° C. and 39° C. (Rabinowitz, S. et al. Infection and Immunity 33:120-125, 1981). It has been demonstrated that the temperature sensitivity of tsO23 was the result of the improper or lack of the initiation of the viral assembly with the characteristic bullet shaped structure at 39° C. (Flood, E. et al. Virology 278:520-533, 2000; Lyles, D. et al. Virology, 217:76-87, 1996). In addition, the tsO23 lost its neurovirulence in mice even after direct inoculation into the brain (Rabinowitz, S. et al. Infection and Immunity, 33:120-125, 1981).

There are three amino acid differences between wild type M of VSV Orsay strain and M of tsO23, which are glycin (G) to glutamic acid (E) at 21st amino acid (G21E), leucine (L) to phenylalanine (F) at 111th amino acid (L111F), and histidine (H) to tyrosine (Y) at 227th amino acids (H227Y) (Morita, K. et al. J. Virol. 61:256-263, 1987). The single amino acid reversion at F111 to L in revertants implicated that the F111 appears to play a major role in the temperature sensitivity of the tsO23. However, the other two mutations may also have some role because the single reversion from the F to L at 111th position did not recover the virus completely to its wild type phenotype (Morita, K. et al. J. Virol. 61:256-263, 1987; Li, Y. et al. J. Virol. 62:3729-3737, 1988).

Currently, research groups have developed replication competent, assembly defective VSV having a G glycoprotein (G) gene deleted (ΔG) or both G and M genes deleted (ΔMG) as safer vaccine vectors (Kahn, J. et al. J. Virol. 75:11079-11087, 2001; Schwartz, J. et al., Virology 366: 166-73, 2007). However, having the G gene deleted or M and G gene deleted, the VSV vector requires the supply of G or both M and G proteins in trans for the production of the assembly-defective VSV. In order to reduce the cost of producing vaccines, it is necessary to generate a system, which can produce the viral vaccine vectors that can replicate in high titre. Therefore, what is needed is a full-length VSV vector system, which has lost its virulence (avirulent) and still can replicate to a high titer in vitro at 31° C. cannot assemble properly at non-permissible temperatures, and induce good immune responses against the gene of interest that it expresses.

Further and other objects of the invention will be realized from the following Summary of the Invention, the Discussion of the Invention and the embodiments and Examples thereof.

SUMMARY OF THE INVENTION

The inventors have generated new matrix (M) protein mutants of vesicular stomatitis virus (VSV), including VSV Indiana serotype ($VSV_{Ind}$) and VSV New Jersey serotype ($VSV_{NJ}$). These new VSVs having the mutant M proteins are essentially non-cytolytic, significantly attenuated and avirulent, including neurovirulence (safer). Furthermore, these new VSVs having the mutant M proteins are capable of inducing immune responses against an antigen or epitope of interest. The immune response may be humoral, cellular and mucosal immune responses. In addition, the $VSV_{Ind}$ having the M mutant can assemble and be released from the infected cells normally at 31° C., but they can not assemble properly at 37° C. or higher and the release of the viruses from infected cells is reduced significantly by about 1000 or 10,000 folds compared to that of wild type $VSV_{Ind}$.

As such, in one embodiment, the present application relates to a modified matrix (M) protein of a vesicular stomatitis virus (VSV). In one embodiment, the modified M protein comprises an amino acid sequence selected from the group consisting of: (i) SEQ ID NO: 3 including at least the following substitutions: G21E/L111F/M51R, and (ii) SEQ ID NO: 8 including at least the following substitutions: G22E/M48R+M51R. In one aspect of the present invention, the modified M protein of the present invention comprises the amino acid sequence of SEQ ID NO:8 including at least the following substitutions: G22E/L110F/M48+M51R.

In another embodiment of the modified M protein of the present invention, the modified M protein comprises an amino acid sequence selected from the group consisting of: SEQ ID NO:4, SEQ ID NO:9 and SEQ ID NO:10.

In another embodiment, the present application provides for a recombinant VSV (rVSV). In one embodiment, the rVSV comprises a modified matrix (M) protein, the modified M protein comprising an amino acid sequence selected from the group consisting of: (i) SEQ ID NO: 3 including at least the following substitutions: G21E/L111F/M51R; and (ii) SEQ ID NO: 8 including at least the following substitutions: G22E/M48R+M51R.

In one embodiment of the present invention, the rVSV is a chimeric rVSV that expresses a protein of a foreign pathogen, and wherein said chimeric rVSV is capable of inducing an immune response to said protein.

In another embodiment of the rVSV of the present invention, the pathogen is a viral, fungal, bacterial or parasitic pathogen.

In another embodiment of the rVSV of the present invention, the rVSV is essentially non-cytolytic and avirulent.

In one embodiment of the present invention, the rVSV is a recombinant vesicular stomatitis virus Indiana serotype (rVSV$_{Ind}$), and the modified M protein comprises the amino acid sequence of SEQ ID NO: 3 including at least the following substitution: G21E/L111F/M51R.

In one embodiment of the rVSV$_{Ind}$ of the present invention, the modified M protein comprises the amino acid sequence of SEQ ID NO: 4.

In another embodiment of the rVSV$_{Ind}$ of the present invention, the modified M protein is encoded by a gene comprising a nucleotide sequence of SEQ ID NO: 2.

In another embodiment of the rVSV of the present invention, the rVSV$_{Ind}$ of any of the previous embodiments is capable of producing VSV$_{Ind}$ particles at permissible temperatures and incapable of producing the particles at non-permissible temperatures.

In another embodiment of the present invention, the rVSV is a recombinant vesicular stomatitis virus New Jersey serotype (rVSV$_{NJ}$), and the modified M protein comprises the amino acid sequence of SEQ ID NO: 8 including at least the following substitutions: G22E/M48R+M51R.

In one embodiment of the rVSV$_{NJ}$ of the present invention, the modified M protein is encoded by a gene having a nucleotide sequence of SEQ ID NO: 6.

In another embodiment of the rVSV$_{NJ}$ of the present invention, the modified M protein comprises the amino acid sequence SEQ ID NO: 9.

In another embodiment of the rVSV$_{NJ}$ of the present invention the modified M protein includes the following substitutions: G22E/L110F/M48R+M51R.

In another embodiment of the rVSV$_{NJ}$ of the present invention, the modified M protein is encoded by a gene having a nucleotide sequence of SEQ ID NO: 7.

In another embodiment of the rVSV$_{NJ}$ of the present invention, the modified M protein comprises the amino acid sequence SEQ ID NO: 10.

In one embodiment, the present invention provides for a vaccine. In one embodiment, the vaccine of the present invention comprises an effective amount of one or more attenuated rVSVs, the one or more attenuated rVSVs including a modified matrix (M) protein, the modified M protein comprising an amino acid sequence selected from the group consisting of: (1) SEQ ID NO: 3 including at least the following substitutions: G21E/L111F/M51R, and (ii) SEQ ID NO: 8 including at least the following substitutions: G22E/M48R+M51R.

In one embodiment of the vaccine of the present invention, the rVSV is a recombinant vesicular stomatitis virus Indiana serotype (rVSV$_{Ind}$), and the modified M protein comprises the amino acid sequence of SEQ ID NO: 3 including at least the following substitution: G21E/L111F/M51R.

In another embodiment of the vaccine of the present invention, the modified M protein of the rVSV$_{Ind}$ comprises the amino acid sequence of SEQ ID NO: 4.

In another embodiment of the vaccine of the present invention, the modified M protein of the rVSV$_{Ind}$ is encoded by a gene comprising a nucleotide sequence of SEQ ID NO: 2.

In another embodiment of the vaccine of the present invention, the rVSV$_{Ind}$ is capable of producing VSV$_{Ind}$ particles at permissible temperatures and incapable of producing the particles at non-permissible temperatures.

In one embodiment of the vaccine of the previous invention, the rVSV is a recombinant vesicular stomatitis virus New Jersey serotype (rVSV$_{NJ}$), and the modified M protein comprises the amino acid sequence of SEQ ID NO: 8 including at least the following substitutions: G22E/M48R+M51R.

In one embodiment of the vaccine of the present invention, the rVSV is rVSV$_{NJ}$ and the modified M protein is encoded by a gene having a nucleotide sequence of SEQ ID NO: 6.

In another embodiment of the vaccine of the present invention, the rVSV is rVSV$_{NJ}$ and the modified M protein comprises the amino acid sequence SEQ ID NO: 9.

In another embodiment of the vaccine of the present invention, the rVSV is rVSV$_{NJ}$ and the modified M protein includes the following substitutions: G22E/L110F/M48R+M51R.

In another embodiment of the vaccine of the present invention, the rVSV is rVSV$_{NJ}$ and the modified M protein is encoded by a gene having a nucleotide sequence of SEQ ID NO: 7.

In another embodiment of the vaccine of the present invention, the rVSV is rVSV$_{NJ}$ and the modified M protein comprises the amino acid sequence SEQ ID NO: 10.

In another embodiment of the vaccine of the present invention, the rVSV according to any of the previous embodiments is a chimeric rVSV that expresses a protein of a foreign pathogen, and the chimeric rVSV is capable of inducing an immune response to said protein.

In another embodiment of the vaccine of the present invention, the rVSV comprises a mixture of attenuated chimeric rVSVs, wherein at least two chimeric rVSVs in the mixture express a different protein of the foreign pathogen.

In another embodiment of the vaccine of the present invention, the pathogen is a viral, a fungal, a bacterial or a parasitic pathogen.

In another embodiment of the vaccine of the present invention, the pathogen is a lentivirus.

In another embodiment of the vaccine of the present invention, the lentivirus is a HIV and the epitope is a HIV protein.

In another embodiment of the present invention, the pathogen is HCV and the epitope is a HCV protein.

In one embodiment of the present invention, the vaccine of any one of the previous embodiments is capable of inducing a humoral, cellular and mucosal immune response.

In another embodiment of the present invention, the vaccine according to any one of the previous embodiments further includes an adjuvant.

In one embodiment, the present invention provides for a method of inducing an immune response in a subject. In one embodiment of the present invention, the method comprises administering to the subject: (a) an effective amount of a vaccine comprising an attenuated rVSV of one serotype having a first modified M protein, the first modified M protein comprising the amino acid sequence of SEQ ID NO: 3 including at least the following substitutions: G21E/L111F/M51R; and (b) an effective amount of another vaccine comprising an attenuated rVSV of another serotype having a second modified M protein, the second modified M protein comprising the amino acid sequence of SEQ ID NO: 8 including at least the following substitutions: G22E/M48R+M51R. In one aspect of the present invention, the second modified M protein comprises the amino acid sequence of SEQ ID NO:8 including at least the following substitutions: G22E/L110F/M48R+M51R In one embodiment of the method of the present invention, (a) is administered to the subject before (b) is administered to the patient.

In another embodiment of the method of the present invention, (b) is administered to the subject more than one time over the course of inducing.

In another embodiment of the method of the present invention, (a) is administered to the subject and (b) is administered to the subject at about weeks three, eight and sixteen post-administration of (a).

In another embodiment of the method of the present invention, (b) is administered to the subject before (a) is administered to the subject.

In another embodiment of the method of the present invention, (a) is administered to the subject more than one time over the course of inducing.

In another embodiment of the method of the present invention, (b) is administered to the subject and (a) is administered to the subject at about weeks three, eight and sixteen post-administration of (b).

In another embodiment of the method of the present invention, the rVSV of vaccine (a) and rVSV of vaccine (b) are chimeric rVSVs that express a protein of a foreign pathogen, and wherein the two rVSVs are capable of inducing an immune response to the protein.

In another embodiment of the method of the present invention, the pathogen is a viral, a fungal, a bacterial or a parasitic pathogen.

In another embodiment of the method of the present invention, the pathogen is a lentivirus.

In another embodiment of the method of the present invention, the lentivirus is a HIV and the protein is a HIV protein.

In another embodiment of the method of the present invention, the rVSV of one serotype and the rVSV of the other serotype include a surface glycoprotein (G) gene and a RNA dependent RNA polymerase (L) gene, and wherein a gene for expressing the HIV protein is a HIV gene inserted in between the G gene and the L gene.

In another embodiment of the method of the present invention, the HIV gene is selected from the group of HIV genes consisting of gag, env and pol.

In another embodiment of the method of the present invention, the pathogen is HCV and the protein is a HCV protein.

In another embodiment of the method of the present invention, the rVSV of one serotype and the rVSV of the other serotype include a surface glycoprotein (G) gene and a RNA dependent RNA polymerase (L) gene, and wherein a gene for expressing the HCV protein is inserted in between the G gene and the L gene of the rVSV.

In another embodiment of the method of the present invention, vaccine (a) and vaccine (b) comprise a mixture of attenuated chimeric rVSVs, wherein at least two of the attenuated chimeric rVSVs in the mixture express a different protein of the pathogen.

In another embodiment of the method of the present invention, each one of the two vaccines (a) and (b) induces humoral, cellular and mucosal immune responses.

In another embodiment of the method of the present invention, the serotype of the rVSV of vaccine (a) is Indiana and the serotype of the rVSV of vaccine (b) is New Jersey.

In another embodiment of the method of the present invention, each of vaccine (a) and vaccine (b) further comprises an adjuvant.

In one embodiment, the present invention provides for a prime boost combination vaccine. In one embodiment, the prime boost combination vaccine comprises: (a) an effective amount of a vaccine comprising an attenuated rVSV of one serotype having a first modified M protein comprising the amino acid sequence of SEQ ID NO:4; and (b) an effective amount of a vaccine comprising a rVSV of another serotype having a second modified M protein comprising the amino acid sequence of SEQ ID NO:9 or SEQ ID NO:10.

In one embodiment of the prime boost combination vaccine of the present invention, vaccine (a) is a priming vaccine and vaccine (b) is a booster vaccine.

In another embodiment of the prime boost combination vaccine of the present invention, vaccine (b) is a priming vaccine and vaccine (a) is a booster vaccine.

In another embodiment of the prime boost combination vaccine of the present invention, the two attenuated rVSVs are chimeric rVSVs that express a protein of a foreign pathogen, and the two chimeric rVSVs are capable of inducing an immune response to the protein.

In another embodiment of the prime boost combination vaccine of the present invention, the pathogen is a viral, a fungal, a bacterial or a parasitic pathogen.

In another embodiment of the prime boost combination vaccine of the present invention, the pathogen is a lentivirus.

In another embodiment of the prime boost combination vaccine of the present invention, the lentivirus is a HIV and the protein is a HIV protein.

In another embodiment of the prime boost combination vaccine of the present invention, the rVSV of one serotype and the rVSV of the other serotype include a surface glycoprotein (G) gene and a RNA dependent RNA polymerase (L) gene, and wherein a gene for expressing the HIV protein is inserted in between the gene and the L gene.

In another embodiment of the prime boost combination vaccine of the present invention, the HIV gene is selected from the group of HIV genes consisting of env, gag and pol.

In another embodiment of the prime boost combination vaccine of the present invention, the pathogen is HCV and the epitope is a HCV protein.

In another embodiment of the prime boost combination vaccine of the present invention, the rVSV of one serotype and the rVSV of the other serotype include a surface glycoprotein (G) gene and a RNA dependent RNA polymerase (L) gene, and wherein a gene for expressing the HCV protein is inserted in between the G gene and the L gene.

In another embodiment of the prime boost combination vaccine of the present invention, the HCV protein is a structural or a non-structural HCV protein.

In another embodiment of the prime boost combination vaccine of the present invention, each one of the two vaccines comprise a mixture of the attenuated chimeric rVSVs, and at least two of the attenuated chimeric rVSVs in the mixture have a different protein of the pathogen.

In another embodiment of the prime boost combination vaccine of the present invention, each one of the two vaccines is capable of inducing immoral, cellular and mucosal immune responses.

In another embodiment of the prime boost combination vaccine of the present invention, the serotype of vaccine (a) is Indiana and the serotype of vaccine (b) is New Jersey.

In another embodiment of the prime boost combination vaccine of the present invention, each one of vaccine (a) and vaccine (b) further comprises an adjuvant.

In one embodiment, the present invention provides for a kit comprising: (a) at least one dose of an effective amount of a vaccine comprising a rVSV$_{Ind}$ having a modified M protein comprising the amino acid sequence of SEQ ID NO:4, and (b) at least one dose of an effective amount of a vaccine comprising rVSV$_{NJ}$ having a modified M protein comprising the amino acid sequence of SEQ ID NO:9 or SEQ ID NO:10.

In one embodiment of the kit of the present invention, (a) and (b) are formulated in a pharmaceutically acceptable carrier.

In yet another embodiment, the present invention provides for an isolated peptide comprising an amino acid sequence selected from the group of amino acid sequences listed as SEQ ID NOs: 4, 9 and 10.

In one embodiment, the present invention provides for isolated nucleotide sequences for encoding the isolated peptides of SEQ ID NOs: 4, 9 and 10.

BRIEF DESCRIPTION OF THE FIGURES

Embodiments will now be described, by way of example only, with reference to the drawings, in which:

FIG. 2 illustrates gene organization of vesicular stomatitis virus (VSV), New Jersey (NJ) with mutations in the M gene.

FIG. 3 illustrates a reverse genetics system for the recovery of VSV from cDNA.

FIG. 5 is a graph representing the burst size effect of mutations M48R+M51R, G22E, G22E/M48R+M51R, G22E/L110F, G22E/L110F/M48R+M51R in the M protein of rVSV$_{NJ}$ at 31° C. and 37° C. in BHK21 cells.

FIG. 6 A) is a Western blot analysis illustrating the level of rVSV protein expression of rVSV$_{Ind}$ 1. WT, 2. M51R, 3. G21E 4. G21E/M51R 5. G21E/L111F and 6. G21E/L111F/M51R.

FIG. 6 B) is a Western blot analysis illustrating the level of rVSV protein expression of rVSV$_{NJ}$ 1. WT, 2. M48R+M51R, 3. G22E 4. G22E/M48R+M51R 5. G22E/L110F and 6. G22E/L110F/M48R+M51R.

FIG. 9 includes photographs of BHK21 cells infected with rVSV$_{NJ}$ having different mutations in the M gene (panels A, D, E, F, G, H, K, L, M and N) or wild type M gene (panels B and I), and photographs of uninfected BHK21 cells (panels C and J). Cells were incubated at 31° C. (panels A to G) or 37° C. (panels H to N).

FIG. 11 includes graphs illustrating neurovirulence studies in Swiss Webster mouse by intralateral ventricular injection: A) UV-irradiated rVSV$_{Ind}$ G21E/L111F/M51R, B) rVSV$_{Ind}$ WT, C) rVSV$_{Ind}$ M51R and D) rVSV$_{Ind}$ G21E/L111F/M51R.

FIG. 13 B) is a Western blot analysis of BHK cells infected with rVSVs expressing Gag-En and having different mutations to the M gene, and incubated at 31° C. FIG. 13 C) is a Western blot analysis of BHK cells infected with rVSVs expressing Gag-En and having different mutations to the M gene, and incubated at 37° C.

FIG. 25 illustrates a Western blot analysis of BHK21 cells infected with rVSV$_{NJ}$ G22E/M48R+M51R expressing Gag A, B, C, En, and RT and incubated at 31° C. and 37° C.

FIG. 27 illustrates a Western blot analysis of BHK21 cells infected with rVSV$_{Ind}$ G21E/L111F/M51R or rVSV$_{NJ}$ G22E/M48R+M51R expressing HIV-1 gp160mss gene.

FIG. 32 illustrates Western blot analyses of the expression of HCV Core (panel A), E1 (panel B), E2 (panel C), and NS4B (panel D) proteins from the rVSV$_{Ind}$(GLM), rVSV$_{NJ}$ (GM), rVSV$_{NJ}$(GLM).

FIG. 33 depicts the HCV non-structural protein genes cloned into rVSV$_{Ind}$(GLM), rVSV$_{NJ}$(GM), and rVSV$_{NJ}$ (GLM).

FIG. 34 Western blot analyses of the expression of HCV NS3 at 37° C. and 31° C. (panel A), NS5A at 37° C. (panel B), and NS5B at 37° C. and 31° C. (panel C) from the rVSV$_{Ind}$(GLM).

FIG. 35 demonstrates the expression of HCV NS3, NS4B, NS5A, and NS5B from rVSV$_{NJ}$(GM) at 37° C. (panel A) and the expression of HCV NS5AB at 37° C. (panel B). The protein expression was detected by Western blot analysis.

DETAILED DESCRIPTION OF THE INVENTION

Overview

Figure 1:
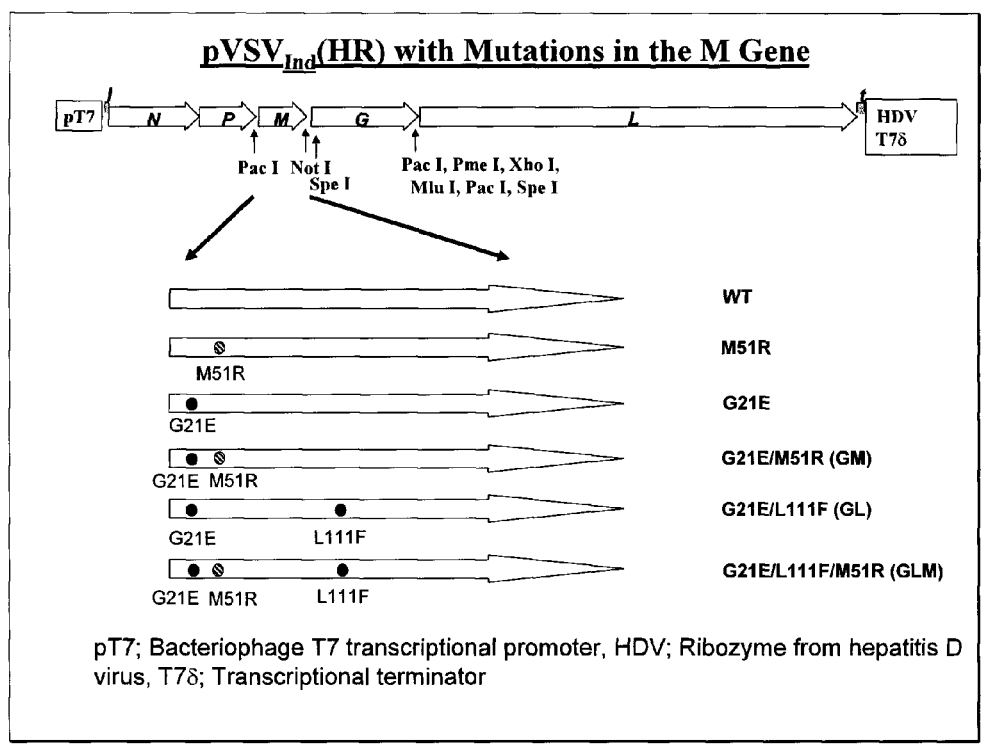
FIG. 1 illustrates gene organization of the vesicular stomatitis virus (VSV), Indiana (Ind) serotype with mutations in the M gene.

Unless defined otherwise, all technical and scientific terms used herein have the same meaning as commonly understood by one of ordinary skill in the art to which this invention belongs. Also, unless indicated otherwise, except within the claims, the use of "or" includes "and" and vice versa. Non-limiting terms are not to be construed as limiting unless expressly stated or the context clearly indicates otherwise (for example "including", "having" and "comprising" typically indicate "including without limitation"). Singular forms including in the claims such as "a", "an" and "the" include the plural reference unless expressly stated otherwise. "Consisting essentially of" means any recited elements are necessarily included, elements that would materially affect the basic and novel characteristics of the listed elements are excluded, and other elements may optionally be included. "Consisting of" means that all elements other than those listed are excluded. Embodiments defined by each of these terms are within the scope of this invention.

All numerical designations, e.g., dimensions and weight, including ranges, are approximations that typically may be varied (+) or (−) by increments of 0.1, 1.0, or 10.0, as appropriate. All numerical designations may be understood as preceded by the term "about".

The term "administering" includes any method of delivery of a compound of the present invention, including a pharmaceutical composition, vaccine or therapeutic agent, into a subject's system or to a particular region in or on a subject. The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration. "Parenteral administration" and "administered parenterally" means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intra-articular, subcapsular, subarachnoid, intraspinal and intrasternal injection and infusion.

The term "amino acid" is known in the art. In general the abbreviations used herein for designating the amino acids and the protective groups are based on recommendations of the IUPAC-IUB Commission on Biochemical Nomenclature (see Biochemistry (1972) 11:1726-1732). For the amino acids relevant to the present invention the designations are: M: methionine, R: arginine, G: glycine, E: glutamic acid, L: leucine, F: phenylalanine. In certain embodiments, the amino acids used in the application of this invention are those naturally occurring amino acids found in proteins, or the naturally occurring anabolic or catabolic products of such amino acids which contain amino and carboxyl groups. Particularly suitable amino acid side chains include side chains selected from those of the following amino acids: glycine, alanine, valine, cysteine, leucine, isoleucine, serine, threonine, methionine, glutamic acid, aspartic acid, glutamine, asparagine, lysine, arginine, proline, histidine, phenylalanine, tyrosine, and tryptophan.

The term "antibody" as used herein is intended to include whole antibodies, e.g., of any isotype (IgG, IgA, IgM, IgE, etc), including polyclonal, monoclonal, recombinant and humanized antibodies and fragments thereof which specifically recognize and are able to bind an epitope of a protein. Antibodies can be fragmented using conventional techniques and the fragments screened for utility in the same manner. Thus, the term includes segments of proteolytically-cleaved or recombinantly-prepared portions of an antibody molecule that are capable of selectively reacting with a certain protein. Nonlimiting examples of such proteolytic and/or recombinant fragments include Fab, F(ab')2, Fab', Fv, and single chain antibodies (scFv) containing a V[L] and/or V[H] domain joined by a peptide linker. The says may be covalently or non-covalently linked to form antibodies having two or more binding sites.

As used herein, the term "epitopes" refers to sites or fragments of a polypeptide or protein having antigenic or immunogenic activity in an animal, preferably in a mammal. An epitope having immunogenic activity is a site or fragment of a polypeptide or protein that elicits an immune response in an animal. An epitope having antigenic activity is a site or fragment of a polypeptide or protein to which an antibody immunospecifically binds as determined by any method well-known to one of skill in the art, for example by immunoassays.

As used herein, the term "fragment" in the context of a proteinaceous agent refers to a peptide or polypeptide comprising an amino acid sequence of at least 2 contiguous amino acid residues, at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least 80 contiguous amino acid residues, at least 90 contiguous amino acid residues, at least 100 contiguous amino acid residues, at least 125 contiguous amino acid residues, at least 150 contiguous amino acid residues, at least 175 contiguous amino acid residues, at least 200 contiguous amino acid residues, or at least 250 contiguous amino acid residues of the amino acid sequence of a peptide, polypeptide or protein. In one embodiment, a fragment of a full-length protein, retains activity of the full-length protein, e.g., immunogenic activity. In another embodiment, the fragment of the full-length protein does not retain the activity of the full-length protein, e.g., non-immunogenic activity.

As used herein, the term "fragment" in the context of a nucleic acid refers to a nucleic acid comprising an nucleic acid sequence of at least 2 contiguous nucleotides, at least 5 contiguous nucleotides, at least 10 contiguous nucleotides, at least 15 contiguous nucleotides, at least 20 contiguous nucleotides, at least 25 contiguous nucleotides, at least 30 contiguous nucleotides, at least 35 contiguous nucleotides, at least 40 contiguous nucleotides, at least 50 contiguous nucleotides, at least 60 contiguous nucleotides, at least 70 contiguous nucleotides, at least contiguous 80 nucleotides, at least 90 contiguous nucleotides, at least 100 contiguous nucleotides, at least 125 contiguous nucleotides, at least 150 contiguous nucleotides, at least 175 contiguous nucleotides, at least 200 contiguous nucleotides, at least 250 contiguous nucleotides, at least 300 contiguous nucleotides, at least 350 contiguous nucleotides, or at least 380 contiguous nucleotides of the nucleic acid sequence encoding a peptide, polypeptide or protein. In a preferred embodiment, a fragment of a nucleic acid encodes a peptide or polypeptide that retains activity of the full-length protein, e.g., immunogenic activity. In another embodiment, the fragment of the full-length protein does not retain the activity of the full-length protein, e.g., non-immunogenic activity.

The term "essentially noncytolytic" as used herein means that the recombinant vesicular stomatitis virus (rVSV) does not significantly damage or kill the cells it infects.

The term "HIV" is known to one skilled in the art to refer to Human Immunodeficiency Virus. There are two types of HIV: HIV-1 and HIV-2. There are many different strains of HIV-1. The strains of HIV-1 can be classified into three groups: the "major" group M, the "outlier" group O and the "new" group N. These three groups may represent three separate introductions of simian immunodeficiency virus into humans. Within the M-group there are at least ten subtypes or clades: e.g., clade A, B, C, D, E, F, G, H, I, J, and K. A "clade" is a group of organisms, such as a species, whose members share homologous features derived from a common ancestor. Any reference to HIV-1 in this application includes all of these strains.

The term "non-infectious" means of reduced to non-existent ability to infect.

As used herein, the terms "subject" or "patient" are used interchangeably. As used herein, the terms "subject" and "subjects" refers to either a human or non-human animal.

The term "pharmaceutical delivery device" refers to any device that may be used to administer a therapeutic agent or agents to a subject. Non-limiting examples of pharmaceutical delivery devices include hypodermic syringes, multichamber syringes, stents, catheters, transcutaneous patches, microneedles, microabraders, and implantable controlled release devices. In one embodiment, the term "pharmaceutical delivery device" refers to a dual-chambered syringe capable of mixing two compounds prior to injection.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

The terms "polynucleotide", and "nucleic acid" are used interchangeably to refer to a polymeric form of nucleotides of any length, either deoxyribonucleotides or ribonucleotides, or analogs thereof. The following are non-limiting examples of polynucleotides: coding or non-coding regions of a gene or gene fragment, loci (locus) defined from linkage analysis, exons, introns, messenger RNA (mRNA), transfer RNA (tRNA), ribosomal RNA (rRNA), ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component. The term "recombinant" polynucleotide means a polynucleotide of genomic, cDNA, semi-synthetic, or synthetic origin, which either does not occur in nature or is linked to another polynucleotide in a non-natural arrangement. An "oligonucleotide" refers to a single stranded polynucleotide having less than about 100 nucleotides, less than about, e.g., 75, 50, 25, or 10 nucleotides.

The terms "polypeptide", "peptide" and "protein" (if single chain) are used interchangeably herein to refer to polymers of amino acids. The polymer may be linear or branched, it may comprise modified amino acids, and it may be interrupted by non-amino acids. The terms also encompass an amino acid polymer that has been modified; for example, disulfide bond formation, glycosylation, lipidation, acetylation, phosphorylation, or any other manipulation, such as conjugation with a labeling component.

In certain embodiments, polypeptides of the invention may be synthesized chemically, ribosomally in a cell free system, or ribosomally within a cell. Chemical synthesis of polypeptides of the invention may be carried out using a variety of art recognized methods, including stepwise solid phase synthesis, semi-synthesis through the conformationally-assisted re-ligation of peptide fragments, enzymatic ligation of cloned or synthetic peptide segments, and chemical ligation. Native chemical ligation employs a chemoselective reaction of two unprotected peptide segments to produce a transient thioester-linked intermediate. The transient thioester-linked intermediate then spontaneously undergoes a rearrangement to provide the full length ligation product having a native peptide bond at the ligation site. Full length ligation products are chemically identical to proteins produced by cell free synthesis. Full length ligation products may be refolded and/or oxidized, as allowed, to form native disulfide-containing protein molecules (see e.g., U.S. Pat. Nos. 6,184,344 and 6,174,530; and T. W. Muir et al., Curr. Opin. Biotech. (1993): vol. 4, p 420; M. Miller, et al., Science (1989): vol. 246, p 1149; A. Wlodawer, et al., Science (1989): vol. 245, p 616; L. H. Huang, et al., Biochemistry (1991): vol. 30, p 7402; M. Schnolzer, et al., hit. J. Pept. Prot. Res. (1992): vol. 40, p 180-193; K. Rajarathnam, et al., Science (1994): vol. 264, p 90; R. E. Offord, "Chemical Approaches to Protein Engineering", in Protein Design and the Development of New therapeutics and Vaccines, J. B. Hook, G. Poste, Eds., (Plenum Press, New York, 1990) pp. 253-282; C. J. A. Wallace, et al., J. Biol. Chem. (1992): vol. 267, p 3852; L. Abrahmsen, et al., Biochemistry (1991): vol. 30, p 4151; T. K. Chang, et al., Proc. Natl. Acad. Sci. USA (1994) 91: 12544-12548; M. Schnlzer, et al., Science (1992): vol., 3256, p 221; and K. Akaji, et al., Chem. Pharm. Bull. (Tokyo) (1985) 33: 184).

"VSV" is used to refer to vesicular stomatitis virus.

"rVSV" is used to refer to a recombinant vesicular stomatitis virus.

The term "Indiana", and "IND" are used to refer to the VSV serotype Indiana ($VSV_{Ind}$).

The term "New Jersey", and "NJ" are used to refer to the VSV serotype New Jersey ($VSV_{NJ}$).

"MWT" "M(WT)" are used to refer to a wild type M protein. The nucleotide sequence of wild type M gene of the $VSV_{Ind}$ may comprise the nucleotide sequence represented by SEQ ID NO: 1. The amino acid sequence of wild type M protein of the $VSV_{Ind}$ may comprise the amino acid sequence represented by SEQ ID NO: 3. The nucleotide sequence of wild type M gene of the $VSV_{NJ}$ may comprise the nucleotide sequence represented by SEQ ID NO: 5. The amino acid sequence of wild type M protein of the $VSV_{NJ}$ may comprise the amino acid sequence represented by SEQ ID NO: 8. "M51R" is used to refer to an M(WT) in the $VSV_{Ind}$ having a methionine changed to an arginine at position 51. "G21E" is used to refer to an M(WT) in $VSV_{Ind}$ having a glycine changed to a glutamic acid at position 21. "L111F" is used to refer to an M(WT) in $VSV_{Ind}$ having a leucine changed to a phenylalanine at position 111. "G22E" is used to refer to an M(WT) in $VSV_{NJ}$ having a glycine (G) changed to glutamic acid (E) at position 22. "L110F" is used to refer to an M(WT) in $VSV_{NJ}$ having a leucine (L) changed to a phenylalanine (F) at position 110. "M48R+M51R" is used to refer to an M(WT) in $VSV_{NJ}$ having a methionine (M) changed to an arginine (R) at positions 48 and 51. "$rVSV_{Ind}$ M(G21E/L111F/M51R)" or "$rVSV_{Ind}$ (GLM)" are used to refer to a $rVSV_{Ind}$ having an M(WT) having a glycine changed to a glutamic acid at position 21, a leucine changed to a phenylalanine at position 111 and a methionine changed to an arginine at position 51. "$rVSV_{NJ}$ M(G22E/M48R+M51R)" or "$rVSV_{NJ}$ (GM)" are used to refer to $rVSV_{NJ}$ having an M(WT) having a glycine changed to a glutamic acid at position 22 and a methionine changed to an arginine at positions 48 and 51, and "$rVSV_{NJ}$ M(G22E/L110F/M48R+M51R)" or "$rVSV_{NJ}$ (GLM)" are used to refer to $rVSV_{NJ}$ having an M(WT) having a glycine changed to a glutamic acid at position 22, a leucine changed to a phenylalanine at position 110 and a methionine changed to an arginine at positions 48 and 51.

Overview

The inventors generated novel M proteins and novel attenuated rVSVs capable of producing the novel M proteins. The novel proteins of the present invention may include: M(G21E/L111F/M51R), M(G22E/M48R+M51R), and M(G22E/L110F/M48R+M51R). The novel attenuated rVSVs of the present invention may be used as protein expression and vaccine vectors and in methods for preventing or treating infections. The rVSV of the present invention may be applied to make vaccines for the infectious diseases of human and other animals to induce cellular and humoral immune responses.

Isolated Proteins and M Proteins

In one embodiment, the present invention relates to isolated proteins and to nucleotide sequences that encode the isolated proteins. As such, in one embodiment the present invention relates to an isolated peptide comprising an amino acid sequence selected from amino acid sequences listed as SEQ ID NOs: 4, 9 and 10. In another embodiment, the present invention relates to isolated nucleotide sequences comprising a nucleotide sequence selected from the polynucleotides listed as SEQ ID NOs: 2, 6 and 7.

In one embodiment, the present invention relates to novel VSV M proteins having at least one of the following substitutions: M(G21E/L111F/M51R), M(G22E/M48R+M51R), and M(G22E/L110F/M48R+M51R). In one aspect the present invention relates to a VSV M protein comprising an amino acid sequence selected from the amino acid sequences listed as SEQ 113 NOs: 4, 9 and 10. In another embodiment the present invention relates to nucleotide sequences which encode for the novel VSV M proteins of the present invention. The nucleotide sequences may be selected from the group of sequences listed as SEQ ID NOs: 2, 6 and 7.

Methods of Preventing or Treating an Infection

Provided are methods of inducing an immune response, preventing or treating infections. In one embodiment, the methods may include administering to a subject: (a) an effective amount of a vaccine comprising an attenuated rVSV of one serotype having (i) a first modified M protein, the first modified M protein comprising the amino acid sequence of SEQ ID NO: 3 including at least the following substitutions: G21E/L111F/M51R, and (ii) an epitope of the pathogen; and (b) an effective amount of another vaccine comprising an attenuated rVSV of another serotype having: (i) a second modified M protein, the second modified M protein comprising the amino acid sequence of SEQ ID NO: 8 including at least the following substitutions: G22E/M48R+M51R, and (ii) the epitope of the pathogen. In embodiments of the present invention, the methods may include administering to a subject (a) an effective amount of $rVSV_{Ind}$ M(G21E/L111F/M51R), and (b) an effective amount of either a $rVSV_{NJ}$ M(G22E/M48R+M51R) or $rVSV_{NJ}$ M(G22E/L110F/M48R+M51R) in a prime-boost immunization modality.

The term "effective amount" as used herein means an amount effective and at dosages and for periods of time necessary to achieve the desired result.

In certain embodiments, (a) is administered to the subject before (b) is administered to the subject.

In certain embodiments, (b) is administered to the subject more than one time over the course of treating or preventing.

In certain embodiments, (a) is administered to the subject in need thereof and (b) is administered to the subject in need thereof at about weeks three, eight and sixteen post-administration of (a).

In certain embodiments, (b) is administered to the subject before (a) is administered to the subject.

In certain embodiments, (a) is administered to the subject more than one time over the course of treating or preventing.

In certain embodiments, (b) is administered to the subject in need thereof and (a) is administered to the subject in need thereof at about weeks three, eight and sixteen post-administration of (b).

Recombinant Virus

In certain embodiments, present invention relates to a recombinant vesicular stomatitis virus (rVSV) which may be a full length VSV, essentially non-cytolytic, avirulent, capable of inducing an immune response in a subject, capable of reproducing virus particles to a high tire at permissive temperatures, reproducing virus particles to a low titre at semi-permissive temperatures and which may be incapable of producing virus at non-permissive temperatures, and that can express an epitope of a foreign pathogen. The rVSV of the present invention may be capable of inducing humoral, cellular and mucosal immune responses.

In one embodiment, the present invention relates to $rVSV_{Ind}$ and $rVSV_{NJ}$. The $rVSV_{Ind}$ may be a full length, essentially noncytolytic $rVSV_{Ind}$ M(G21E/L111F/M51R) capable of producing virus particles at a permissible temperature of about 31° C., and which may be incapable of or poorly capable of producing virus particles at a semi-permissive temperatures of about 37° C. and incapable of producing virus particles at non-permissive temperatures above 37° C., for example 39° C. In certain embodiments, the $rVSV_{Ind}$ may include a M(G21E/L111F/M51R). In certain embodiments, the $rVSV_{Ind}$ may include an M gene comprising a nucleotide sequence SEQ ID NO: 2.

In certain embodiments, the rVSV is a full-length, essentially noncytolytic $rVSV_{NJ}$ M (G22E/M48R+M51R) or M(G22/L110F/M48R+M51R). In certain embodiments, the rVSV is an essentially noncytolytic $rVSV_{NJ}$ including an M gene, wherein the nucleotide sequence of the M gene is selected from SEQ ID NO: 6 and SEQ ID NO: 7.

The rVSVs of the present invention can be prepared using techniques known in the art. In one embodiment, the rVSVs may be introduced in a host cell under conditions suitable for the replication and expression of the rVSV in the host. Accordingly, the present invention also provides a cell having a $rVSV_{Ind}$ wherein the amino acid sequence of the virus' M protein is modified to provide an essentially non-cytotoxic which also allows the $rVSV_{Ind}$ to effectively replicate at permissible temperature but may not replicate at non-permissible temperature.

As such, the present invention relates also to a cell having one or more of the recombinant VSVs of the present invention.

Vaccines or Immunogenic Compositions of the Invention

The present invention further features vaccines or immunogenic compositions comprising one or more of the rVSVs of the present invention. In one embodiment, the present invention features vaccines or immunogenic compositions comprising an $rVSV_{Ind}$ and vaccines or immunogenic compositions comprising an $rVSV_{NJ}$, as described above.

In one embodiment, the vaccines may include rVSVs expressing an epitope of a pathogen. In another embodiment, the vaccines may include a mixture or cocktail of rVSVs expressing different epitopes of a pathogen (see Table 6, vaccination groups 5 and 6).

The vaccine or immunogenic compositions of the invention are suitable for administration to subjects in a biologically compatible form in vivo. The expression "biologically compatible form suitable for administration in vivo" as used herein means a form of the substance to be administered in which any toxic effects are outweighed by the therapeutic effects. The substances maybe administered to any animal or subject, preferably humans. The vaccines of the present invention may be provided as a lyophilized preparation. The vaccines of the present invention may also be provided as a solution that can be frozen for transportation. Additionally, the vaccines may contain suitable preservatives such as glycerol or may be formulated without preservatives. If appropriate (i.e. no damage to the VSV in the vaccine), the vaccines may also contain suitable diluents, adjuvants and/or carriers.

The dose of the vaccine may vary according to factors such as the disease state, age, sex, and weight of the individual, and the ability of antibody to elicit a desired response in the individual. Dosage regime may be adjusted to provide the optimum therapeutic response. The dose of the vaccine may also be varied to provide optimum preventative dose response depending upon the circumstances.

Kits

The present invention provides kits, for example for preventing or treating an infection. For example, a kit may comprise one or more pharmaceutical compositions or vaccines as described above and optionally instructions for their use. In still other embodiments, the invention provides kits comprising one or more pharmaceutical compositions or vaccines and one or more devices for accomplishing administration of such compositions.

Kit components may be packaged for either manual or partially or wholly automated practice of the foregoing methods. In other embodiments involving kits, this invention contemplates a kit including compositions of the present invention, and optionally instructions for their use. Such kits may have a variety of uses, including, for example, imaging, diagnosis, therapy, and other applications.

Advantages and Unique Features of the rVSVs of the Present Invention

Novel and Unusual Features of the Invention:

Normal assembly and release of $rVSV_{Ind}$ M(G21E/L111F/M51) at permissive temperature (about 31° C.) made it possible to amplify the new mutant rVSVs at the permissible temperature to a high titre to make viral stock. The assembly defectiveness of $rVSV_{Ind}$ M(G21E/L111F/M51) at non-permissive temperature (about 37° C. (around body temperature) increased the safety of the using the rVSV in human and other animals by significantly reducing the number of progeny infectious viruses at the non-permissive temperature. The addition of these mutations to the pre-existing M51R mutation in the M protein of $rVSV_{Ind}$ further attenuated the virulence of $VSV_{Ind}$.

The three mutations, M(G22E/M48R+M51R) or four mutations, M(G22E/L110F/M48R+M51R) in the M protein of $rVSV_{NJ}$ did not make the virus temperature sensitive for the assembly of the virus. However, the addition of G22E mutation or G22E/L110F to the M48R+51R mutations made the $VSV_{NJ}$ more attenuated and became significantly less pathogenic.

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

EXAMPLES

The present invention is further illustrated by the following examples which should not be construed as limiting in any way.

Example 1

Introduction of Mutations into the M Genes of $rVSV_{Ind}$ and $rVSV_{NJ}$ and Recovery of Recombinant VSV by Reverse Genetics Mutations were introduced into the M gene of $VSV_{Ind}$ (FIG. 1) and $VSV_{NJ}$ (FIG. 2). Nucleotide sequences encoding the amino acids at each position were mutated by the mega-primer PCR method. Each mutation is expressed as a substitution of an amino acid at a specific position (e.g., M51 in M51R) with another amino acid (e.g., R in M51R). In order to attenuate further the virulence of VSV, the inventors combined mutations (G21E and L11F) in the tsO23 with methionine to arginine mutations (M51R) in the M gene, which reduced inhibitory activity of M protein on the cellular protein synthesis, in addition, reduced the assembly of the VSV particles at non-permissive (39° C.) and semi-permissive (37° C.) temperatures. The nucleotide sequences and amino acid changes from wild type to mutants in the M genes of $rVSV_{Ind}$ and $rVSV_{NJ}$ are shown in Tables 2, 3, 4 and 5. The changed nucleotide codons are underlined and changed nucleotide sequences and amino acid sequences are bold-faced.

Wild type and mutant recombinant vesicular stomatitis viruses (rVSV) were recovered from the cDNA plasmids by reverse genetics (FIG. 3). The VSV reverse genetics employs the BHK21 cells expressing DNA dependant RNA polymerase of bacteriophage T7 (T7) and a plasmid which encodes full length genomic RNA of VSV (pVSV) and 3 plasmids expressing nucleocapsid protein (pN), phosphoprotein (pP), and VSV polymerase L protein (pL). The transcription of the full length genomic RNA and the messenger RNAs for N, P, and L proteins are under the control of T7 RNA polymerase. Internal ribosome entry site (IRES) at the upstream of each VSV N, P, and L gene enhances the translation of proteins. The plasmids are transfected into BHK-T7 cells with Lipofectamine™ 2000 in concentrations of 10 µg of pN, 10 µg of pP, µ5 g of pL, and 15 µg of pVSV. The culture media from the transfected cells were harvested when the cells showed about 50-70% of CPE.

Example 2

The Mutation, L111F in the M Gene Significantly Reduces the Burst Sizes of $rVSV_{Ind}$ at Semi-Permissive Temperature, 37° C.

Figure 4:
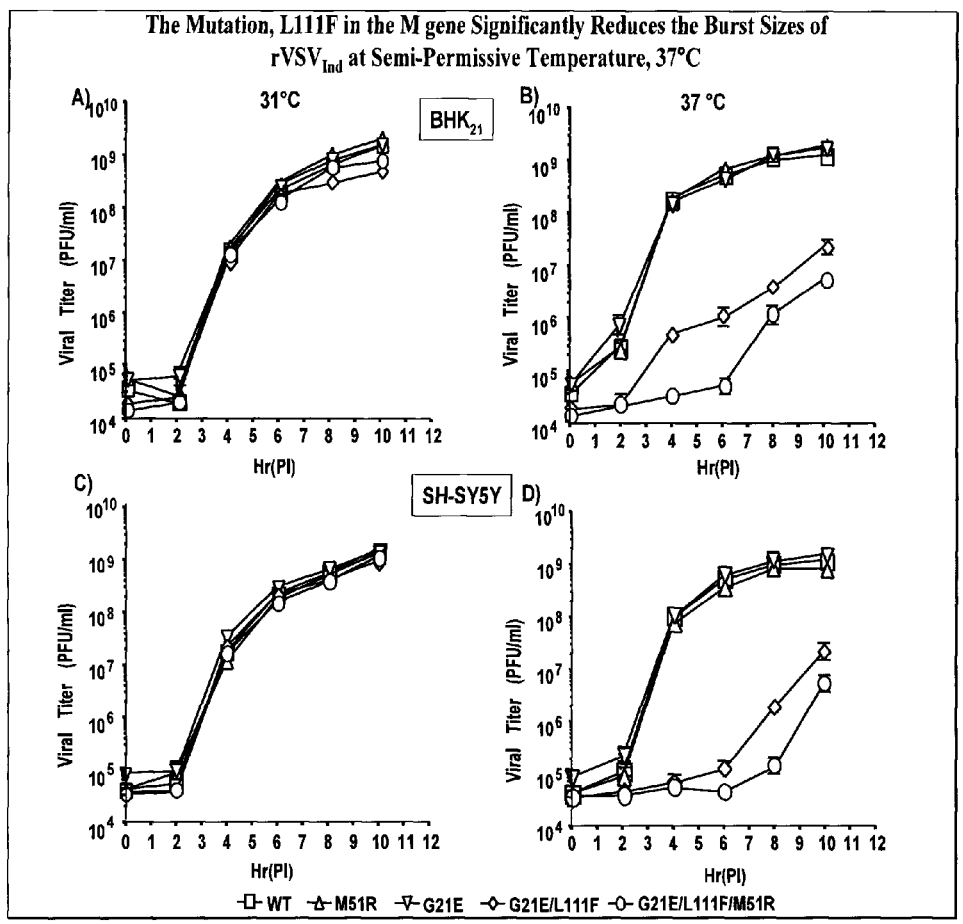
FIG. 4 illustrates the burst size effect of mutation L111F in the M protein of rVSV$_{Ind}$ at permissive temperature [panels A) and C)] and at semi-permissive temperature [panels B) and D)], in baby hamster kidney (BHK) cells infected with recombinant VSVs [panels A) and B)] and in human neuroblastoma cells (SH-SY5Y) infected with the rVSV.

The recovered viruses were purified 3 times by plaque picking and were amplified for a larger volume of stock viruses by infecting BHK21 cells with an MOI of 0.1 at 31° C. The inventors infected BHK21 cells and human neuroblastoma cells, SH-SY5Y with an MOI of 3 of rVSVs. The infected cells were incubated at permissive temperature (31° C.) and semi-permissive temperature (37° C., body temperature) to determine the temperature sensitivity of the new M mutants in the assembly of virus particles. Culture media from the infected cells were collected every 2 hours until 10 hours after the infection, and the number of infectious viral particles in the culture media was determined by plaque assay with Vero E6 cells. The cells infected with the mutant viruses for the plaque assay were incubated at 31° C. Wild type and all mutants replicated equally well and produced similar titre of infectious viruses all along the period of 10 hrs of infection (FIGS. 4A and C). However, the mutants of $rVSV_{Ind}$, $rVSV_{Ind}$-G21E/L111F and $rVSV_{Ind}$-G21E/L111F/M51R replicated in significantly lower titre than wild type or M51R mutant of $rVSV_{Ind}$ at 37° C. The differences in producing infectious particles between the wild type and the new M mutant, $rVSV_{Ind}$-G21E/L111F/M51R were as large as four logs (FIGS. 4B and D). The error bars in FIG. 4 represent standard error of the mean. The P values for viral titers of $rVSV_{Ind}$-G21E/L111F/M51R at 4 hrs, 6 hrs, 8 hrs, and 10 hrs postinfection obtained by comparing them to titers of $rVSV_{Ind}$-WT are $p<0.0001$, $p=0.0055$, $p=0.0040$, and $p=0.0015$ in FIG. 4B. The P values for viral titers of $rVSV_{Ind}$-G21E/L111F at 4 hrs, 6 hrs, 8 hrs, and 10 hrs postinfection obtained by comparing them to titers of $rVSV_{Ind}$-WT are $p<0.0001$, $p=0.0055$, $p=0.0041$, and $p=0.0016$

Example 3

Mutations in the M Gene of rVSV$_{NJ}$, G22E and L110F do not Reduce the Burst Size of the rVSV$_{NJ}$ at 37° C.

BHK21 cells were infected with an MOI of 3 of rVSV$_{NJ}$, wild type and M gene mutants, incubated at both 37° C. (semi-permissive temperature) and 31° C. (permissive temperature) and the culture media was harvested at 10 hrs post infection. The viral titer of each virus in the culture media was determined by plaque assay using Vero E6 cells. The average viral titre from the duplicate samples is shown in the table. Wild type and all M mutants of rVSV$_{NJ}$ replicated equally well at both temperatures 31° C. and 37° C. (FIG. 5), indicating the introduction of G22E and L110F mutations into the M gene of rVSV$_{NJ}$ did not affect the assembly and release of the virus at 37° C. The error bars in FIG. 5 represent standard error of the mean.

Example 4

Assembly Defectiveness at Semi-Permissive Temperature by L111F Mutation in the M Gene of rVSV$_{Ind}$ does not Affect the Expression of VSV Proteins BHK21 cells were infected with an MOI of 6 of rVSV$_{Ind}$ and rVSV$_{NJ}$, wild type and M gene mutants. The infected cells were incubated at both 37° C. and 31° C. for 6 hrs. The infected cells were lysed at 6 hrs post-infection, 5 µg of total protein was loaded to the SDS-PAGE gel, and rVSV proteins were detected by Western blot analysis using rabbit antiserum against VSV$_{Ind}$ and VSV$_{NJ}$ (1:5000 dilution). The result demonstrate that in spite of the mutations that reduced the burst size of the rVSV$_{Ind}$ at 37° C. (L111F in G21E/L111F and G21E/L111F/M51R), the level of VSV protein expression is comparable to the wild type rVSV$_{Ind}$ (FIG. 6A). Wild type and all M mutants of rVSV$_{NJ}$ expressed their proteins in a similar level at both 31° C. and 37° C. (FIG. 6B).

Example 5

Figure 7:
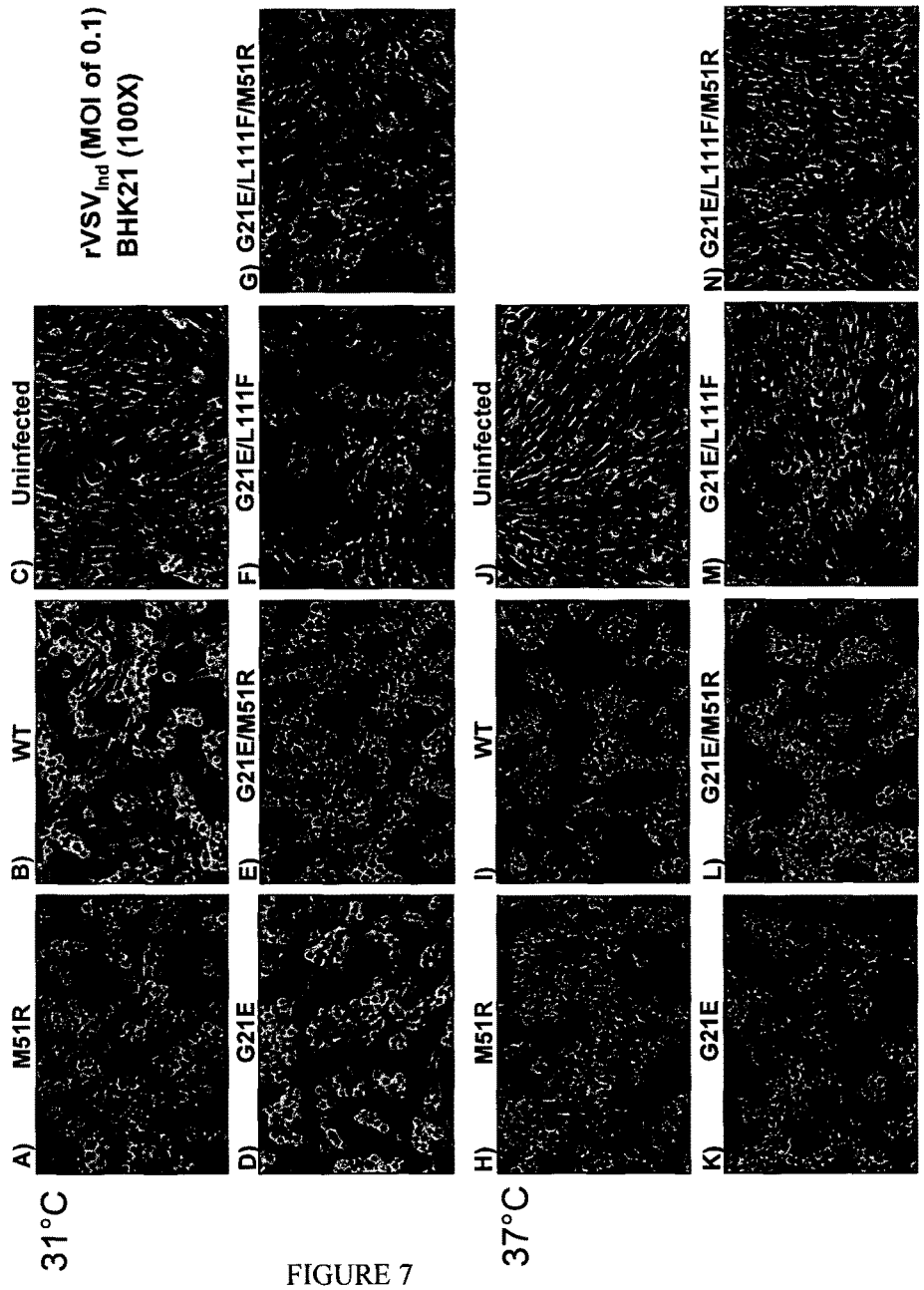
FIG. 7 includes photographs of BHK21 cells infected with rVSV$_{Ind}$ having a wild type M gene (panels B and I) and with rVSV$_{Ind}$ having different mutations in the M gene (panels A, D, E, F, G, H, K, L, M and N) and photographs of uninfected BHK21 cells (panels C and J). Cells were incubated at 31° C. (panels A to G) or 37° C. (panels H to N).
Figure 8:
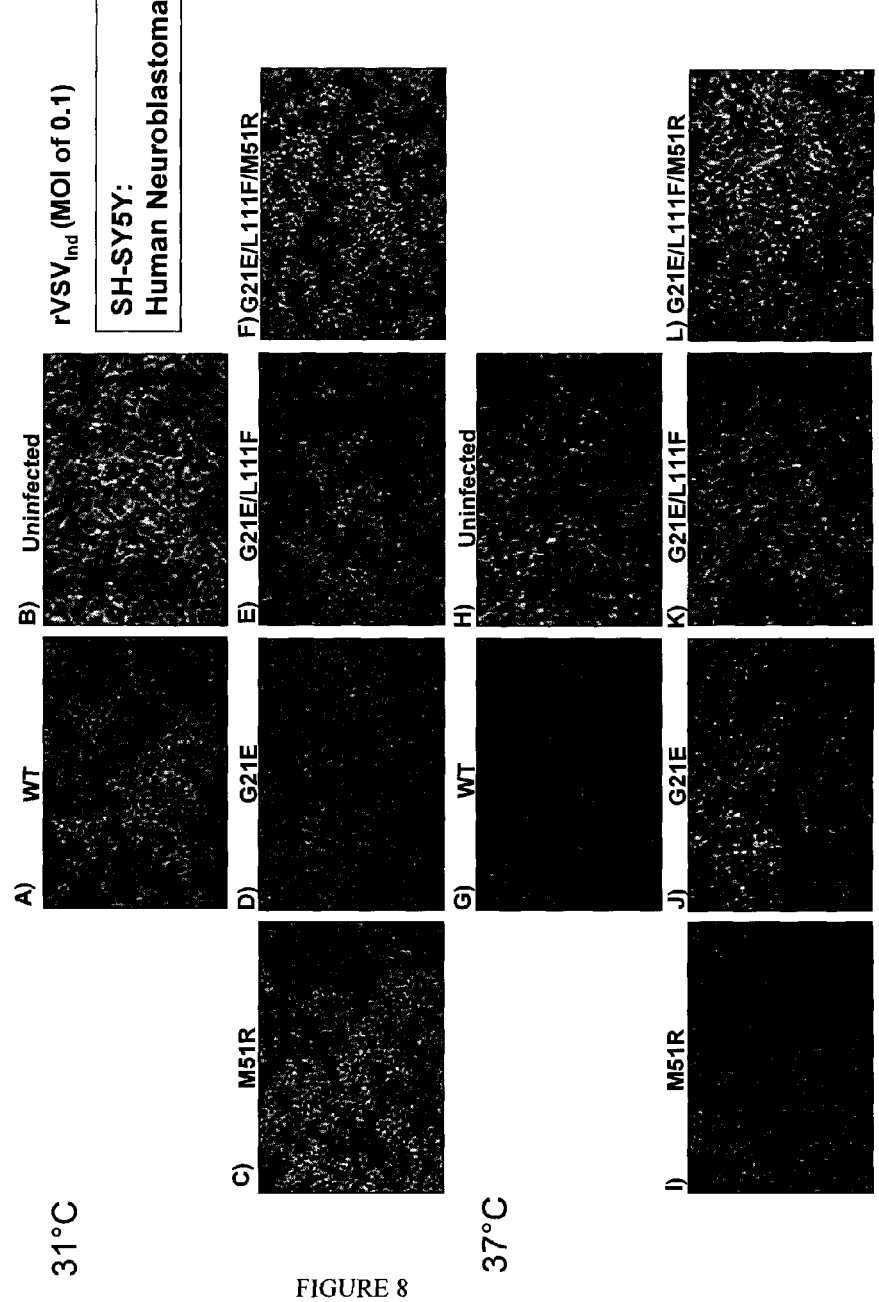
FIG. 8 includes photographs of SH-SY5Y cells infected with rVSV$_{Ind}$ having different mutations in the M gene (panels C, D, E, F, I, J, K and L) or wild type M gene (panels A and G) and photographs of uninfected SH-SY5S cells (panels B and H). Cells were incubated at 31° C. (panels A to F) or 37° C. (panels G to L).

Combined Mutations, G21E/L111F/M51R in the M Gene of rVSV$_{Ind}$ Reduced Cytopathogenicity Significantly in BHK21 Cells and Human Neuroblastoma Cells, SH-SY5Y In order to examine the effects of the mutations, L111F and M51R of M gene of rVSV$_{Ind}$ on the cytopathogenicity, the inventors infected BHK21 cells (FIG. 7) and human neuroblastoma cells (FIG. 8) with, an MOI of 0.1 of rVSV$_{Ind}$. The typical cytopathic effects by the VSV are rounding-up of infected cells and cell lysis. At 20 hrs after infection, the cytopathic effect caused by the rVSV$_{Ind}$-G21E/L111F/M51R was compared with those by the other rVSV$_{Ind}$. In 20 hrs of infection with the rVSV$_{Ind}$-G21E/L111F/M51R mutant showed the most reduced cytopathic effects, none or small number of round-up cells at 37° C. and the combination of the mutations L111F and M51R (FIG. 7N and FIG. 8L) further attenuated the cytopathogenicity of the virus than the single mutation of each in both BHK21 and SH-SY5Y cells.

Example 6

Figure 9:
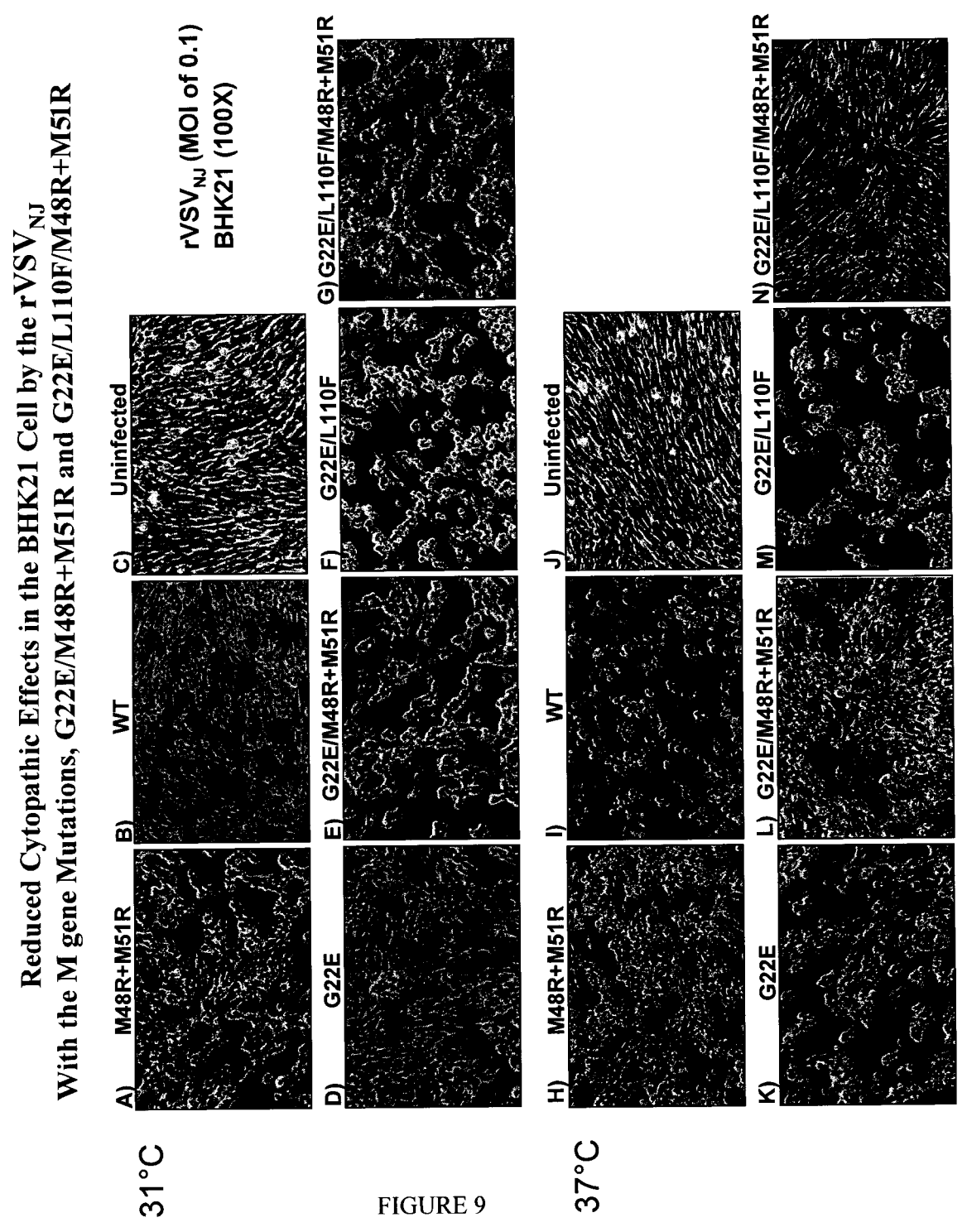
Figure 10:
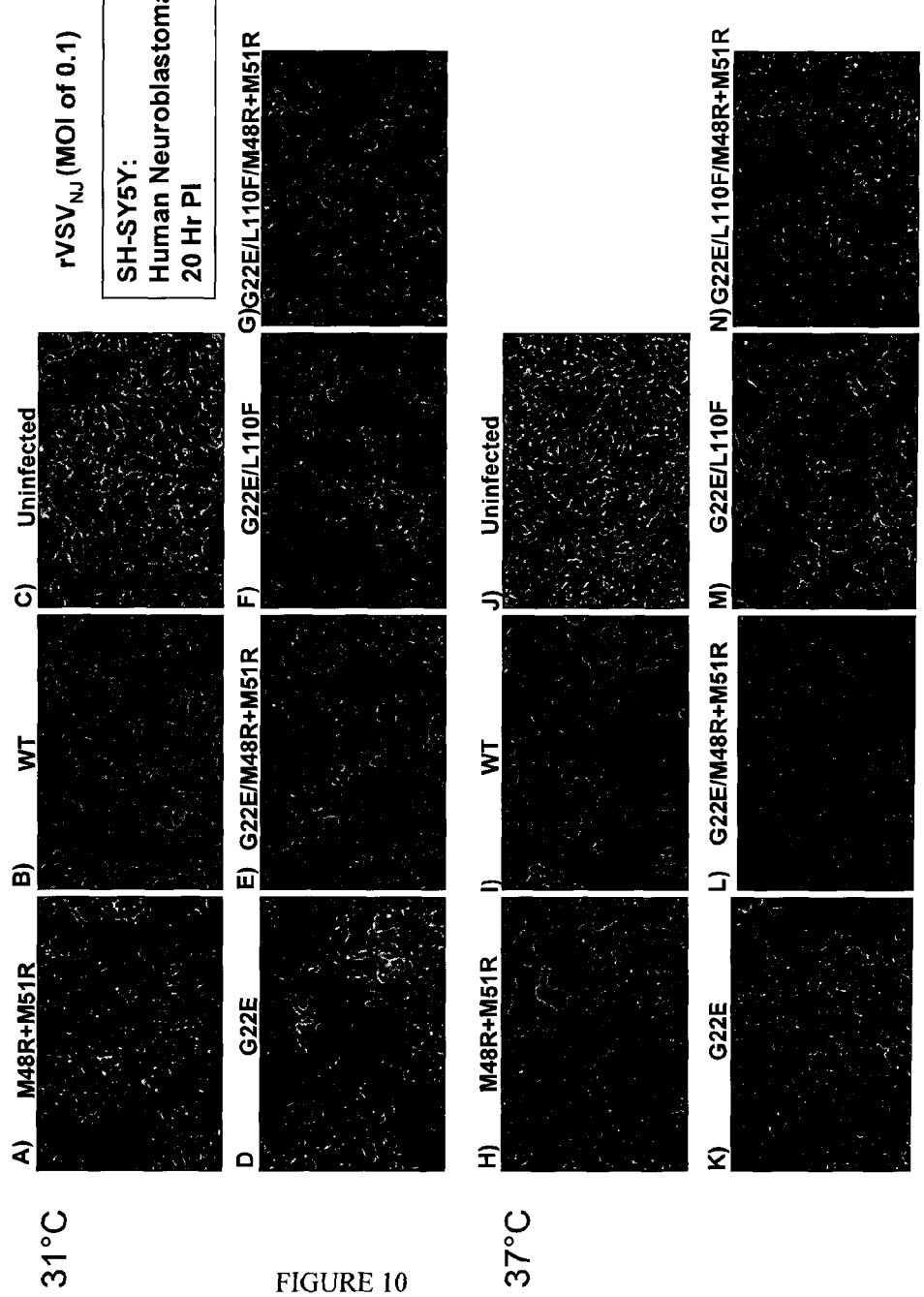
FIG. 10 includes photographs of SH-SY5Y cells infected with rVSV$_{NJ}$ having different mutations in the M gene (panels A, D, E, F, G, H, K, L, M, and N) or having wild type M gene (panels B and I), and photographs of uninfected SH-SY5Y cells (panels C and J). Cells were incubated at 31° C. (panels A to G) or 37° C. (panels H to N).

Reduced Cytopathic Effects in the BHK21 Cell by the rVSV$_{NJ}$ with the M Gene Mutations, G22E/M48R+M51R and G22E/L110F/M48R+M51R In order to examine the effects of the mutations, G22E, L110F and M48R+M51R of M gene of rVSV$_{NJ}$ on the cytopathogenicity, the inventors infected BHK21 cells and human neuroblastoma cells with an MOI of 0.1 of rVSV$_{NJ}$. At 20 his after infection, the inventors compared the cytopathic effects (cell round-up and lysis) caused by the rVSV$_{NJ}$ wild type and other M mutants. In 20 hrs of infection with the G22E/M48R+M51R mutant and G22E/L110F/M48R+M51R mutant showed the least cytopathic effects at 37° C. and the combination of the mutations, G22E and M48R+M51R further attenuated the cytopathogenicity of the rVSV$_{NJ}$ in both BHK21 (FIGS. 9L and 9N) and SH-SY5Y cells (FIGS. 10L and 10N).

Example 7 rVSV$_{Ind}$ with the Mutations of G21E/L111F/M51R and rVSV$_{NJ}$ with the Mutations of G22E/M48R+M51R and G22E/L110F/M48R+M51R in the M Protein was Attenuated to a Degree that Mice Injected with the Virus into the Brain Showed No Neurological Signs or any Symptoms Such as Weight Loss VSV does not show the neurotropism in host animal during the natural infection through the skin abrasion or sandfly or mosquito bites. Nevertheless, when wild type VSV is injected directly into the nose or brain in mice or monkeys, the animals demonstrate neurological symptoms. In order to examine the neurovirulence of the new M mutants of VSVs, the inventors injected Swiss Webster mice with 1×10$^6$ PFU of mutant VSV and 1×10$^3$ PFU of wild type VSV into the intralateral ventricle of the brain. The inventors purchased 5-week-old Swiss Webster mice with intralateral ventricular implant from Charles River laboratory. Three mice/group were injected with viruses after one week of arrival to the animal facility. After the viral injection, mice were observed for neurological signs and were weighed every two days for 4 weeks. The mice injected with 1×10$^3$ PFU of wild type rVSV$_{Ind}$ died within four days after injection (FIG. 11B). Two mice injected with 1×10$^6$ PFU of rVSV$_{Ind}$-M51R (FIG. 11C) lost about 20% of body weights 6 days after injection and the body weight bounced back to normal weight at about 14 days after injection. One mice injected with the rVSV$_{Ind}$-M51R did not lose the body weight through the experiment. All three mice injected with rVSV$_{Ind}$-G21E/L111F/M51R showed no sign of illness and did not lose their body weight for 4 weeks until the mice were sacrificed (FIG. 11D) indicating the combination of mutations, G21E/L111F and M51R significantly attenuated the rVSV$_{Ind}$ and lost its neurovirulence in mice. One mice injected with rVSV$_{NJ}$-WT showed paralysis in both hind legs and it was sacrificed on day 6 after injection (FIG. 12A). Two other mice injected with rVSV$_{NJ}$-WT and mice injected with rVSV$_{NJ}$-M48R+M51R, rVSV$_{NJ}$-G22E/M48R+M51R, or rVSV$_{NJ}$-G22E/L110F/M48R+M51R showed no sign of illness and weight loss during 4 weeks after injection (FIGS.

Figure 11:
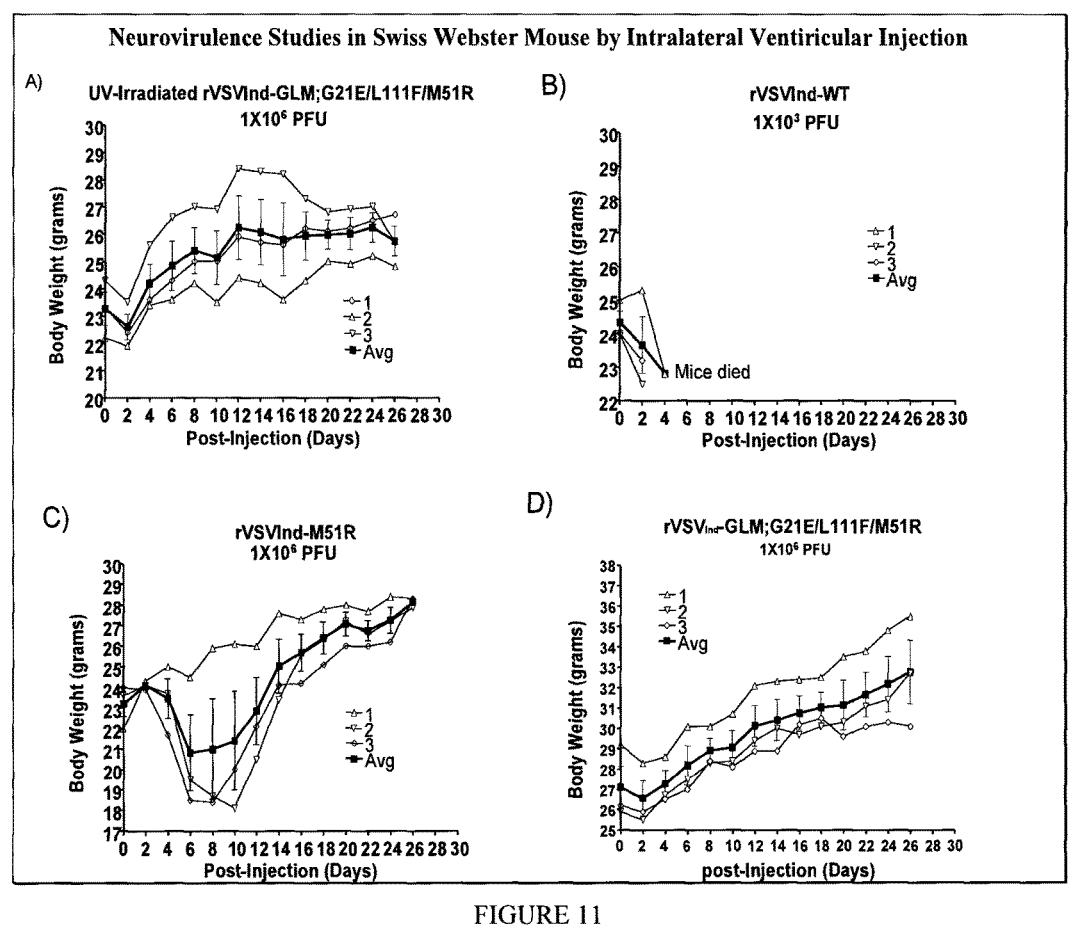
Figure 12:
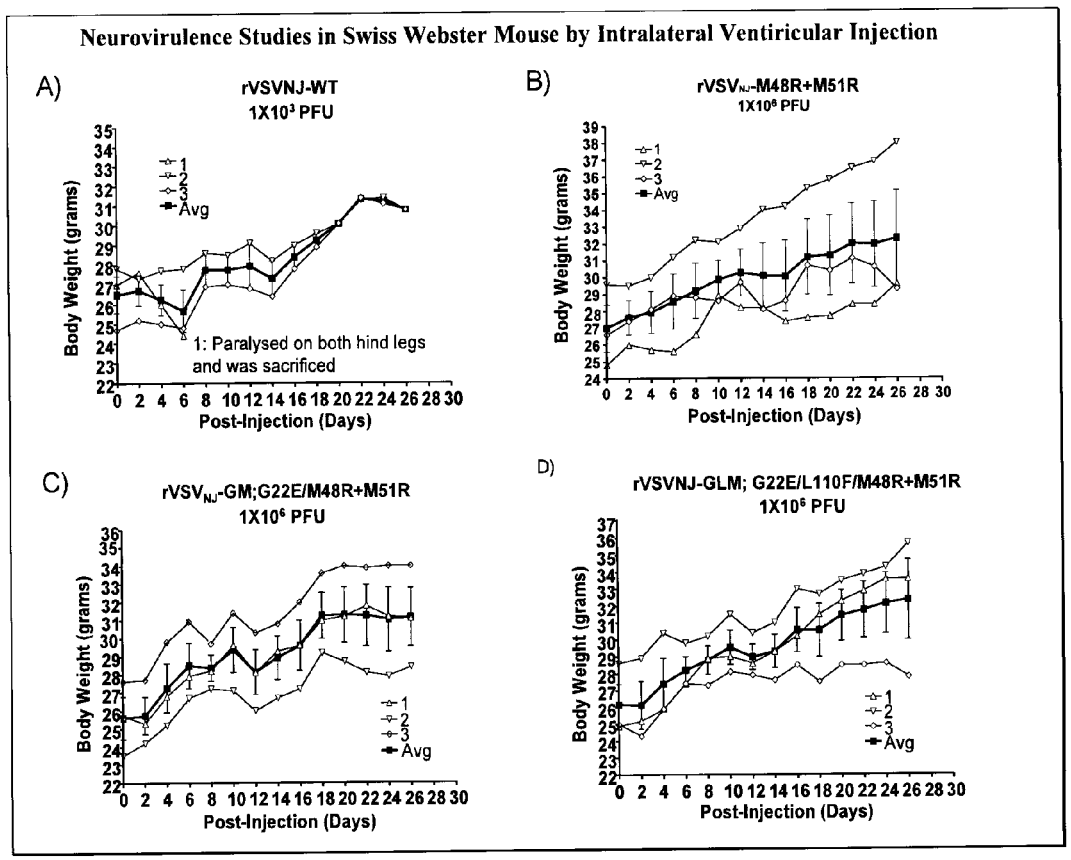
FIG. 12 includes graphs illustrating neurovirulence studies in Swiss Webster mouse by intralateral ventricular injection: A) rVSV$_{NJ}$ WT, B), rVSV$_{NJ}$ M48R+M51R, C) rVSV$_{NJ}$ G22E/M48R+M51R and D) rVSV$_{NJ}$ G22E/L110F/M48R+M51R.

12B, 12C, and 12D). The error bars in FIGS. 11 and 12 represent standard error of the mean.

Example 8

Generation of rVSVs Expressing HIV-1 Gag Protein as a Gene of Interest; HIV-1 Gag Proteins are Expressed Equally Well at Both 31° C. and 37° C.

Figure 13:
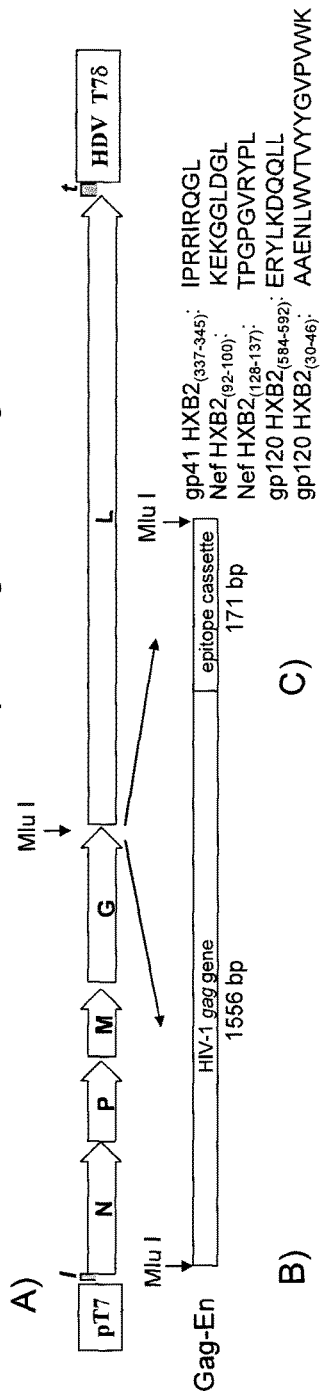
FIG. 13 (SEQ ID NOS: 11-15) A) illustrates the cloning of HIV-1 Gag-En genes into the cDNA clone of rVSV.
Figure 13:
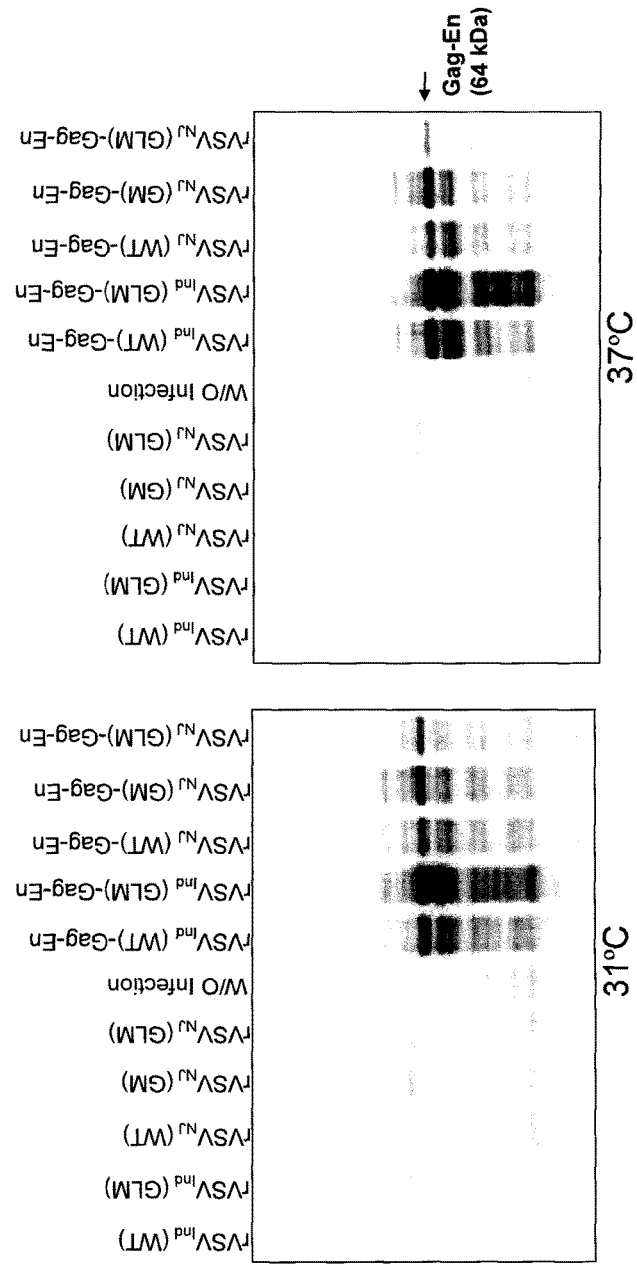

The newly generated M mutants, G21E/L111F/M51R mutant of rVSV$_{Ind}$ and G22E/M48R+M51R and G22E/L110F/M48R#M51R mutants of rVSV$_{NJ}$ demonstrated the reduced cytopathogenicity and comparable protein expressions to the wild type rVSV at 37° C. In order to be used as a vaccine vector, the new M mutants of rVSV should induce good immune responses in vivo, both humoral and cellular immune responses. When it is expressed alone in cells, HIV-1 gag proteins produce virus like particles and the virus like particles are secreted from the cells. Therefore, the gag protein was suitable protein to express from the new M mutants of rVSV to examine both cellular and humoral immune response. In addition, the CD8+ cytotoxic T cell epitope, H-2K$^d$-restricted peptide (NH$_2$-AMQMLKETI-COOH) (SEQ ID NO: 33) in the HIV-1 Gag is well studied in the Balb/c mouse. The inventors inserted the full-length HIV-1 gag gene linked to conserved human CD8+ T cell epitopes from gp41, gp120, and nef protein of HIV-1 (Gag-En). The Gag-En gene was inserted into the junction of G gene and L gene in the full-length cDNA, clones of wild type (WT) and G21E/L111F/M51R (GLM) of rVSV$_{Ind}$ and wild type, G22E/M48R+M51R (GM), and G22E/L110F/M48R+M51R(GLM) of rVSV$_{NJ}$. The rVSVs were recovered from the cDNA, clones by reverse genetics as described in FIG. 3 and the expression of Gag-En from the rVSVs was examined by Western blot analysis using monoclonal antibody against HIV-1 p24. For the Western blot analysis, BHK21 cells were infected with MOI of 6 of rVSVs and incubated at 31° C. and 37° C., and cell lysates were prepared at 6 hrs post-infection. Total protein of 5 µg was loaded onto the SDS-PAGE for the Western blot analysis. rVSV$_{Ind}$(GLM)-Gag-En, rVSV$_{NJ}$(GM)-Gag-En, and rVSV$_{NJ}$(GLM)-Gag-En expressed Gag-En protein (64 kDa) well at semi-permissive temperature (37° C., FIG. 13C) and the expression level was similar to that at permissive temperature (31° C., FIG. 13B).

Example 9

Vaccination Regimen with rVSV in Mice

Figure 14:
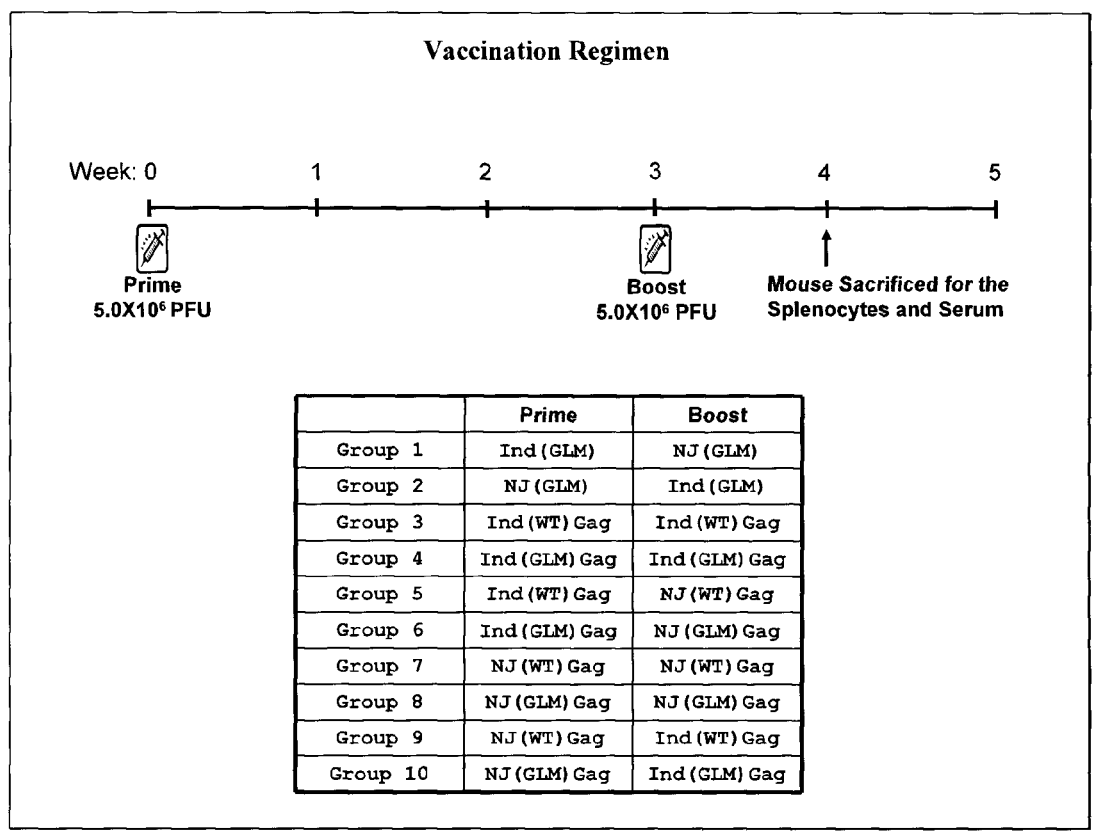
FIG. 14 depicts a vaccination regime and a table of vaccination groups.

Six Balb/C mice per group were vaccinated with the prime-boost regimen illustrated in FIG. 14. Mice were grouped according to the vaccine vector type (wild type vs. mutant) and regimen, e. g., priming and boosting with the same serotype of rVSV or alternating the two serotypes for priming and boost. The mice were prime-vaccinated intramuscularly with 5×10$^6$ PFU of rVSVs at age of 6 weeks. Three weeks after the priming, mice were boost-vaccinated with the same dose of rVSV as the prime vaccination. A week after the booster injection, splenocytes and sera were collected to detect the HIV-1 Gag specific CD8+ T cell immune responses and humoral immune responses.

Example 10

Figure 15:
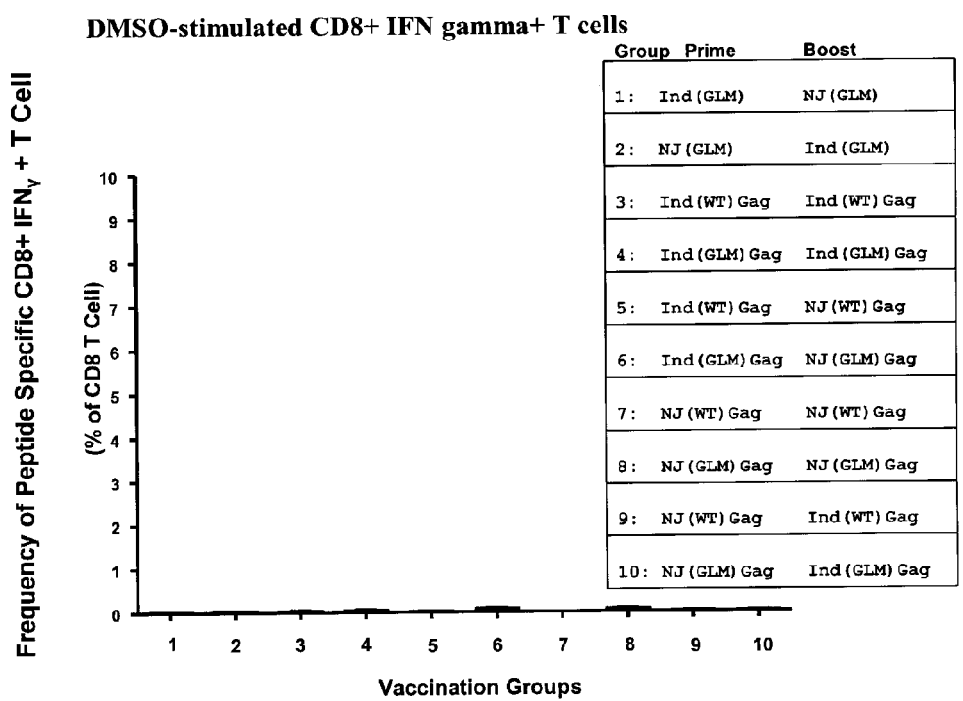
FIG. 15 depicts a graph of the frequency of peptide specific CD8+ IFN gamma+ T cells among the different vaccination groups illustrated in the insert stimulated with dimethyl sulfoxide (DMSO).
Figure 16:
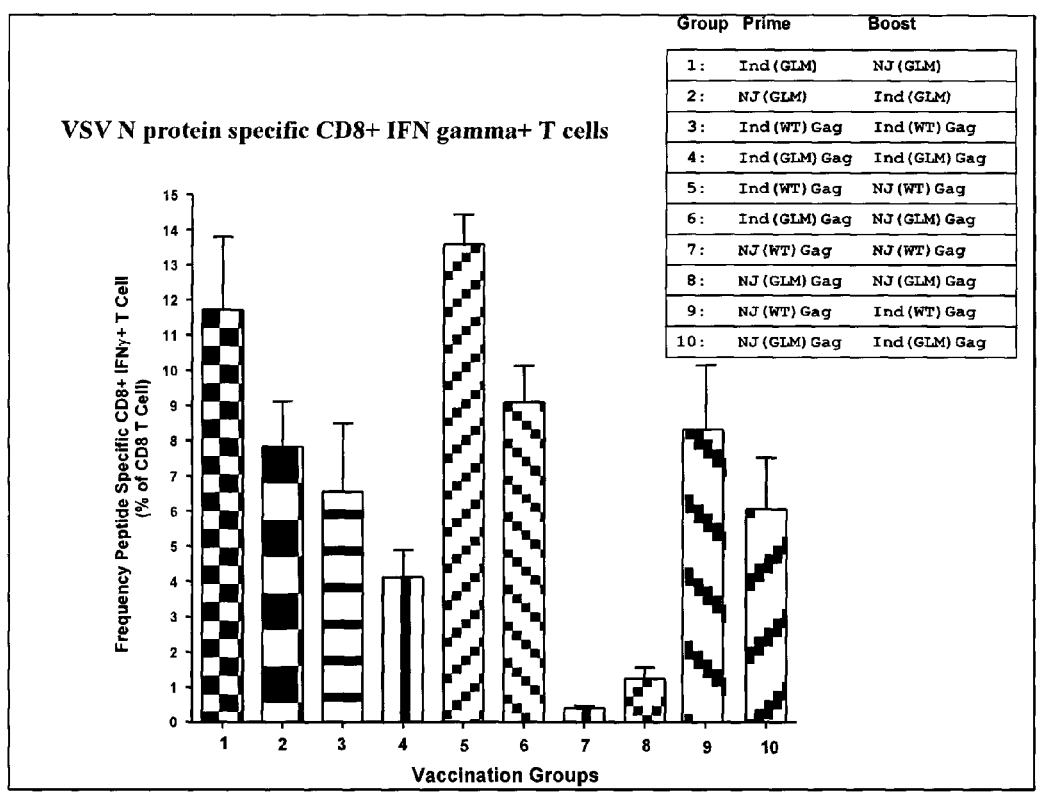
FIG. 16 is a graph illustrating the frequency of VSV N peptide specific CD8+ IFN gamma+ T cells among the different vaccination groups illustrated in the insert stimulated with VSV N.
Figure 17:
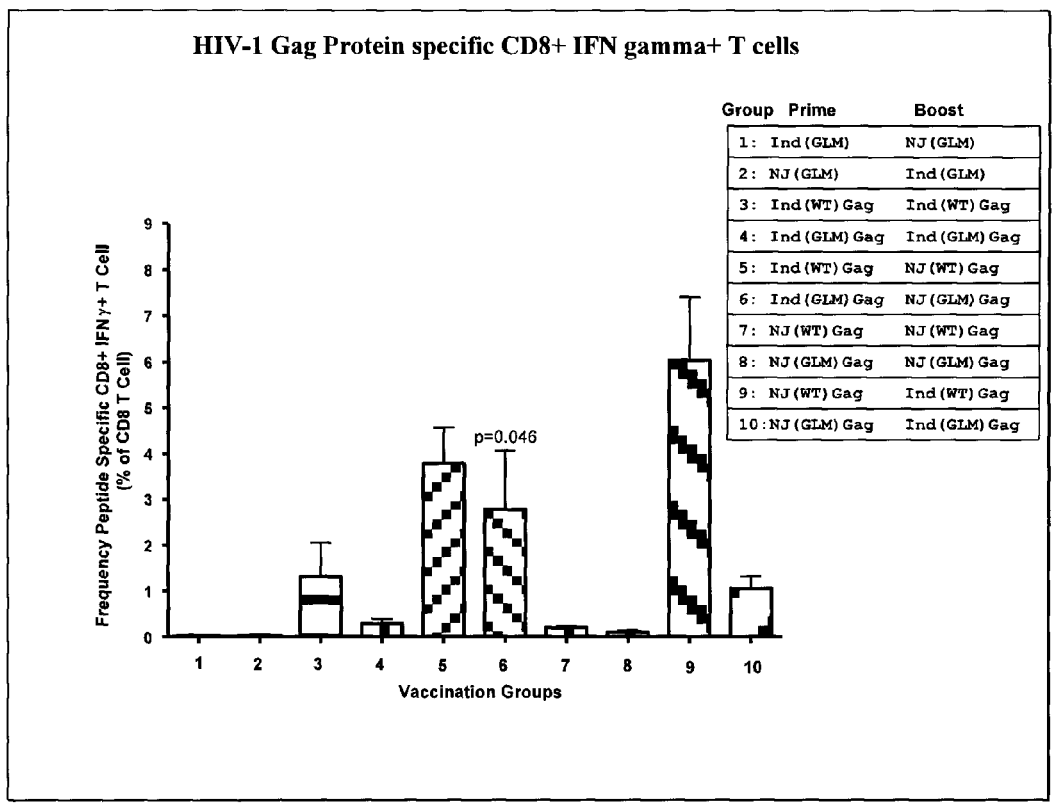
FIG. 17 is a graph illustrating the frequency of HIV-1 Gag peptide specific CD8+ IFN gamma+ T cells among the different vaccination groups illustrated in the insert stimulated with HIV-1 Gag.

Priming with rVSV$_{Ind}$(GLM)-HIV-1 Gag-En and Booster with rVSV$_{NJ}$(GLM)-HIV-1 Gag-En Induces Strongest CD8+ T Cell Immune Responses Against HIV-1 Gag The T cells stimulated by the interaction with MHC I molecule on the antigen presenting cells loaded with the peptide enhances the secretion of interferon-γ (IFN-γ), which indicates the antigen specific T cell immune responses. The splenocytes were double stained with FITC-anti-CD8 and APC-anti-IFN-γ for CD8+ T cells with the increased intracellular INF-γ. In order to examine the HIV-1 Gag protein specific CD8+ T cell immune response, splenocytes were isolated and 1×10$^6$ cells were stimulated with H-2K$^d$-restricted HIV-1 Gag peptide, NH$_2$-AMQMLKETI-COOS (SEQ ID NO: 33), the cells were stained with FITC rat anti-mouse CD8 for the CD8 molecules and stained with APC rat anti-mouse IFN-γ for intracellular IFN-γ. The secretion of IFN-γ was blocked with Brefeldin A before staining them. VSV specific CD8+ T cell immune responses were examined with the use of nucleocapsid specific peptide, IN275: NH2-MPYLIDFGL-COOH (SEQ ID NO: 32). Peptide specific CD8+-IFN-γ+ T cells were counted with FACSCalibur, a flowcytometer. The splenocytes treated with DMSO (solvent for the peptide, FIG. 15) did not stimulate the CD8+ T cells indicating that treating the splenocytes with the VSV N peptides and HIV-1 Gag peptides stimulated specifically CD8+ T cells in FIG. 16 and FIG. 17. Prime and boost immunization by alternating two serotypes of rVSV (WT) or rVSV(GLM) mutants induced stronger CD8+ T cell immune responses against VSV as well as HIV-1 Gag proteins than using a single serotype of rVSV for the prime and boost vaccinations as seen in groups 1, 2, 5, 6, 9, and 10. (FIG. 16 and FIG. 17). With the vaccination with the new M mutants or rVSV, CD8+ T cell responses against HIV-1 Gag protein was induced better when mice were vaccinated with rVSV$_{Ind}$(GLM)-Gag for priming and rVSV$_{NJ}$(GLM)-Gag for boosting than vice versa (FIG. 17, group 6 vs. group 10). P value on the group 6 in FIG. 17 was computed by using two-sided independent sample t test, and the result was compared to that for the group 10. The error bars in FIGS. 16 and 17 represent standard error of the mean.

Example 11

HIV-1 Gag Specific Humoral Immune Responses

Figure 18:
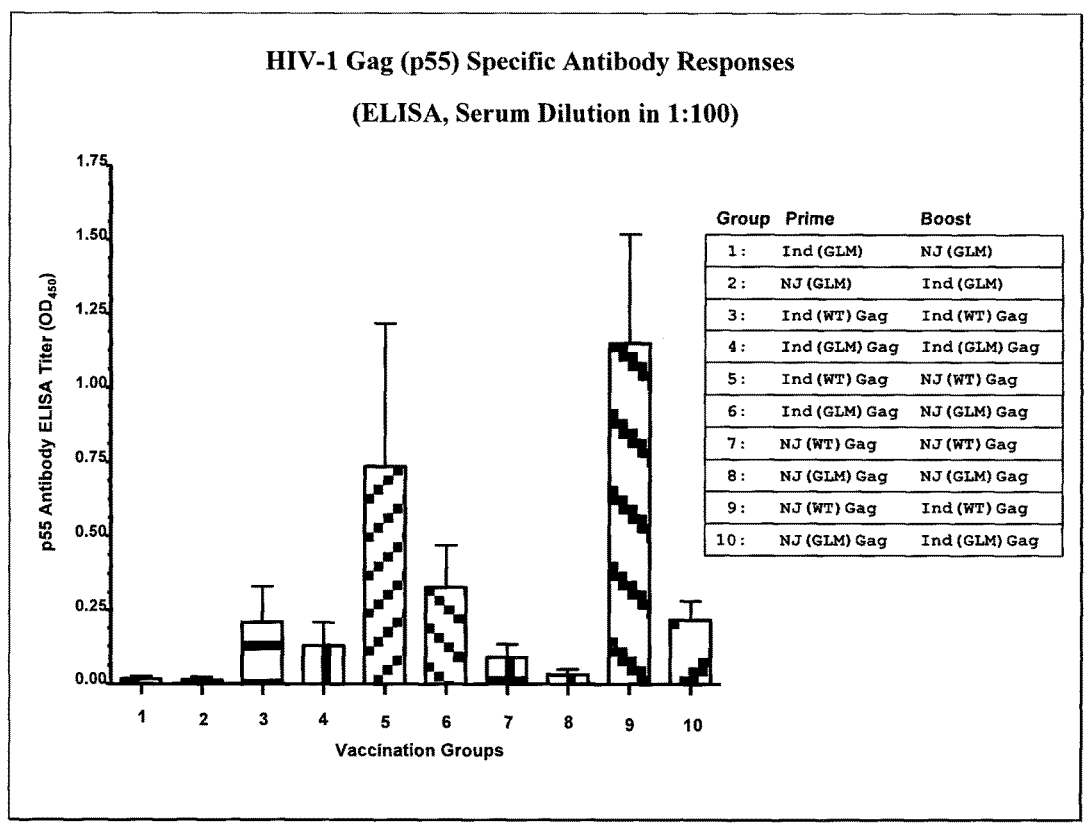
FIG. 18 is a graph illustrating HIV-1 Gag specific antibody responses among the different vaccination groups illustrated in the insert.

Generation of HIV-1 Gag specific antibody was examined with the serum collected at a week after the boost immunization. The Gag specific antibody titer was determined by the indirect enzyme-linked immunosorbent assay (ELISA). For the ELISA, 96 well ELISA plate was coated with recombinant p55 at a concentration of 125 ng/well. The mouse serum was diluted 1:100. The antibody bound to the antigen, p55 was detected with secondary antibody, sheep anti-mouse IgG-HRP. The enzymatic activity of HRP was detected by adding substrates, a mixture of hydrogen peroxide and tetramethylbenzidine. The OD of each sample was read at the wavelength of 450 with the microplate reader. The humoral immune responses against HIV-1 Gag (generation of antibody against HIV-1 Gag) was induced well in mice vaccinated with the new M mutants, and the best humoral immune responses against HIV-1 Gag were induced when two serotypes of rVSV(WT) or rVSV(GLM) were alternated for prime and booster injection (FIG. 18, groups 5, 6, 9, and 10). As for the utilization of the new M mutants for inducing humoral immune responses against foreign proteins, priming with rVSV$_{Ind}$(GLM)-Gag and booster with rVSV$_{NJ}$(GLM)-Gag worked better than vice versa (Gig. 18, group 6 vs. group 10). The error bars in FIG. 18 represent standard error of the mean.

Example 12

Increasing Doses of rVSV$_{Ind}$(GLM), rVSV$_{NJ}$(GM), and rVSV$_{NJ}$(GLM) for Vaccination Induced Stronger Immune Responses in Mice As illustrated in FIG. 17 and FIG. 18, stronger HIV-1 Gag specific CD8+ T cell immune responses and humoral immune responses were induced when mice were prime vaccinated with rVSV$_{Ind}$(GLM)-Gag and booster vaccinated with rVSV$_{NJ}$(GLM)-Gag. However the immune responses were not as strong as those induced with rVSV$_{Ind}$(WT)-Gag and rVSV$_{NJ}$(WT)-Gag. Therefore, the inventors wanted to examine whether they could increase the immune responses, if they increase the doses of the rVSV$_{Ind}$(GLM)-Gag and rVSV$_{NJ}$(GLM)-Gag. Six (6) week old Balb/c mice, 6 mice/group, were vaccinated with rVSV$_{Ind}$(GLM)-Gag for priming and rVSV$_{NJ}$(GLM)-Gag or rVSV$_{NJ}$(GM)-Gag for booster. Because the rVSV$_{NJ}$(GM) was as attenuated as the rVSV$_{NJ}$(GLM) in vitro and in vivo, the inventors included rVSV$_{NJ}$(GM)-Gag as a booster virus, and compared the immune responses to that induced by rVSV$_{NJ}$(GLM)-Gag. Mice groups were vaccinated with various doses of rVSV$_{Ind}$(GLM)-Gag, rVSV$_{NJ}$(GLM)-Gag, and rVSV$_{NJ}$(GLM)-Gag; 5×10$^6$ PFU/mouse, 5×10$^7$ PFU/mouse, 5×10$^8$ PFU/mouse, and 5×10$^9$ PFU/mouse (Table 1).

Mice were vaccinated according to the schedule as seen in FIG. 14 and were sacrificed a week after booster vaccination for splenocytes and serum. The splenocytes were double stained with FITC-anti-CD8 and APC-anti-IFN-γ for CD8+ T cells with the increased intracellular INF-γ. In order to examine the HIV-1 Gag protein specific CD8+ T cell immune response, splenocytes were isolated and 1×10$^6$ cells were stimulated with H-2Kd-restricted HIV-1 Gag peptide, NH2-AMQMLKETI-COOH (SEQ ID NO: 33), the cells were stained with FITC rat anti-mouse CD8 for the CD8 molecules and stained with APC rat anti-mouse IFN-γ for intracellular IFN-γ. The secretion of IFN-γ was blocked with Brefeldin A before staining them. VSV specific CD8+ T cell immune responses were examined with the use of nucleocapsid specific peptide, IN275: NH2-MPYLIDFGL-COOH (SEQ ID NO: 32). Peptide specific CD8+-IFN-γ+ T cells were counted with FACSCalibur, a flowcytometer.

Figure 19:
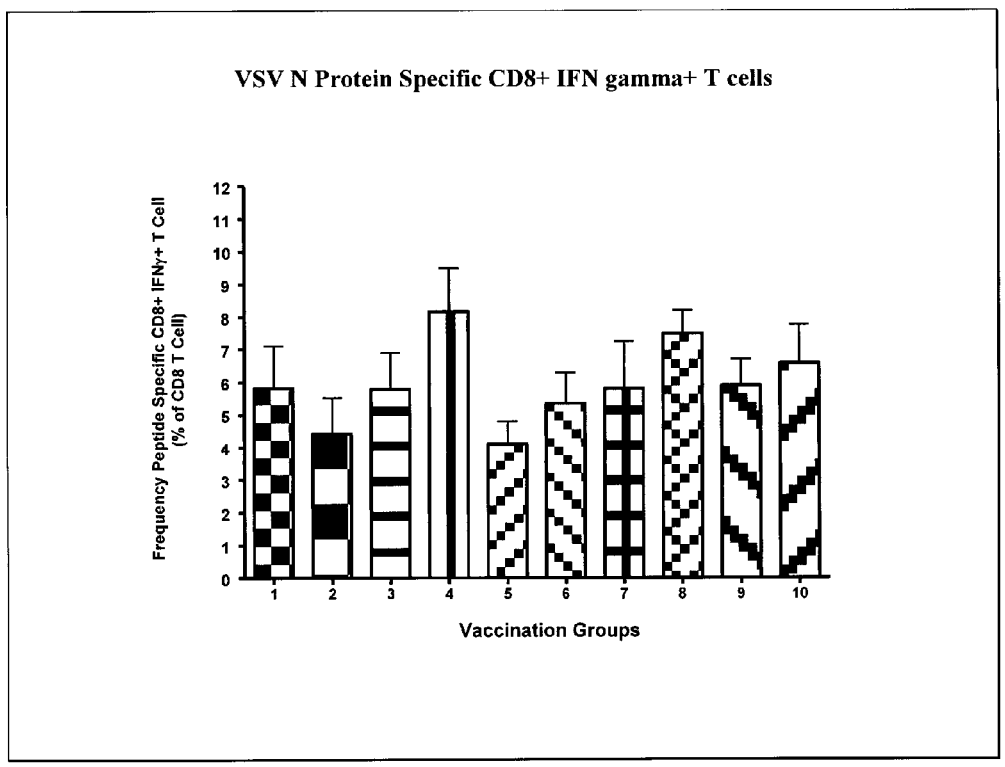
FIG. 19 is a graph illustrating the frequency of VSV N peptide specific CD8+ IFN gamma+ T cells among different vaccination groups vaccinated with various doses of rVSV of Table 1.
Figure 20:
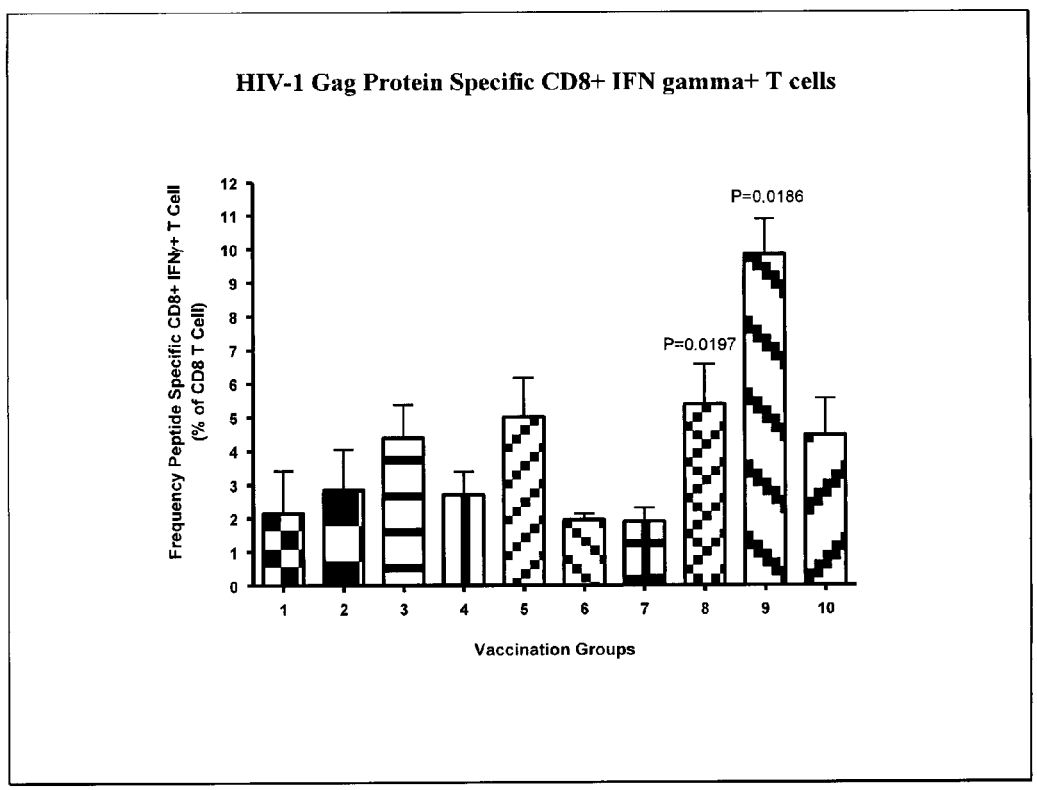
FIG. 20 is a graph illustrating the frequency of HIV-1 Gag peptide specific CD8+ IFN gamma+ T cells among different vaccination groups vaccinated with various doses of rVSV of Table 1.

CD8+ T cell immune responses against VSV N protein were very similar in all vaccination groups with different doses of rVSV$_{Ind}$(GLM)-Gag, rVSV$_{NJ}$(GLM)-Gag, or rVSV$_{NJ}$(GM)-Gag (FIG. 19). The HIV-1 Gag specific CD8+ T cell immune responses after prime vaccination with rVSV$_{Ind}$(GLM)-Gag and booster with rVSV$_{NJ}$(GLM)-Gag looked increased a little bit when the vaccine doses were increased, but differences were not statistically significant (FIG. 20, groups 2, 3, 4, 5). However, when mice were prime vaccinated with rVSV$_{Ind}$(GLM)-Gag and booster vaccinated with rVSV$_{NJ}$(GM)-Gag, the frequency of the HIV-1 Gag specific CD8+ T cells were increased significantly with the increasing dose of 5×10$^8$ PFU. The HIV-1 Gag specific CD8+ T cell response was strongest in a group vaccinated with 5×10$^9$ PFU/mouse (FIG. 20. groups 6, 7, 8, 9). P values on the groups 8 and 9 in FIG. 20 were computed by using two-sided independent sample t test, the result of group 8 was compared to that for the group 7, and the result of group 9 was compared to that for the group 8. The error bars in FIGS. 19 and 20 represent standard error of the mean.

Figure 21:
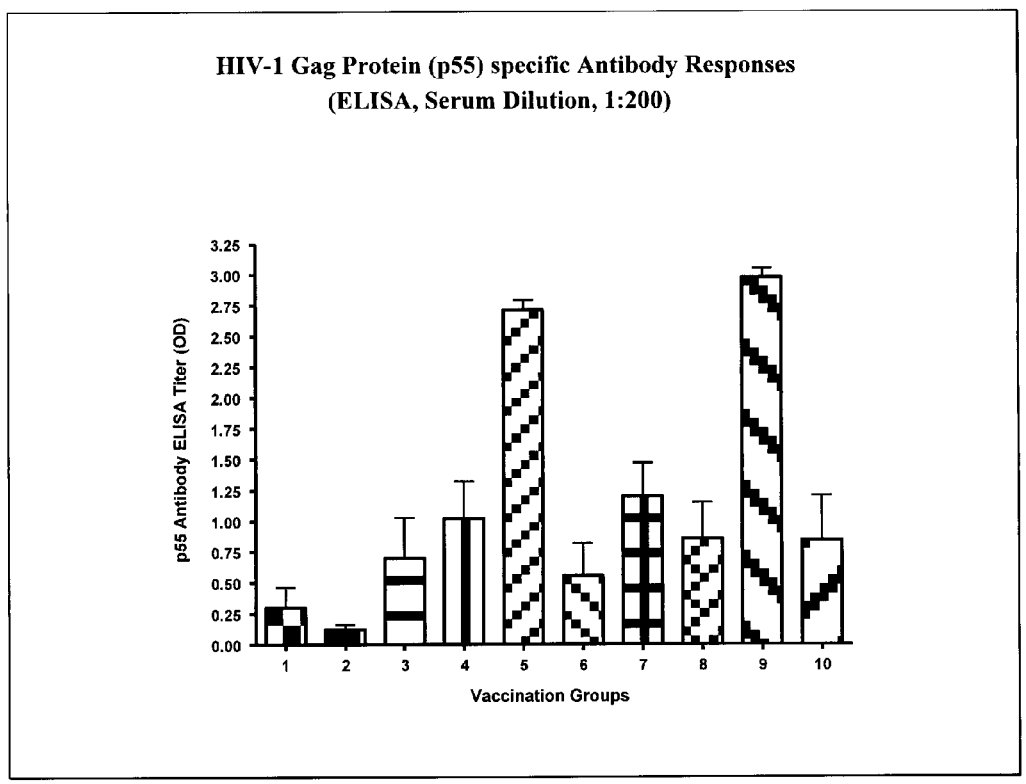
FIG. 21 is a graph illustrating HIV-1 Gag specific antibody responses among different vaccination groups vaccinated with various doses of rVSV of Table 1.

Generation of antibody against HIV-1 Gag protein was increased with the increasing doses of rVSV$_{Ind}$(GLM)-Gag for priming and booster with rVSV$_{NJ}$(GLM)-Gag or rVSV$_{NJ}$(GM)-Gag (FIG. 21). Booster vaccination with rVSV$_{NJ}$(GLM)-Gag or with rVSV$_{NJ}$(GM)-Gag generated similar level of Gag specific antibodies in various doses of the virus. The error bars in FIG. 21 represents standard error of the mean.

Example 13

Figure 22:
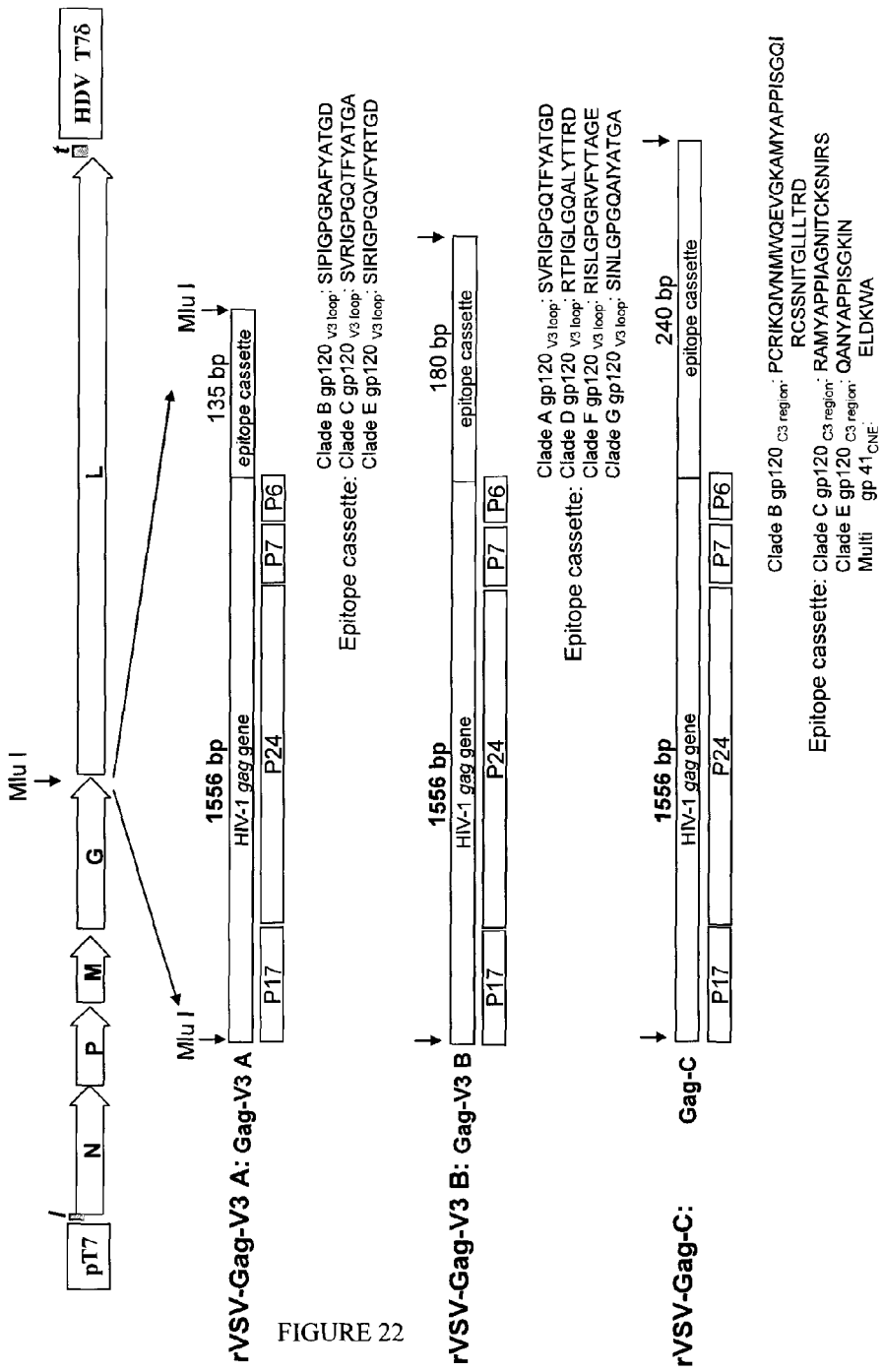
FIG. 22 (SEQ ID NOS: 16-26) illustrates the cloning of HIV-1 gag gene linked to nucleotides encoding human B cell and T cell epitopes of gp120 and gp41 into the cDNA clone of rVSV$_{Ind}$ G21E/L111F/M51R and rVSV$_{NJ}$ G22E/M48R+M51R.
Figure 23:
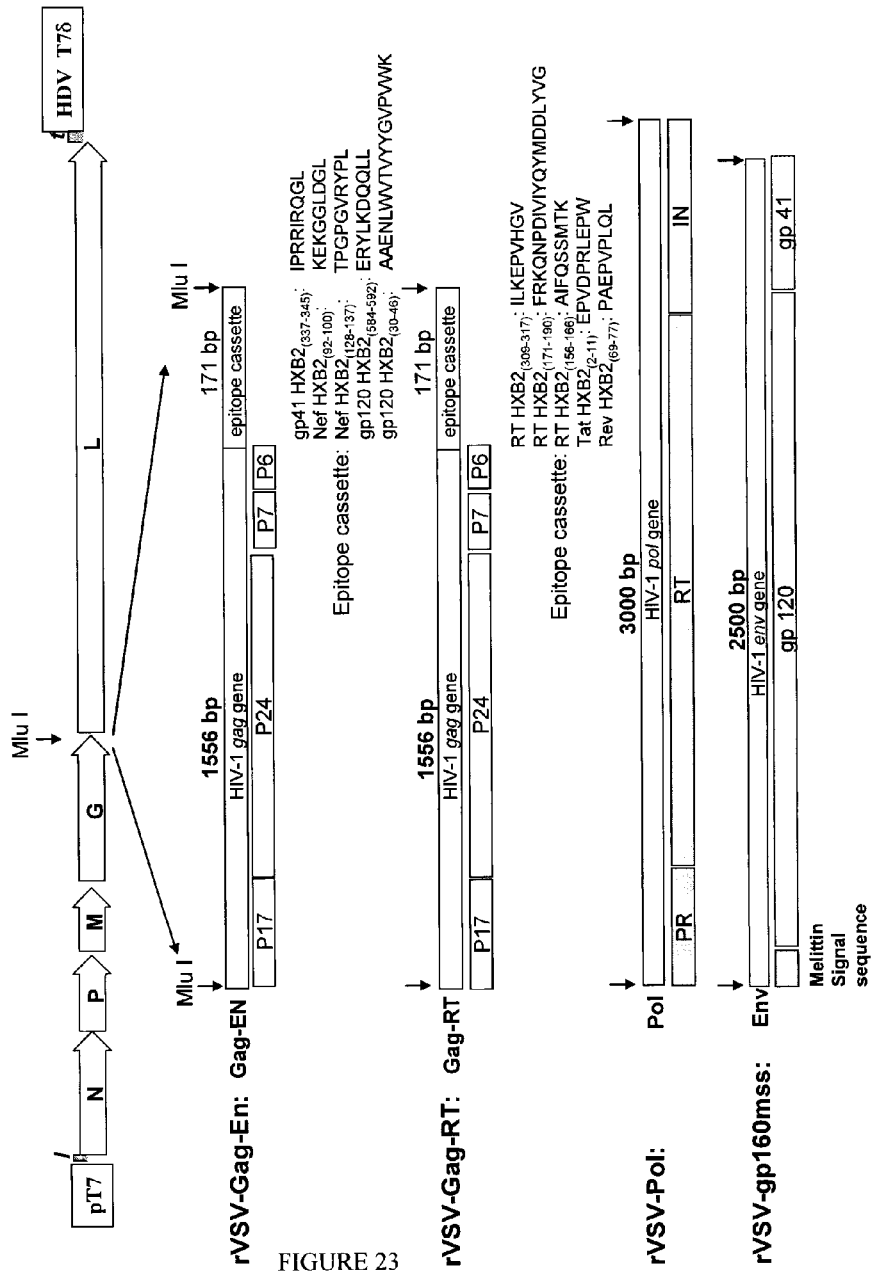
FIG. 23 (SEQ ID NOS: 11-15 and 27-31, respectively) illustrates the cloning of HIV-1 gag gene linked to nucleotides encoding human B cell and T cell epitopes of gp41, nef, gp120, RT, Tat and Rev into the cDNA clone of rVSV$_{Ind}$ G21E/L111F/M51R and rVSV$_{NJ}$ G22E/M48R+M51R. It also illustrates the cloning of HIV-1 pol and env genes into the cDNA clone of rVSV$_{Ind}$ G21E/L111F/M51R and rVSV$_{NJ}$ G22E/M48R+M51R.
Figure 24:
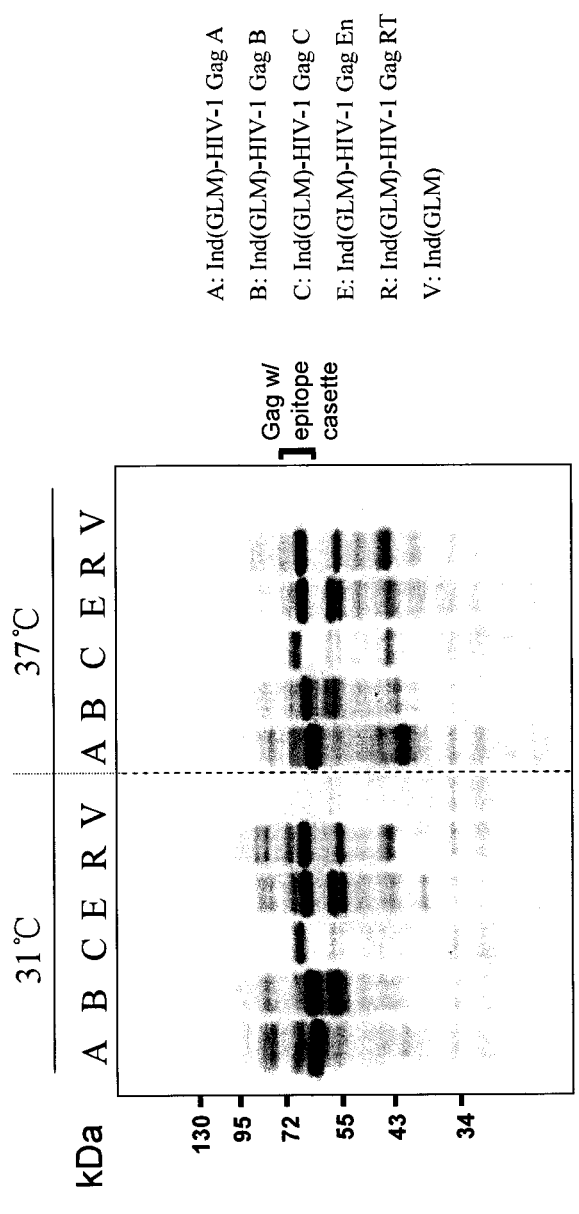
FIG. 24 illustrates a Western blot analysis of BHK21 cells infected with rVSV$_{Ind}$ G21E/L111F/M51R expressing Gag A, B, C, En, and RT and incubated at 31° C. and 37° C.
Figure 26:
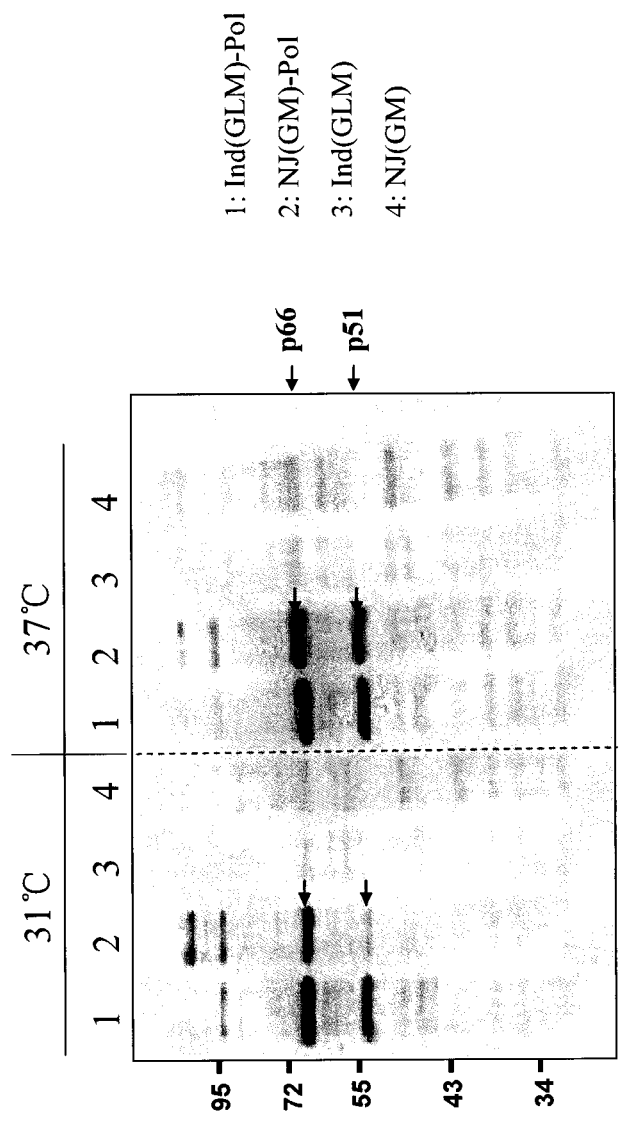
FIG. 26 illustrates a Western blot analysis of BHK21 cells infected with rVSV$_{Ind}$ G21E/L111F/M51R or rVSV$_{NJ}$ G22E/M48R+M51R expressing HIV-1 pol gene.
Figure 27:
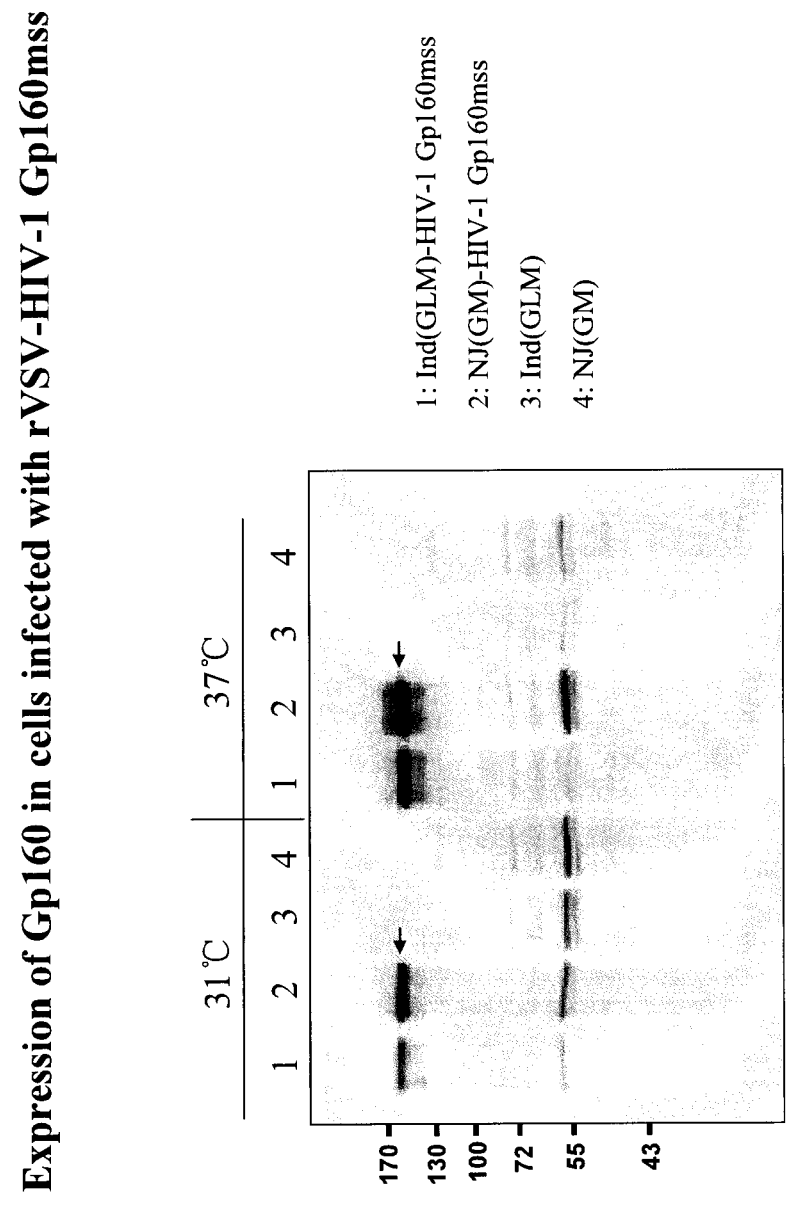

Generation of rVSV$_{Ind}$(GLM) and rVSV$_{NJ}$(GM) Expressing HIV-1 Proteins; Gag, Pol, Env, and RT For HIV-1 vaccines utilizing the rVSV$_{Ind}$(GLM) and rVSV$_{NJ}$(GM) as vaccine vectors, the inventors included HIV genes encoding most of the large polyproteins, which are cleaved into functional proteins-Gag and Env and proteins with enzymatic activities (pol gene products). In addition, HIV-1 gag gene was linked to nucleotides encoding peptide epitopes for T cells and B cells in humans. The inventors have generated rVSV$_{Ind}$(GLM) and rVSV$_{NJ}$(GM) carrying cassettes encoding HIV-1 Gag linked to B-cell epitopes from HIV Env protein derived from multiple viral clades (FIG. 22). The inventors have generated the rVSV$_{Ind}$(GLM)-Gag-En and rVSV$_{NJ}$(GM)-Gag-En, which expresses gag gene and T cell peptide epitopes from Nef, Gp120, and Gp41 (FIG. 23). The inventors generated rVSV$_{Ind}$(GLM) and rVSV$_{NJ}$(GM) with HIV-1 Gag-RT, which encodes gag protein with peptide epitopes from RT, Tat, and Rev proteins (FIG. 23). In addition, the inventors generated rVSV$_{Ind}$(GLM) and rVSV$_{NJ}$(GM) with pol gene and env gene, respectively (FIG. 23). Previously, the inventors have demonstrated that replacement of signal peptide of HIV-1 envelope protein with the honeybee melittin signal peptide dramatically increased the rates of Gp120 expression, glycosylation, and secretion (Yan Li et al., PNAS, 93: 9606-9611, 1996). The increased expression and secretion of Gp120 are expected to enhance the induction of the T cell and B cell immune responses against HIV-1 gp120. Therefore, the inventors generated rVSVs with HIV-1 env gene with melittin signal sequence (gp160mss). The recombinant VSVs with the HIV-1 proteins were plaque purified and were amplified for the stock viruses. The expression of HIV-1 proteins at 31° C. and 37° C. from the mutant VSV was examined by Western blot analysis. The Gag proteins tagged with T cell and B cell epitopes from various HIV-1 proteins were expressed well from rVSV$_{Ind}$(GLM) and rVSV$_{NJ}$(GM) at both 31° C. and 37° C. (FIG. 24 and FIG. 25). The cloned HIV-1 pol gene in the rVSV genome encodes a polyprotein, which is cleaved into protease (PR, p11), reverse transcriptase (RT, p66p51), and integrase (IN, p31). The inventors detected two subunits of RT products, p66 and p51. The p51 is generated from the p66 by proteolytic cleavage of a fragment of p15 at the carboxy terminus. The RT products p66 and p51 were expressed equally well from both rVSV$_{Ind}$(GLM) and rVSV$_{NJ}$(GM) and at both 31° C. and 37° C. (FIG. 26). The env gene encodes glycoprotein Gp160, which is cleaved into Gp120 of receptor binding protein and gp41 of fusion inducing cytoplasmic and transmembrane protein. Gp160 is cleaved by the cellular trans-golgi resident protease Turin. The Gp160 expressed in BHK21 cells from the rVSV$_{Ind}$(GLM) and rVSV$_{NJ}$(GM) was not cleaved to Gp120 and Gp41 or the cleavage was not very efficient, although the level of expression was good at both 31° C. and 37° C. (FIG. 27). Our previous data on the expression of the Gp160 in BHK21 cells and cleavage into Gp120 and Gp41 demonstrated that the processing was not very efficient (Kunyu Wu et al., Journal of General Virol., 90:1135-1140, 2009).

Example 14

Immunization Studies in Mice with the rVSV$_{Ind}$(GLM) and rVSV$_{NJ}$(GM) with HIV-1 Proteins, Gag, Gp160 and RT The preliminary prime-boost immunization studies with new M mutant rVSVs, rVSV$_{Ind}$(GLM) and rVSV$_{NJ}$(GM) revealed that priming mice with the rVSV$_{Ind}$(GLM) and boosting with rVSV$_{NJ}$(GM) induced better CD8+ T cell immune response (FIG. 17) and humoral immune responses (FIG. 18) against the foreign gene than the other way around. With the rVSV$_{Ind}$(GLM)-Gag priming and rVSV$_{NJ}$ (GM)-Gag boosting, the dosage of 5×10$^8$ pfu of each virus induced better Gag specific CD8+ T cell responses than lower dosages, although the B cell responses against Gag was similar to that induced with the lower dosages (FIG. 20 and FIG. 21). The inventors chose 5×10$^8$ pfu as a dosage for immunization studies with rVSV$_{Ind}$(GLM) and rVSV$_{NJ}$(GM) expressing HIV-1 Gag, Gp160, and RT.

Figure 28:
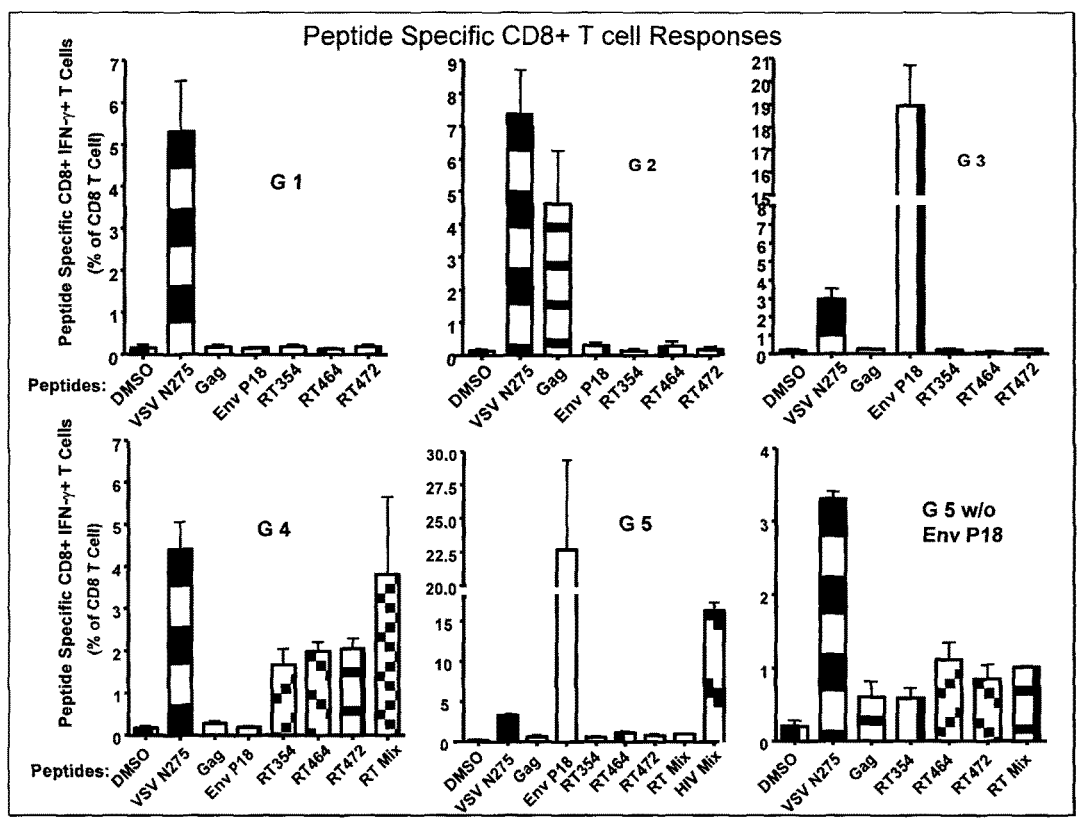
FIG. 28 includes graphs illustrating VSV N and HIV-1 protein peptide specific CD8+ T cell responses among the different vaccination groups of Table 6: G1, G2, G3, G4, 35 and G5 without Env P18.
Figure 29:
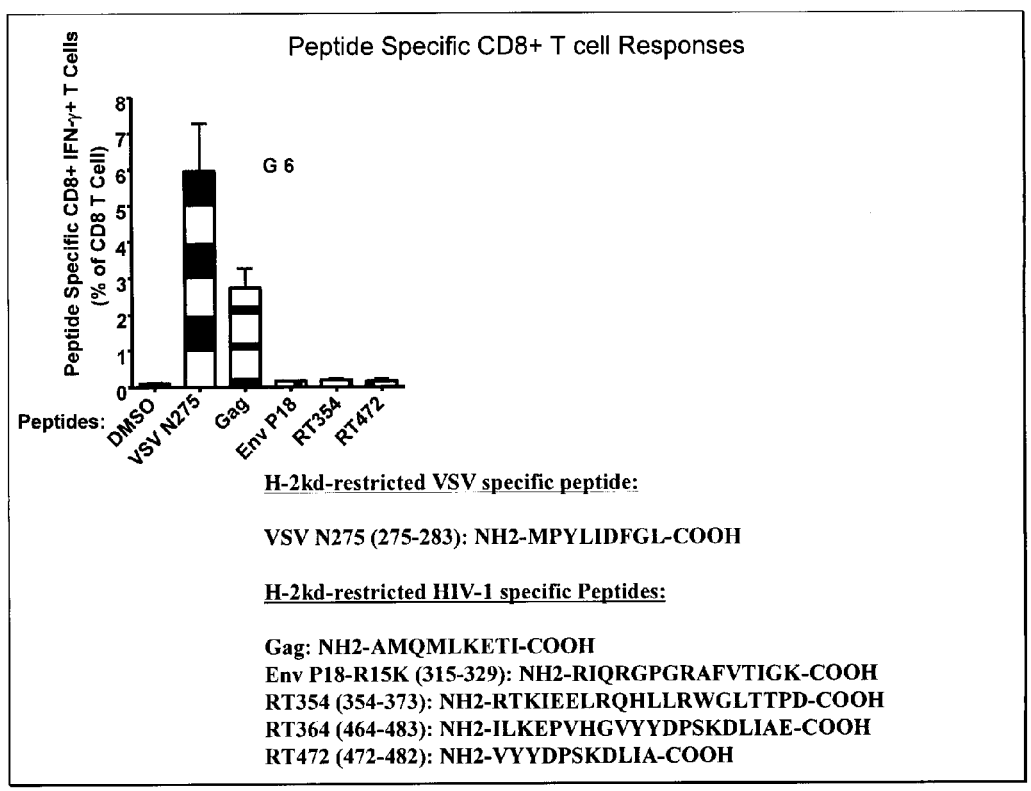
FIG. 29 is a graph illustrating VSV N and HIV-1 protein peptide specific CD8+ T cell responses in vaccination group G6 of Table 6. The amino acid sequences of VSV N peptide and peptides from HIV-1 proteins that are used to stimulated the splenocytes are shown (SEQ ID NOS: 32-37).

The inventors prime immunized Balb/c mice with rVSV$_{Ind}$(GLM) expressing HIV-1 proteins and boost immunized with rVSV$_{NJ}$(GM) expressing HIV-1 proteins in three weeks after the priming as described in the table 6. The inventors examined how the immune responses against the individual HIV-1 proteins are induced with individual injection or with the mixed injection of three different viruses expressing separate proteins. One week after the boost immunization, the inventors sacrificed the immunized mice for their splenocytes and sera. The 1×10$^6$ splenocytes were stimulated with H-2K$^d$-restricted HIV-1 protein specific peptides, which are Gag, Env P18, RT354, RT464, and RT472. The peptide sequences are shown in the FIG. 29. The stimulated splenocytes were double stained for the cell surface CD8 molecules and intracellular IFN-γ of T cells with FITC rat anti-mouse CD8 and APC rat anti-mouse IFN-γ. The regimen, prime-boost immunization with rVSV$_{Ind}$(GLM) and rVSV$_{NJ}$(GM) induced peptide specific CD8+ T cell immune responses with different degree depending on the peptides the inventors used for the stimulation. CD8+ T cells against Env peptide stimulated CD8+ T cells the most up to 19%-23% of CD8+ T cells on average (FIG. 28, G3 and G5). About 4.5% or 3% of CD8+ T cells were responsive to the Gag protein in mice immunized with rVSV expressing Gag alone (FIG. 28, G2) or with mixed three rVSVs expressing Gag A, Gag B, and Gag C linked with various B and T cell epitopes of HIV-1 Gp120 and Gp41 (FIG. 29, G6). RT specific CD8+ T cells were generated in about 2% of CD8+ T cells in mice injected with rVSV with pol gene (FIG. 28, G4). CD8+ T cell responses against individual HIV-1 protein, Gag and RT were stronger when mice were injected with single rVSV expressing individual protein (FIG. 28, G2 and G4) than when injected with mixed rVSVs expressing single protein (FIG. 28, G5). Env specific CD8+ T cell responses were strongest and were similar in both single injection and mixed injections. The CD8+ T cells responses against Env peptide epitope are immunodominant in Balb/c mice. Currently, the inventors are uncertain why mixed injections with three different rVSVs expressing Gag, Env, and RT induced comparatively lower CD8+ T cell responses against VSV N, gag, and RT than with the single virus injection. It is possible that the competition of each virus for the antigen presenting cells in the mixed virus injection lowered the CD8+ T cells against Gag and RT. Because rVSV is common vector for HIV-1 proteins in mice either injected with single rVSV or mixed rVSVs, VSV N supposed to induce similar or better CD8+ T cell responses in the mixed injection. However, the CD8+ T cell responses against VSV N in mice are lower even with the single injections when the Env is expressed (FIG. 28, G3) as in the mixed injection (FIG. 28, G5). Therefore, it may be the result of immune dominance of Env protein in Balb/c mice, which affects negatively to the presentation of other proteins to the CD8+ T cells when Env is expressed together. For the combined immunizations in mice, all three rVSVs were injected at the single site, which may have resulted in the competition of different proteins for the antigen presentation in the same antigen presentation cells. The inventors will test the immunization with the mixed injections at more than one injection sites to induce CD8+ T cell responses.

Figure 30:
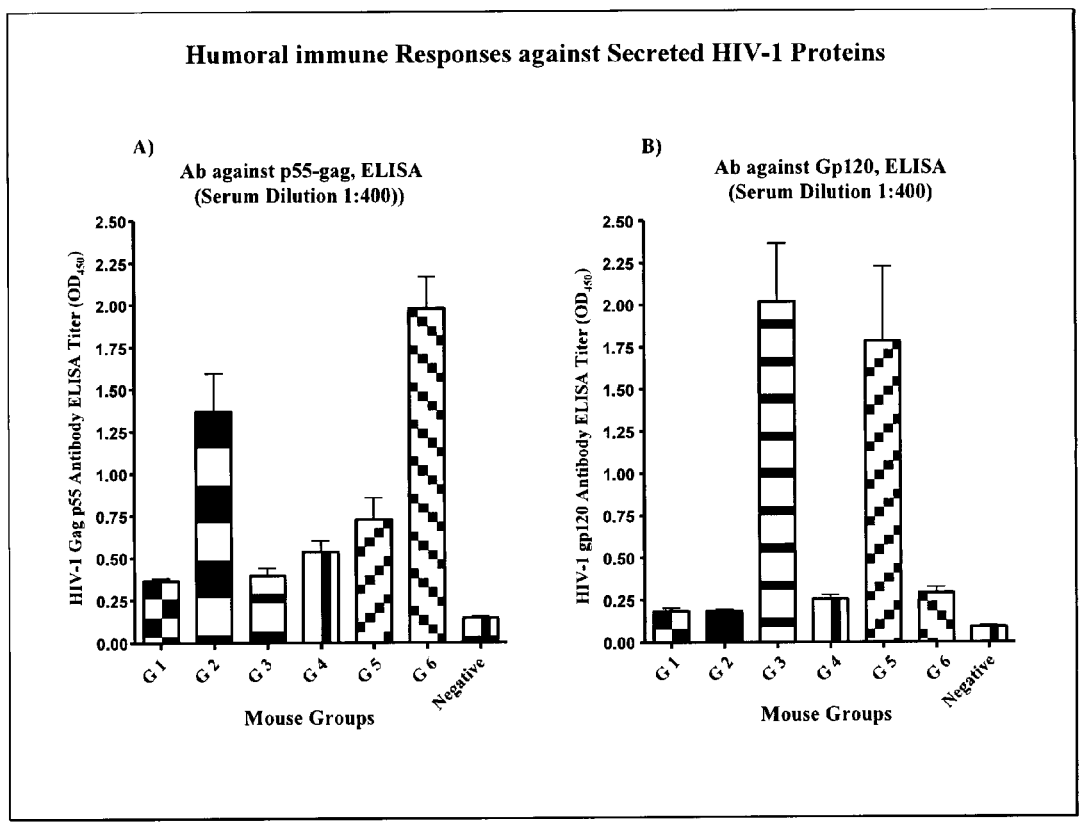
FIG. 30 illustrates the humoral immune responses against HIV-1 Gag (panel A) and Gp120 (panel B) induced in vaccination groups of Table 6, which were determined by Enzyme Linked Immunosorbant Assay (ELISA).

HIV-1 Gag proteins expressed in cells can form virus like particles (VLP) and the VLP can be released from the cells. The released VLPs can induce humoral immune responses against Gag proteins. HIV-1 env gene encodes glycosylated surface proteins, which are processed through ER-golgi network to be properly folded and cleaved into transmembrane subunit Gp41 and surface unit Gp120. The Gp41 and Gp120 are associated by non-covalent bond and mature to form a trimer of Gp41 and Gp120 heterodimer. The matured trimer of Gp41 and Gp120 are exported to the cell surface. The Gp120 tends to fall off from the cell surface because of the weak bondage between Gp41 and Gp120. Therefore, antibody against Gp120 can be induced to the cell surface Gp120 or fallen off Gp120. Antibody titer against HIV-1 Gag protein and Gp120 was determined by ELISA. For the Gag antibody the microplate was coated with 125 ng/well of recombinant p55 (Pierce Biotechnology, RP-4921) and 50 µl of mice sera was tested with the dilution of 1:100, 1:200, and 1:400. Gag antibody was produced in mice injected with rVSV Gag-En alone (FIG. 30A, G2) and with mixed viruses rVSV-Gag A+rVSV Gag B+rVSV Gag C (FIG. 30A, G6). For the Gp120 ELISA, 96 well microplate was coated with 250 ng/well of HIV-1 SF162 Gp140 trimer from clade B (NIH AIDS reagent program, cat#12026). Mice sera were diluted in 1:100, 1:200, and 1:400 and 50 µl of the diluted serum was added to the microplate for the ELISA. Antibody specific to Gp120 was generated in mice injected with rVSV-HIV-1 Gp160 alone and in mice injected with the mixed viruses expressing each protein of Gag, Gp160, and RT (FIG. 30B, G3 and G5). The titer of Gp120 antibody was slightly lower, although not statistically significant, in mice injected with mixed viruses than in mice injected with single virus expressing Gp160.

The newly generated M mutants of rVSVs, rVSV$_{Ind}$ (GLM) and rVSV$_{NJ}$(GM) induced CD8+ T cell and humoral immune responses against various HIV-1 proteins expressed from the vector after injecting mice with an individual virus expressing single virus or with mixed viruses expressing various HIV-1 proteins.

Example 15

Generation of rVSV$_{Ind}$(GLM), rVSV$_{NJ}$(GM), and rVSV$_{NJ}$(GLM) with Hepatitis C Virus Structural Proteins Generally, the humoral immune response is the first line of defense mediated by adaptive immune responses against any pathogens. Although humoral immune responses against HCV and its role in the prevention of HCV infection is not well studied compared to the I-ICY specific cellular immune responses, it is worthy to include vaccines which can induce HCV specific antibodies. It has been demonstrated that nucleocapsid protein core and surface glycoproteins E1 and E2 form virus-like particles (VLP) which can be released from the cells (Blanchard, E. et al., J. Virol. 76:4073-4079, 2002). In addition, it has been demonstrated that HCV protein p7, a viroporin forming an ion channel in the ER membrane, takes part in releasing the HCV particles from the infected cell (Steinmann, E. et al., PLoS Pathogens 3:962-972, 2007). Another HCV transmembrane protein NS4B forms a membranous web structure, which mainly consists of the ER membrane. The membranous web formed by NS4B is a microstructure for the production of progeny HCV. It is not well known what functions NS4B has in the replication of HCV, but it is appealing to include NS4B into vaccine candidates simply because of its nature forming a membranous structure of ER in which other HCV proteins, especially Core, E1, E2, p7 are localized. Therefore, including Core, E1, E2, P7, and NS4B together into the vaccine may induce humoral and cellular immune responses.

Figure 31:
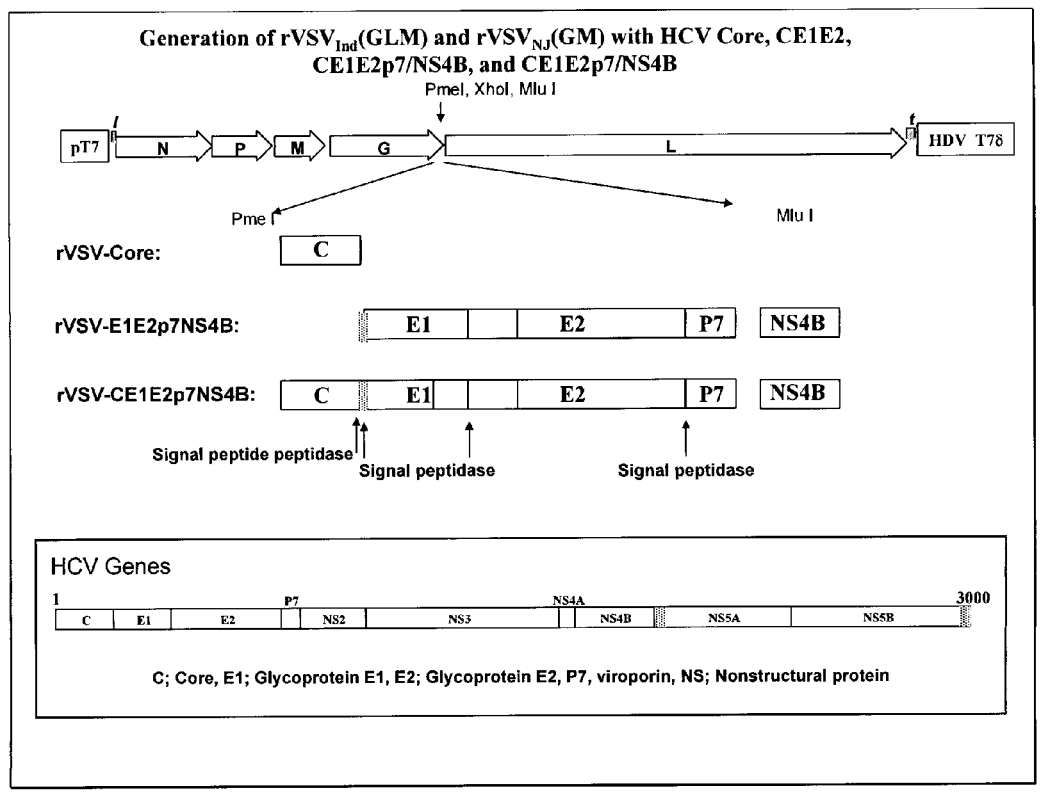
FIG. 31 depicts the HCV structural protein genes cloned into rVSV$_{Ind}$(GLM) and rVSV$_{NJ}$(GM) and rVSV$_{NJ}$(GLM).
Figure 32:
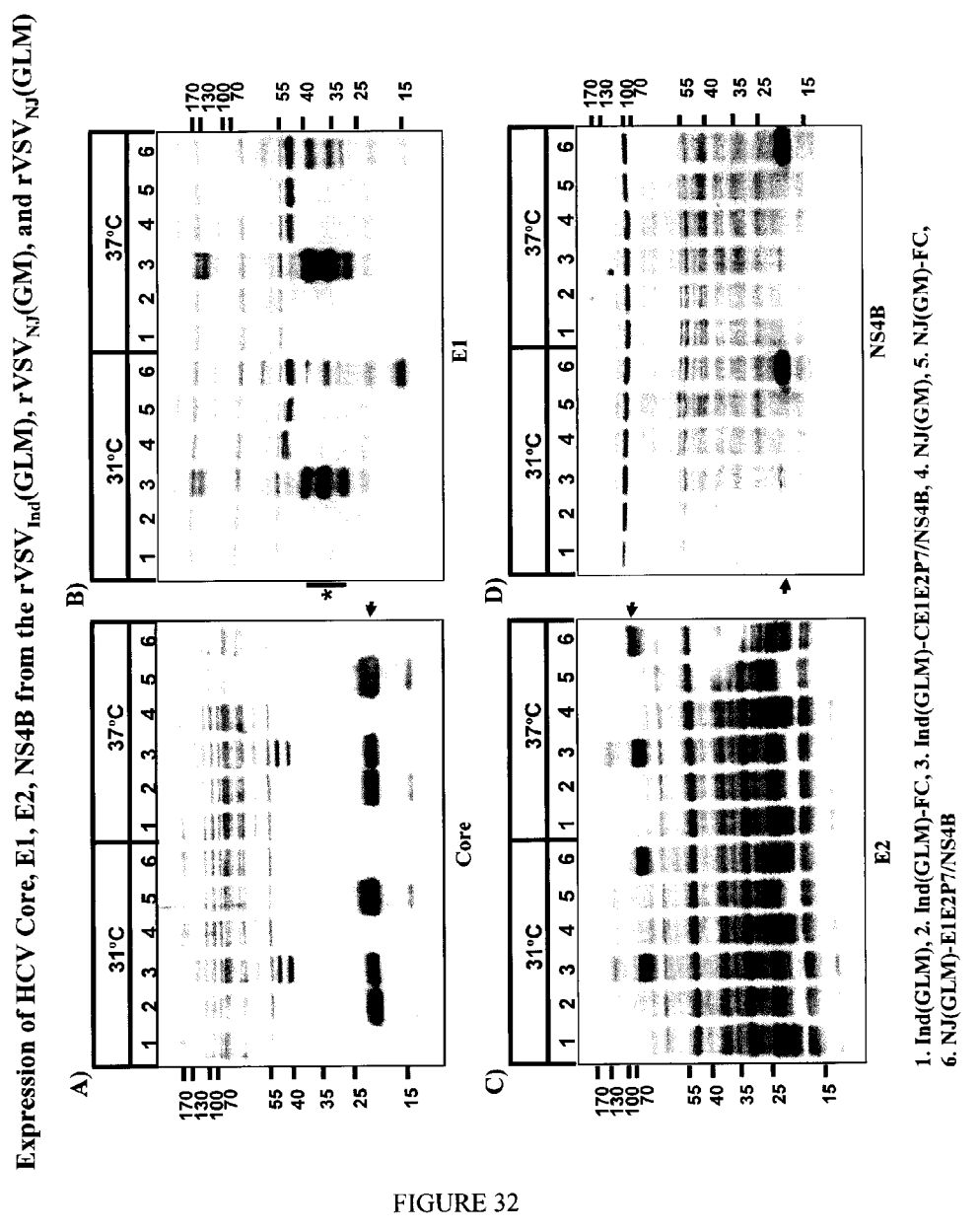

For the HCV structural protein vaccines using the new M mutant rVSVs, the inventors inserted the HCV core gene, E1E2P7 and NS4B genes together (connected by the VSV intergenic junction sequences), and CoreE1E2P7 and NS4B genes together (connected by the VSV intergenic junction sequences) to the junction of VSV G gene and L (FIG. 31). The rVSVs; rVSV$_{Ind}$(GLM)-FC, rVSV$_{Ind}$(GLM)-CE1E2P7/NS4B, rVSV$_{NJ}$(GM)-FC, and rVSV$_{NJ}$(GLM)-E1E2P7/NS4B were generated by reverse genetics. The inventors had a trouble to generate the rVSV$_{NJ}$(GM) with CE1E2P7/NS4B from the plasmid DNA, therefore, the inventors removed the core and cloned E1E2P7/NS4B into the plasmid of rVSV$_{NJ}$(GLM) and generated the rVSV$_{NJ}$(GLM)-E1E2P7/NS4B. The expression of Core, E1, E2, and NS4B from the recombinant VSV at 31° C. and 37° C. was examined by Western blot analysis using antibodies against each protein (FIG. 32). The proteins were expressed similarly in quantity at both temperatures. Core (FIG. 32A), E1 (FIG. 32B), and E2 FIG. 32C) were expressed well from the rVSV$_{Ind}$(GLM)-CE1E2P7/NS4B, but the expression of NB4B was lower than the other proteins (FIG. 32D).

Example 16

Generation of rVSV$_{Ind}$(GLM), rVSV$_{NJ}$(GM), and rVSV$_{NJ}$(GLM) with HCV Non-Structural Proteins The inventors want to target most of the HCV proteins including core, E1, E2, NS3, NS4A, NS4B, NS5A and NS5B proteins in order to induce HCV specific CD8+ T cell and CD4+ T cell immune responses to multiple proteins. HCV nonstructural (NS) proteins-NS3, NS4A, NS4B, NS5A, and NS5B cover more than half of the HCV polyprotein. The NS proteins are cleaved into individual proteins by NS3 with the help of NS4A. Several studies demonstrate that patients who recover from the acute HCV infection developed strong CD4+ T cell and CD8+ T cell responses against multiple epitopes in the NS3 protein (Diepolder, H. M. J. Virol. 71:6011-6019, 1997; Lamonaca, V. et al. Hepatology 30:1088-1098, 1999; Shoukry, N. H. et al. J. Immunol. 172:483-492, 2004) indicating that including NS3 in the vaccine candidate is important to elicit successful cellular immune responses against HCV. NS3 protein, a serine protease and RNA helicase associates with NS4A and resides on the ER membrane (Sato, S. et al. J. Virol. 69:4255-4260, 1995; Failla, C. et al. J. Virol. 69:1769-1777, 1995). NS5A protein, a phosphoprotein is believed to be involved in HCV RNA synthesis together with NS5B protein, a RNA dependent RNA polymerase (Shirota, Y. et al., J. Biol. Chem., 277:11149-11155, 2002; Shimakami, et al. J. Virol. 78:2738-2748, 2004). NS5B protein is a RNA dependent RNA polymerase that synthesizes positive sense HCV genomic RNA as well as intermediate negative sense genomic RNA (Beherens, S. E. EMBO J. 15:12-22, 1996). NS5B protein is a tail-anchored protein and associates with ER membrane through its carboxyl terminal 20 amino acids (Yamashita, T. J. Biol. Chem. 273:15479-15486, 1998; Hagedorn, C. H. Curt Top. Microbiol. Immunol. 242:225-260, 2000).

Figure 34:
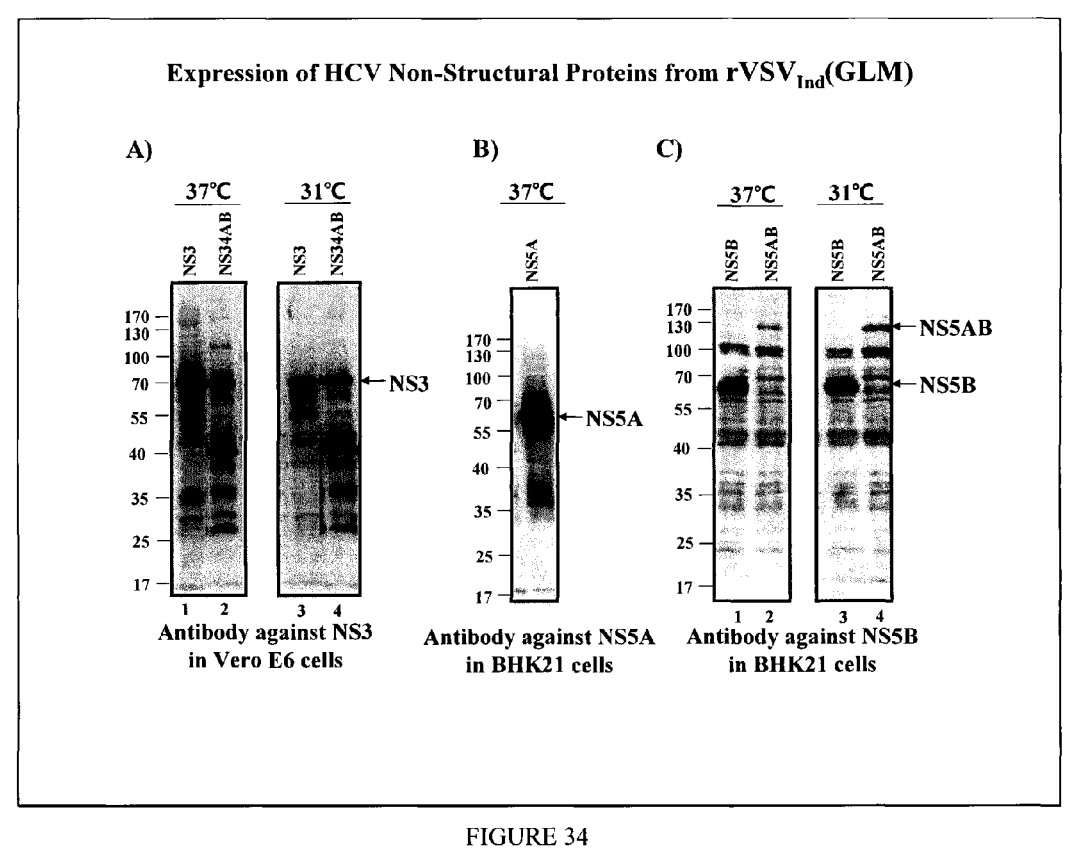
Figure 35:
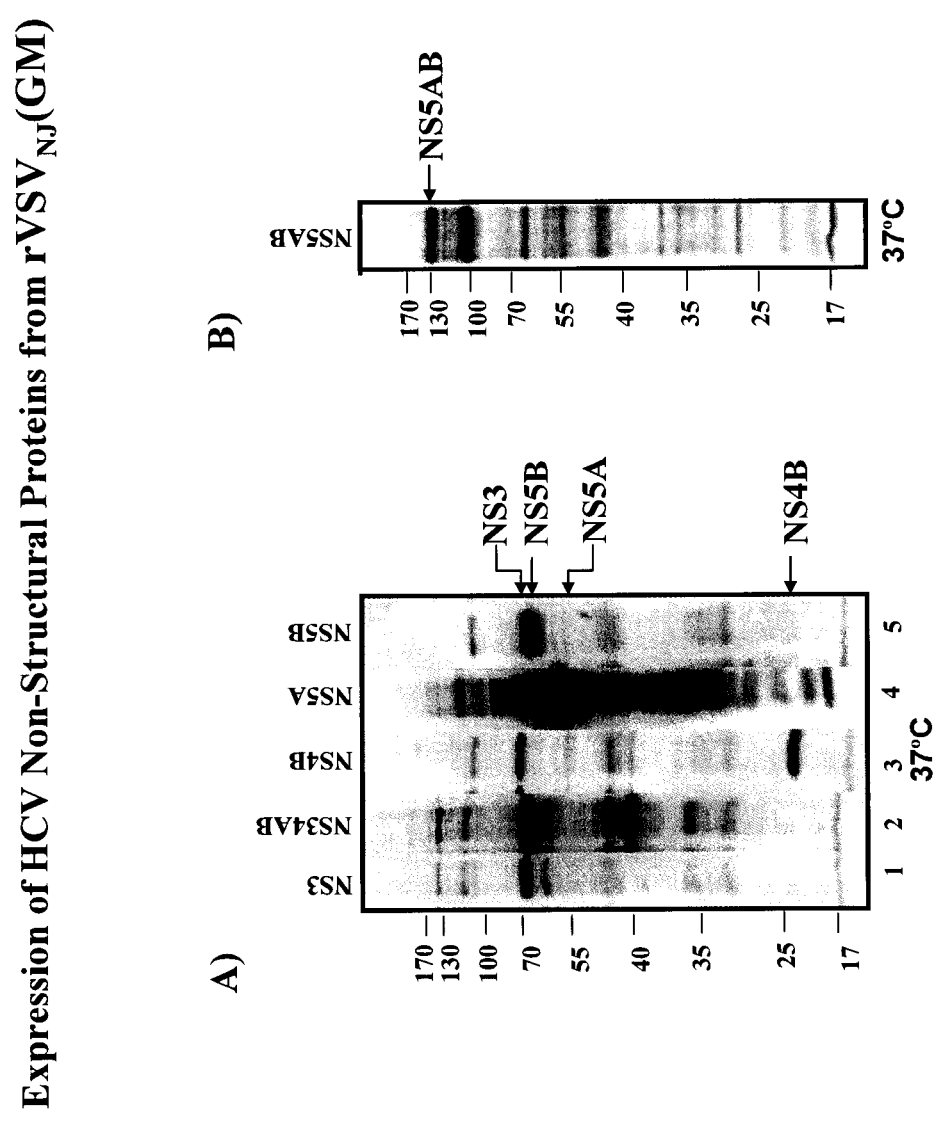

The inventors cloned HCV NS genes as a gene for a single protein or a gene for a polyprotein of 2 or 3 NS proteins. The NS genes NS3, NS34AB, NS5A, NS5B, NS5AB were cloned into the junction at G gene and L gene of pVSV$_{Ind}$ (GLM) and pVSV$_{NJ}$(GM) (FIG. 33). The inventors generated rVSV$_{Ind}$(GLM)-NS3, rVSV$_{Ind}$(GLM)-NS34AB, rVSV$_{Ind}$(GLM)-NS5A, rVSV$_{Ind}$(GLM)-NS5B, and rVSV$_{Ind}$(GLM)-NS5AB, and the expression of the NS proteins at 31° C. and 37° C. were determined by Western blot analysis using antibodies against each NS protein (FIG. 34). The inventors generated rVSV$_{NJ}$(GM)-NS3, rVSV$_{NJ}$(GM)-NS4B, rVSV$_{NJ}$(GM)-NS34AB, rVSV$_{NJ}$(GM)-NS5A, rVSV$_{NJ}$(GM)-NS5B, and rVSV$_{NJ}$(GM)-NS5AB. The expression of each protein from the rVSV$_{NJ}$ vector at 37° C. was examined by Western blot analysis using antibodies against each NS protein (FIG. 35). Although the expression level of NS proteins from the rVSV$_{Ind}$ and rVSV$_{NJ}$ was different, it was good enough to use them as HCV vaccine.

TABLE 1

Mouse Vaccination Groups and Regimen

| Vaccination Groups | Prime | | Boost | | |
|---|---|---|---|---|---|
| | Viruses | Titer (PFU)/50 µl | Viruses | Titer (PFU)/50 µl | # of Mice |
| 1 | Ind (WT)-Gag | $5 \times 10^6$ | NJ (WT)-Gag | $5 \times 10^6$ | 6 |
| 2 | Ind (GLM)-Gag | $5 \times 10^6$ | NJ (GLM)-Gag | $5 \times 10^6$ | 6 |
| 3 | Ind (GLM)-Gag | $5 \times 10^7$ | NJ (GLM)-Gag | $5 \times 10^7$ | 6 |
| 4 | Ind (GLM)-Gag | $5 \times 10^8$ | NJ (GLM)-Gag | $5 \times 10^8$ | 6 |
| 5 | Ind (GLM)-Gag | $5 \times 10^9$ | NJ (GLM)-Gag | $5 \times 10^9$ | 6 |
| 6 | Ind (GLM)-Gag | $5 \times 10^6$ | NJ (GM)-Gag | $5 \times 10^6$ | 6 |
| 7 | Ind (GLM)-Gag | $5 \times 10^7$ | NJ (GM)-Gag | $5 \times 10^7$ | 6 |
| 8 | Ind (GLM)-Gag | $5 \times 10^8$ | NJ (GM)-Gag | $5 \times 10^8$ | 6 |

TABLE 1-continued

Mouse Vaccination Groups and Regimen

| Vaccination Groups | Prime | | Boost | | # of Mice |
|---|---|---|---|---|---|
| | Viruses | Titer (PFU)/50 μl | Viruses | Titer (PFU)/50 μl | |
| 9 | Ind (GLM)-Gag | $5 \times 10^9$ | NJ (GM)-Gag | $5 \times 10^9$ | 6 |
| 10 | NJ (WT)-Gag | $5 \times 10^6$ | Ind (WT)-Gag | $5 \times 10^6$ | 6 |
| Total Mice | | | | | 60 |

TABLE 2

Neucleotide Sequence Comparison between M Genes of VSV Indiana serotype, Wild Type (SEQ ID NO: 1) and a Mutant G21E/L111E/M51R (SEQ ID NO 2)

```
                  1                                                  50
SEQ ID NO: 1: ATGAGTTCCT TAAAGAAGAT TCTCGGTCTG AAGGGGAAAG GTAAGAAATC
SEQ ID NO: 2: ATGAGTTCCT TAAAGAAGAT TCTCGGTCTG AAGGGGAAAG GTAAGAAATC 51                                                 100
SEQ ID NO: 1: TAAGAAATTA GGGATCGCAC CACCCCCTTA TGAAGAGGAC ACTAACATGG
SEQ ID NO: 2: TAAGAAATTA GAAATCGCAC CACCCCCTTA TGAAGAGGAC ACTAACATGG 101                                                 150
SEQ ID NO: 1: AGTATGCTCC GAGCGCTCCA ATTGACAAAT CCTATTTTGG AGTTGACGAG
SEQ ID NO: 2: AGTATGCTCC GAGCGCTCCA ATTGACAAAT CCTATTTTGG AGTTGACGAG 151                                                 200
SEQ ID NO: 1: ATGGACACTC ATGATCCGCA TCAATTAAGA TATGAGAAAT TCTTCTTTAC
SEQ ID NO: 2: AGGGACACTC ATGATCCGCA TCAATTAAGA TATGAGAAAT TCTTCTTTAC 201                                                 250
SEQ ID NO: 1: AGTGAAAATG ACGGTTAGAT CTAATCGTCC GTTCAGAACA TACTCAGATG
SEQ ID NO: 2: AGTGAAAATG ACGGTTAGAT CTAATCGTCC GTTCAGAACA TACTCAGATG 251                                                 300
SEQ ID NO: 1: TGGCAGCCGC TGTATCCCAT TGGGATCACA TGTACATCGG AATGGCAGGG
SEQ ID NO: 2: TGGCAGCCGC TGTATCCCAT TGGGATCACA TGTACATCGG AATGGCAGGG 301                                                 350
SEQ ID NO: 1: AAACGTCCCT TCTACAAGAT CTTGGCTTTT TTGGGTTCTT CTAATCTAAA
SEQ ID NO: 2: AAACGTCCCT TCTACAAGAT CTTGGCTTTT TTTGGTTCTT CTAATCTAAA 351                                                 400
SEQ ID NO: 1: GGCCACTCCA GCGGTATTGG CAGATCAAGG TCAACCAGAG TATCACGCTC
SEQ ID NO: 2: GGCCACTCCA GCGGTATTGG CAGATCAAGG TCAACCAGAG TATCACGCTC 401                                                 450
SEQ ID NO: 1: ACTGTGAAGG CAGGGCTTAT TTGCCACACA GAATGGGGAA GACCCCTCCC
SEQ ID NO: 2: ACTGTGAAGG CAGGGCTTAT TTGCCACACA GAATGGGGAA GACCCCTCCC 451                                                 500
SEQ ID NO: 1: ATGCTCAATG TACCAGAGCA CTTCAGAAGA CCATTCAATA TAGGTCTTTA
SEQ ID NO: 2: ATGCTCAATG TACCAGAGCA CTTCAGAAGA CCATTCAATA TAGGTCTTTA 501                                                 550
SEQ ID NO: 1: CAAGGGAACG GTTGAGCTCA CAATGACCAT CTACGATGAT GAGTCACTGG
SEQ ID NO: 2: CAAGGGAACG GTTGAGCTCA CAATGACCAT CTACGATGAT GAGTCACTGG 551                                                 600
SEQ ID NO: 1: AAGCAGCTCC TATGATCTGG GATCATTTCA ATTCTTCCAA ATTTTCTGAT
SEQ ID NO: 2: AAGCAGCTCC TATGATCTGG GATCATTTCA ATTCTTCCAA ATTTTCTGAT 601                                                 650
SEQ ID NO: 1: TTCAGAGATA AGGCCTTAAT GTTTGGCCTG ATTGTCGAGA AAAAGGCATC
SEQ ID NO: 2: TTCAGAGATA AGGCCTTAAT GTTTGGCCTG ATTGTCGAGA AAAAGGCATC 651                                                 700
SEQ ID NO: 1: TGGAGCTTGG GTCCTGGATT CTGTCAGCCA CTTCAAATGA
SEQ ID NO: 2: TGGAGCTTGG GTCCTGGATT CTGTCAGCCA CTTCAAATGA
```

TABLE 3

Amino Acid Sequence Comparison between M Proteins of VSV Indiana serotype Wild Type (SEQ ID NO: 3) and a Mutant G21E/L111F/M51R (SEQ ID NO: 4)

```
                 1                    21                                50
SEQ ID NO: 3:MSSLKKILGL KGKGKKSKKL GIAPPPYEED TNMEYAPSAP IDKSYFGVDE
SEQ ID NO: 4:MSSLKKILGL KGKGKKSKKL EIAPPPYEED TNMEYAPSAP IDKSYFGVDE 51                                                   100
SEQ ID NO: 3:MDTHDPHQLR YEKFFFTVKM TVRSNRPFRT YSDVAAAVSH WDHMYIGMAG
SEQ ID NO: 4:RDTHDPHQLR YEKFFFTVKM TVRSNRPFRT YSDVAAAVSH WDHMYIGMAG 101      111                                         150
SEQ ID NO: 3:KRPFYKILAF LGSSNLKATP AVLADQGQPE YHAHCEGRAY LPHRMGKTPP
SEQ ID NO: 4:KRPFYKILAF FGSSNLKATP AVLADQGQPE YHAHCEGRAY LPHRMGKTPP 151                                                  200
SEQ ID NO: 3:MLNVPEHFRR PFNIGLYKGT VELTMTIYDD ESLEAAPMIW DHFNSSKFSD
SEQ ID NO: 4:MLNVPEHFRR PFNIGLYKGT VELTMTIYDD ESLEAAPMIW DHFNSSKFSD 201                   229                            250
SEQ ID NO: 3:FRDKALMFGL IVEKKASGAW VLDSVSHFK
SEQ ID NO: 4:FRDKALMFGL IVEKKASGAW VLDSVSHFK
```

TABLE 4

Nucleotide Sequence Comparison between M Genes of VSV New Jersey serotype Wild Type (SEQ ID NO: 5) and Mutants, G22E/M48R + M51R (SEQ ID NO: 6) and G22E/L110F/M48R + M51R (SEQ ID NO: 7)

```
                 1                                                    50
SEQ ID NO: 5:ATGAGTTCCT TCAAAAAGAT TCTGGGATTT TCTTCAAAAA GTCACAAGAA
SEQ ID NO: 6:ATGAGTTCCT TCAAAAAGAT TCTGGGATTT TCTTCAAAAA GTCACAAGAA
   ID NO: 7: ATGAGTTCCT TCAAAAAGAT TCTGGGATTT TCTTCAAAAA GTCACAAGAA 51                                                   100
SEQ ID NO: 5:ATCAAAGAAA CTAGGCTTGC CACCTCCTTA TGAGGAATCA AGTCCTATGG
SEQ ID NO: 6:ATCAAAGAAA CTAGAATTGC CACCTCCTTA TGAGGAATCA AGTCCTATGG
SEQ ID NO: 7:ATCAAAGAAA CTAGAATTGC CACCTCCTTA TGAGGAATCA AGTCCTATGG 101                                                  150
SEQ ID NO: 5:AGATTCAACC ATCTGCCCCA TTATCAAATG ACTTCTTCGG AATGGAGGAT
SEQ ID NO: 6:AGATTCAACC ATCTGCCCCA TTATCAAATG ACTTCTTCGG AAGGGAGGAT
SEQ ID NO: 7:AGATTCAACC ATCTGCCCCA TTATCAAATG ACTTCTTCGG AAGGGAGGAT 151                                                  200
SEQ ID NO: 5:ATGGATTTAT ATGATAAGGA CTCCTTGAGA TATGAGAAGT TCCGCTTTAT
SEQ ID NO: 6:AGGGATTTAT ATGATAAGGA CTCCTTGAGA TATGAGAAGT TCCGCTTTAT
SEQ ID NO: 7:AGGGATTTAT ATGATAAGGA CTCCTTGAGA TATGAGAAGT TCCGCTTTAT 201                                                  250
SEQ ID NO: 5:GTTGAAGATG ACTGTTAGAG CTAACAAGCC CTTCAGATCG TATGATGATG
SEQ ID NO: 6:GTTGAAGATG ACTGTTAGAG CTAACAAGCC CTTCAGATCG TATGATGATG
SEQ ID NO: 7:GTTGAAGATG ACTGTTAGAG CTAACAAGCC CTTCAGATCG TATGATGATG 251                                                  300
SEQ ID NO: 5:TCACCGCAGC GGTATCACAA TGGGATAATT CATACATTGG AATGGTTGGA
SEQ ID NO: 6:TCACCGCAGC GGTATCACAA TGGGATAATT CATACATTGG AATGGTTGGA
SEQ ID NO: 7:TCACCGCAGC GGTATCACAA TGGGATAATT CATACATTGG AATGGTTGGA 301                                                  350
SEQ ID NO: 5:AAGCGTCCTT TCTACAAGAT AATTGCTCTG ATTGGCTCCA GTCATCTGCA
SEQ ID NO: 6:AAGCGTCCTT TCTACAAGAT AATTGCTCTG ATTGGCTCCA GTCATCTGCA
SEQ ID NO: 7:AAGCGTCCTT TCTACAAGAT AATTGCTTTT ATTGGCTCCA GTCATCTGCA 351                                                  400
SEQ ID NO: 5:AGCAACTCCA GCTGTGTTGG CAGACTTAAA TCAACCAGAG TATTATGCCA
SEQ ID NO: 6:AGCAACTCCA GCTGTGTTGG CAGACTTAAA TCAACCAGAG TATTATGCCA
SEQ ID NO: 7:AGCAACTCCA GCTGTGTTGG CAGACTTAAA TCAACCAGAG TATTATGCCA 401                                                  450
SEQ ID NO: 5:CACTAACAGG TCGTTGTTTT CTTCCTCACC GACTCGGATT GATCCCACCG
SEQ ID NO: 6:CACTAACAGG TCGTTGTTTT CTTCCTCACC GACTCGGATT GATCCCACCG
SEQ ID NO: 7:CACTAACAGG TCGTTGTTTT CTTCCTCACC GACTCGGATT GATCCCACCG
```

TABLE 4-continued

Nucleotide Sequence Comparison between M Genes of VSV New Jersey
serotype Wild Type (SEQ ID NO: 5) and Mutants, G22E/M48R + M51R
(SEQ ID NO: 6) and G22E/L110F/M48R + M51R (SEQ ID NO: 7)

```
                451                                            500
SEQ ID NO: 5: ATGTTTAATG TGTCCGAAAC TTTCAGAAAA CCATTCAATA TTGGGATATA
SEQ ID NO: 6: ATGTTTAATG TGTCCGAAAC TTTCAGAAAA CCATTCAATA TTGGGATATA
SEQ ID NO: 7: ATGTTTAATG TGTCCGAAAC TTTCAGAAAA CCATTCAATA TTGGGATATA 501                                            550
SEQ ID NO: 5: CAAAGGGACT CTCGACTTCA CCTTTACAGT TTCAGATGAT GAGTCTAATG
SEQ ID NO: 6: CAAAGGGACT CTCGACTTCA CCTTTACAGT TTCAGATGAT GAGTCTAATG
SEQ ID NO: 7: CAAAGGGACT CTCGACTTCA CCTTTACAGT TTCAGATGAT GAGTCTAATG 551                                            600
SEQ ID NO: 5: AAAAGTCCC TCATGTTTGG AATACATGA ACCCAAAATA TCAATCTCAG
SEQ ID NO: 6: AAAAGTCCC TCATGTTTGG AATACATGA ACCCAAAATA TCAATCTCAG
SEQ ID NO: 7: AAAAGTCCC TCATGTTTGG AATACATGA ACCCAAAATA TCAATCTCAG 601                                            650
SEQ ID NO: 5: ATCCAAAAAG AAGGGCTTAA ATTCGGATTG ATTTTAAGCA AGAAAGCAAC
SEQ ID NO: 6: ATCCAAAAAG AAGGGCTTAA ATTCGGATTG ATTTTAAGCA AGAAAGCAAC
SEQ ID NO: 7: ATCCAAAAAG AAGGGCTTAA ATTCGGATTG ATTTTAAGCA AGAAAGCAAC 651                                            700
SEQ ID NO: 5: GGGAACTTGG GTGTTAGACC AATTGAGTCC GTTTAA
SEQ ID NO: 6: GGGAACTTGG GTGTTAGACC AATTGAGTCC GTTTAA
SEQ ID NO: 7: GGGAACTTGG GTGTTAGACC AATTGAGTCC GTTTAA
```

TABLE 5

Amino Acid Sequence Comparison between M Proteins of VSV New Jersey
serotype Wild Type (SEQ ID NO: 8) and Mutants, G22E/M48R + M51R
(SEQ ID NO: 9) and G22E/L110F/M48R + M51R (SEQ ID NO: 10)

```
                 1                  22                        48 50
SEQ ID NO:  8: MSSFKKILGF SSKSHKKSKK LGLPPPYEES SPMEIQPSAP LSNDFFGMED
SEQ ID NO:  9: MSSFKKILGF SSKSHKRSKK LELPPPYEES SPMEIQPSAP LSNDFFGRED
SEQ ID NO: 10: MSSFKKILGF SSKSHKKSKK LELPPPYEES SPMEIQPSAP LSNDFFGRED 51                                             100
SEQ ID NO:  8: MDLYDKDSLR YEKFRFMLKM TVRANKPFRS YDDVTAAVSQ WDNSYIGMVG
SEQ ID NO:  9: RDLYDKDSLR YEKFRFMLKM TVRANKPFRS YDDVTAAVSQ WDNSYIGMVG
SEQ ID NO: 10: RDLYDKDSLR YEKFRFMLKM TVRANKPFRS YDDVTAAVSQ WDNSYIGMVG 101      110                                   150
SEQ ID NO:  8: KRPFYKIIAL IGSSHLQATP AVLADLNQPE YYATLTGRCF LPHRLGLIPP
SEQ ID NO:  9: KRPFYKIIAL IGSSHLQATP AVLADLNQPE YYATLTGRCF LPHRLGLIPP
SEQ ID NO: 10: KRPFYKIIAF IGSSHLQATP AVLADLNQPE YYATLTGRCF LPHRLGLIPP 151                                            200
SEQ ID NO:  8: MFNVSETFRK PFNIGIYKGT LDFTFTVSDD ESNEKVPHVW EYMNPKYQSQ
SEQ ID NO:  9: MFNVSETFRK PFNIGIYKGT LDFTFTVSDD ESNEKVPHVW EYMNPKYQSQ
SEQ ID NO: 10: MFNVSETFRK PFNIGIYKGT LDFTFTVSDD ESNEKVPHVW EYMNPKYQSQ 201                       250
SEQ ID NO:  8: IQKEGLKFGL ILSKKATGTW VLDQLSPFK
SEQ ID NO:  9: IQKEGLKFGL ILSKKATGTW VLDQLSPFK
SEQ ID NO: 10: IQKEGLKFGL ILSKKATGTW VLDQLSPFK
```

TABLE 6

Vaccination studies in mice for broad range CD8+ T cell responses and humoral immune responses against HIV-1 proteins

| Vaccination Groups | rVSVw/HIV-1 Proteins | |
|---|---|---|
| | Prime | Boost |
| G1 | rVSV$_{Ind}$(GLM) | rVSV$_{NJ}$(GM) |
| G2 | rVSV$_{Ind}$(GLM)-HIV-1 Gag-En | rVSV$_{NJ}$(GM)-HIV-1 Gag-En |
| G3 | rVSV$_{Ind}$(GLM)-HIV-1 Gp160mss | rVSV$_{NJ}$(GM)-HIV-1 Gp160mss |

TABLE 6-continued

Vaccination studies in mice for broad range CD8+ T cell responses and humoral immune responses against HIV-1 proteins

| Vaccination Groups | rVSVw/HIV-1 Proteins | |
|---|---|---|
| | Prime | Boost |
| G4 | rVSV$_{Ind}$(GLM)-HIV-1 Pol | rVSV$_{NJ}$(GM)-HIV-1 Pol |
| G5 | rVSV$_{Ind}$(GLM)-HIV-1 Gag-En + rVSV$_{Ind}$(GLM)-Gp160mss + rVSV$_{Ind}$(GLM)-HIV-1 Pol | rVSV$_{NJ}$(GM)-HIV-1 Gag-En + rVSV$_{NJ}$(GM)-Gp160mss + rVSV$_{NJ}$(GM)-HIV1 Pol |
| G6 | rVSV$_{Ind}$(GLM)-HIV-1 Gag-A + rVSV$_{Ind}$(GLM)-HIV-1 Gag-B + rVSV$_{Ind}$(GLM)-HIV-1 Gag-C | rVSV$_{NJ}$(GM)-HIV-1 Gag-A + rVSV$_{NJ}$(GM)-HIV-1 Gag-B + rVSV$_{NJ}$(GM)-HIV-1 Gag-C |

We claim:

1. A recombinant vesicular stomatitis virus (rVSV), wherein said rVSV comprises a modified matrix (M) protein, the modified M protein comprising an amino acid sequence selected from the group consisting of: (i) SEQ ID NO: 3 including the following substitutions: G21E/L111F/M51R; and (ii) SEQ ID NO: 8 including the following substitutions: G22E/M48R/M51R.

2. The rVSV of claim 1, wherein the rVSV is a chimeric rVSV that expresses a protein of a foreign pathogen, and wherein said chimeric rVSV is capable of inducing an immune response to said protein.

3. The rVSV of claim 2, wherein said pathogen is a viral, fungal, bacterial or parasitic pathogen.

4. The rVSV of claim 1, wherein the rVSV is non-cytolytic and avirulent.

5. The rVSV of claim 1, wherein said rVSV is a recombinant vesicular stomatitis virus Indiana serotype (rVSV$_{Ind}$), and wherein the modified M protein comprises the amino acid sequence of SEQ ID NO: 3 including the following substitution: G21E/L111F/M51R.

6. The rVSV of claim 5, wherein the modified M protein comprises the amino acid sequence of SEQ ID NO: 4.

7. The rVSV of claim 5, wherein the modified M protein is encoded by a gene comprising a nucleotide sequence of SEQ ID NO: 2.

8. The rVSV of claim 5, wherein the rVSV$_{Ind}$ is capable of producing VSV$_{Ind}$ particles at permissible temperatures and incapable of producing the particles at non-permissible temperatures.

9. The rVSV of claim 1, wherein said rVSV is a recombinant vesicular stomatitis virus New Jersey serotype (rVSV$_{NJ}$), and wherein the modified M protein comprises the amino acid sequence of SEQ ID NO: 8 including the following substitutions: G22E/M48R/M51R.

10. The rVSV of claim 9, wherein the modified M protein is encoded by a gene having a nucleotide sequence of SEQ ID NO: 6.

11. The rVSV of claim 9, wherein the modified M protein comprises the amino acid sequence SEQ ID NO: 9.

12. The rVSV of claim 9, wherein the modified M protein further includes the following substitution: L110F.

13. The rVSV of claim 12, wherein the modified M protein is encoded by a gene having a nucleotide sequence of SEQ ID NO: 7.

14. The rVSV of claim 12, wherein the modified M protein comprises the amino acid sequence SEQ ID NO: 10.

* * * * *

SEQUENCE LISTING

<160> NUMBER OF SEQ ID NOS: 37

<210> SEQ ID NO 1
<211> LENGTH: 690
<212> TYPE: DNA
<213> ORGANISM: Artificial Sequence
<220> FEATURE:
<223> OTHER INFORMATION: Synthetic: Genes of VSV Indiana serotype, Wild Type

<400> SEQUENCE: 1

```
atgagttcct taaagaagat tctcggtctg aagggggaaag gtaagaaatc taagaaatta      60
gggatcgcac caccccctta tgaagaggac actaacatgg agtatgctcc gagcgctcca     120
attgacaaat cctattttgg agttgacgag atggacactc atgatccgca tcaattaaga     180
tatgagaaat tcttctttac agtgaaaatg acggttagat ctaatcgtcc gttcagaaca     240
tactcagatg tggcagccgc tgtatcccat tgggatcaca tgtacatcgg aatggcaggg     300
aaacgtccct tctacaagat cttggctttt ttgggttctt ctaatctaaa ggccactcca     360
gcggtattgg cagatcaagg tcaaccagag tatcacgctc actgtgaagg cagggcttat     420
ttgccacaca gaatggggaa gacccctccc atgctcaatg taccagagca cttcagaaga     480
ccattcaata taggtcttta caagggaacg gttgagctca caatgaccat ctacgatgat     540
gagtcactgg aagcagctcc tatgatctgg gatcatttca attcttccaa attttctgat     600
ttcagagata aggccttaat gtttggcctg attgtcgaga aaaaggcatc tggagcttgg     660
gtcctggatt ctgtcagcca cttcaaatga                                      690
```

<210> SEQ ID NO 2
<211> LENGTH: 690
<212> TYPE: DNA
<213> ORGANISM: Artificial Sequence
<220> FEATURE:
<223> OTHER INFORMATION: Synthetic: Mutant G21E/L111F/M51R

<400> SEQUENCE: 2

```
atgagttcct taaagaagat tctcggtctg aagggggaaag gtaagaaatc taagaaatta      60
gaaatcgcac caccccctta tgaagaggac actaacatgg agtatgctcc gagcgctcca     120
attgacaaat cctattttgg agttgacgag agggacactc atgatccgca tcaattaaga     180
tatgagaaat tcttctttac agtgaaaatg acggttagat ctaatcgtcc gttcagaaca     240
tactcagatg tggcagccgc tgtatcccat tgggatcaca tgtacatcgg aatggcaggg     300
aaacgtccct tctacaagat cttggctttt tttggttctt ctaatctaaa ggccactcca     360
gcggtattgg cagatcaagg tcaaccagag tatcacgctc actgtgaagg cagggcttat     420
```

```
ttgccacaca gaatggggaa gacccctccc atgctcaatg taccagagca cttcagaaga    480
ccattcaata taggtcttta caagggaacg gttgagctca caatgaccat ctacgatgat    540
gagtcactgg aagcagctcc tatgatctgg gatcatttca attcttccaa attttctgat    600
ttcagagata aggccttaat gtttggcctg attgtcgaga aaaaggcatc tggagcttgg    660
gtcctggatt ctgtcagcca cttcaaatga                                     690
```

<210> SEQ ID NO 3
<211> LENGTH: 229
<212> TYPE: PRT
<213> ORGANISM: Artificial Sequence
<220> FEATURE:
<223> OTHER INFORMATION: Synthetic: VSV Indiana serotype Wild Type

<400> SEQUENCE: 3

```
Met Ser Ser Leu Lys Lys Ile Leu Gly Leu Lys Gly Lys Gly Lys Lys
1               5                   10                  15

Ser Lys Lys Leu Gly Ile Ala Pro Pro Tyr Glu Glu Asp Thr Asn
            20                  25                  30

Met Glu Tyr Ala Pro Ser Ala Pro Ile Asp Lys Ser Tyr Phe Gly Val
        35                  40                  45

Asp Glu Met Asp Thr His Asp Pro His Gln Leu Arg Tyr Glu Lys Phe
    50                  55                  60

Phe Phe Thr Val Lys Met Thr Val Arg Ser Asn Arg Pro Phe Arg Thr
65                  70                  75                  80

Tyr Ser Asp Val Ala Ala Ala Val Ser His Trp Asp His Met Tyr Ile
                85                  90                  95

Gly Met Ala Gly Lys Arg Pro Phe Tyr Lys Ile Leu Ala Phe Leu Gly
            100                 105                 110

Ser Ser Asn Leu Lys Ala Thr Pro Ala Val Leu Ala Asp Gln Gly Gln
        115                 120                 125

Pro Glu Tyr His Ala His Cys Glu Gly Arg Ala Tyr Leu Pro His Arg
    130                 135                 140

Met Gly Lys Thr Pro Pro Met Leu Asn Val Pro Glu His Phe Arg Arg
145                 150                 155                 160

Pro Phe Asn Ile Gly Leu Tyr Lys Gly Thr Val Glu Leu Thr Met Thr
                165                 170                 175

Ile Tyr Asp Asp Glu Ser Leu Glu Ala Ala Pro Met Ile Trp Asp His
            180                 185                 190

Phe Asn Ser Ser Lys Phe Ser Asp Phe Arg Asp Lys Ala Leu Met Phe
        195                 200                 205

Gly Leu Ile Val Glu Lys Lys Ala Ser Gly Ala Trp Val Leu Asp Ser
    210                 215                 220

Val Ser His Phe Lys
225
```

<210> SEQ ID NO 4
<211> LENGTH: 229
<212> TYPE: PRT
<213> ORGANISM: Artificial Sequence
<220> FEATURE:
<223> OTHER INFORMATION: Synthetic: Mutant G21E/L111F/M51R

<400> SEQUENCE: 4

```
Met Ser Ser Leu Lys Lys Ile Leu Gly Leu Lys Gly Lys Gly Lys Lys
1               5                   10                  15

Ser Lys Lys Leu Glu Ile Ala Pro Pro Tyr Glu Glu Asp Thr Asn
            20                  25                  30
```

```
                  20                  25                  30
Met Glu Tyr Ala Pro Ser Ala Pro Ile Asp Lys Ser Tyr Phe Gly Val
             35                  40                  45

Asp Glu Arg Asp Thr His Asp Pro His Gln Leu Arg Tyr Glu Lys Phe
         50                  55                  60

Phe Phe Thr Val Lys Met Thr Val Arg Ser Asn Arg Pro Phe Arg Thr
65                  70                  75                  80

Tyr Ser Asp Val Ala Ala Val Ser His Trp Asp His Met Tyr Ile
                 85                  90                  95

Gly Met Ala Gly Lys Arg Pro Phe Tyr Lys Ile Leu Ala Phe Phe Gly
                100                 105                 110

Ser Ser Asn Leu Lys Ala Thr Pro Ala Val Leu Ala Asp Gln Gly Gln
            115                 120                 125

Pro Glu Tyr His Ala His Cys Glu Gly Arg Ala Tyr Leu Pro His Arg
        130                 135                 140

Met Gly Lys Thr Pro Pro Met Leu Asn Val Pro Glu His Phe Arg Arg
145                 150                 155                 160

Pro Phe Asn Ile Gly Leu Tyr Lys Gly Thr Val Glu Leu Thr Met Thr
                165                 170                 175

Ile Tyr Asp Asp Glu Ser Leu Glu Ala Ala Pro Met Ile Trp Asp His
            180                 185                 190

Phe Asn Ser Ser Lys Phe Ser Asp Phe Arg Asp Lys Ala Leu Met Phe
        195                 200                 205

Gly Leu Ile Val Glu Lys Lys Ala Ser Gly Ala Trp Val Leu Asp Ser
    210                 215                 220

Val Ser His Phe Lys
225

<210> SEQ ID NO 5
<211> LENGTH: 686
<212> TYPE: DNA
<213> ORGANISM: Artificial Sequence
<220> FEATURE:
<223> OTHER INFORMATION: Synthetic: VSV New Jersey serotype Wild Type

<400> SEQUENCE: 5
atgagttcct tcaaaaagat tctgggattt tcttcaaaaa gtcacaagaa atcaagaaa    60 ctaggcttgc cacctcctta tgaggaatca agtcctatgg agattcaacc atctgcccca   120
ttatcaaatg acttcttcgg aatggaggat atggatttat atgataagga ctccttgaga   180
tatgagaagt tccgctttat gttgaagatg actgttagag ctaacaagcc cttcagatcg   240
tatgatgatg tcaccgcagc ggtatcacaa tgggataatt catacattgg aatggttgga   300
aagcgtcctt tctacaagat aattgctctg attggctcca gtcatctgca agcaactcca   360
gctgtgttgg cagacttaaa tcaaccagag tattatgcca cactaacagg tcgttgtttt   420
cttcctcacc gactcggatt gatcccaccg atgtttaatg tgtccgaaac tttcagaaaa   480
ccattcaata ttgggatata caaagggact ctcgacttca cctttacagt ttcagatgat   540
gagtctaatg aaaaagtccc tcatgtttgg aatacatga acccaaaata tcaatctcag   600
atccaaaaag aagggcttaa attcggattg atttaagca agaaagcaac gggaacttgg   660
gtgttagacc aattgagtcc gtttaa                                        686

<210> SEQ ID NO 6
<211> LENGTH: 686
<212> TYPE: DNA
```

<210> SEQ ID NO 6 (continued)
<213> ORGANISM: Artificial Sequence
<220> FEATURE:
<223> OTHER INFORMATION: Synthetic: G22E/M48R+M51R

<400> SEQUENCE: 6

```
atgagttcct tcaaaaagat tctgggattt tcttcaaaaa gtcacaagaa atcaaagaaa        60
ctagaattgc cacctcctta tgaggaatca agtcctatgg agattcaacc atctgcccca       120
ttatcaaatg acttcttcgg aagggaggat agggatttat atgataagga ctccttgaga       180
tatgagaagt tccgctttat gttgaagatg actgttagag ctaacaagcc cttcagatcg       240
tatgatgatg tcaccgcagc ggtatcacaa tgggataatt catacattgg aatggttgga       300
aagcgtcctt tctacaagat aattgctctg attggctcca gtcatctgca agcaactcca       360
gctgtgttgg cagacttaaa tcaaccagag tattatgcca cactaacagg tcgttgtttt       420
cttcctcacc gactcggatt gatcccaccg atgtttaatg tgtccgaaac tttcagaaaa       480
ccattcaata ttgggatata caagggact ctcgacttca cctttacagt ttcagatgat       540
gagtctaatg aaaaagtccc tcatgtttgg gaatacatga acccaaaata tcaatctcag       600
atccaaaaag aagggcttaa attcggattg attttaagca agaaagcaac gggaacttgg       660
gtgttagacc aattgagtcc gttttaa                                           686
```

<210> SEQ ID NO 7
<211> LENGTH: 686
<212> TYPE: DNA
<213> ORGANISM: Artificial Sequence
<220> FEATURE:
<223> OTHER INFORMATION: Synthetic: G22E/L110F/M48R+M51R

<400> SEQUENCE: 7

```
atgagttcct tcaaaaagat tctgggattt tcttcaaaaa gtcacaagaa atcaaagaaa        60
ctagaattgc cacctcctta tgaggaatca agtcctatgg agattcaacc atctgcccca       120
ttatcaaatg acttcttcgg aagggaggat agggatttat atgataagga ctccttgaga       180
tatgagaagt tccgctttat gttgaagatg actgttagag ctaacaagcc cttcagatcg       240
tatgatgatg tcaccgcagc ggtatcacaa tgggataatt catacattgg aatggttgga       300
aagcgtcctt tctacaagat aattgctttt attggctcca gtcatctgca agcaactcca       360
gctgtgttgg cagacttaaa tcaaccagag tattatgcca cactaacagg tcgttgtttt       420
cttcctcacc gactcggatt gatcccaccg atgtttaatg tgtccgaaac tttcagaaaa       480
ccattcaata ttgggatata caagggact ctcgacttca cctttacagt ttcagatgat       540
gagtctaatg aaaaagtccc tcatgtttgg gaatacatga acccaaaata tcaatctcag       600
atccaaaaag aagggcttaa attcggattg attttaagca agaaagcaac gggaacttgg       660
gtgttagacc aattgagtcc gttttaa                                           686
```

<210> SEQ ID NO 8
<211> LENGTH: 229
<212> TYPE: PRT
<213> ORGANISM: Artificial Sequence
<220> FEATURE:
<223> OTHER INFORMATION: Synthetic: VSV New Jersey serotype Wild Type

<400> SEQUENCE: 8

Met Ser Ser Phe Lys Lys Ile Leu Gly Phe Ser Ser Lys Ser His Lys
1               5                   10                  15

Lys Ser Lys Lys Leu Gly Leu Pro Pro Pro Tyr Glu Glu Ser Ser Pro
            20                  25                  30

Met Glu Ile Gln Pro Ser Ala Pro Leu Ser Asn Asp Phe Phe Gly Met
            35                  40                  45

Glu Asp Met Asp Leu Tyr Asp Lys Asp Ser Leu Arg Tyr Glu Lys Phe
 50                  55                  60

Arg Phe Met Leu Lys Met Thr Val Arg Ala Asn Lys Pro Phe Arg Ser
 65                  70                  75                  80

Tyr Asp Asp Val Thr Ala Ala Val Ser Gln Trp Asp Asn Ser Tyr Ile
                 85                  90                  95

Gly Met Val Gly Lys Arg Pro Phe Tyr Lys Ile Ile Ala Leu Ile Gly
                100                 105                 110

Ser Ser His Leu Gln Ala Thr Pro Ala Val Leu Ala Asp Leu Asn Gln
                115                 120                 125

Pro Glu Tyr Tyr Ala Thr Leu Thr Gly Arg Cys Phe Leu Pro His Arg
            130                 135                 140

Leu Gly Leu Ile Pro Pro Met Phe Asn Val Ser Glu Thr Phe Arg Lys
145                 150                 155                 160

Pro Phe Asn Ile Gly Ile Tyr Lys Gly Thr Leu Asp Phe Thr Phe Thr
                    165                 170                 175

Val Ser Asp Asp Glu Ser Asn Glu Lys Val Pro His Val Trp Glu Tyr
                180                 185                 190

Met Asn Pro Lys Tyr Gln Ser Gln Ile Gln Lys Glu Gly Leu Lys Phe
            195                 200                 205

Gly Leu Ile Leu Ser Lys Ala Thr Gly Thr Trp Val Leu Asp Gln
210                 215                 220

Leu Ser Pro Phe Lys
225

<210> SEQ ID NO 9
<211> LENGTH: 229
<212> TYPE: PRT
<213> ORGANISM: Artificial Sequence
<220> FEATURE:
<223> OTHER INFORMATION: Synthetic: G22E/M48R+M51R

<400> SEQUENCE: 9

Met Ser Ser Phe Lys Lys Ile Leu Gly Phe Ser Ser Lys Ser His Lys
 1               5                   10                  15

Lys Ser Lys Lys Leu Glu Leu Pro Pro Tyr Glu Gly Ser Ser Pro
                20                  25                  30

Met Glu Ile Gln Pro Ser Ala Pro Leu Ser Asn Asp Phe Phe Gly Arg
            35                  40                  45

Glu Asp Arg Asp Leu Tyr Asp Lys Asp Ser Leu Arg Tyr Glu Lys Phe
 50                  55                  60

Arg Phe Met Leu Lys Met Thr Val Arg Ala Asn Lys Pro Phe Arg Ser
 65                  70                  75                  80

Tyr Asp Asp Val Thr Ala Ala Val Ser Gln Trp Asp Asn Ser Tyr Ile
                 85                  90                  95

Gly Met Val Gly Lys Arg Pro Phe Tyr Lys Ile Ile Ala Leu Ile Gly
                100                 105                 110

Ser Ser His Leu Gln Ala Thr Pro Ala Val Leu Ala Asp Leu Asn Gln
                115                 120                 125

Pro Glu Tyr Tyr Ala Thr Leu Thr Gly Arg Cys Phe Leu Pro His Arg
            130                 135                 140

Leu Gly Leu Ile Pro Pro Met Phe Asn Val Ser Glu Thr Phe Arg Lys
145                 150                 155                 160

-continued

Pro Phe Asn Ile Gly Ile Tyr Lys Gly Thr Leu Asp Phe Thr Phe Thr
                165                 170                 175

Val Ser Asp Asp Glu Ser Asn Glu Lys Val Pro His Val Trp Glu Tyr
            180                 185                 190

Met Asn Pro Lys Tyr Gln Ser Gln Ile Gln Lys Glu Gly Leu Lys Phe
        195                 200                 205

Gly Leu Ile Leu Ser Lys Lys Ala Thr Gly Thr Trp Val Leu Asp Gln
    210                 215                 220

Leu Ser Pro Phe Lys
225

<210> SEQ ID NO 10
<211> LENGTH: 229
<212> TYPE: PRT
<213> ORGANISM: Artificial Sequence
<220> FEATURE:
<223> OTHER INFORMATION: Synthetic: G22E/L110F/M48R+M51R

<400> SEQUENCE: 10

Met Ser Ser Phe Lys Lys Ile Leu Gly Phe Ser Ser Lys Ser His Lys
1               5                   10                  15

Lys Ser Lys Lys Leu Glu Leu Pro Pro Tyr Glu Glu Ser Ser Pro
            20                  25                  30

Met Glu Ile Gln Pro Ser Ala Pro Leu Ser Asn Asp Phe Phe Gly Arg
        35                  40                  45

Glu Asp Arg Asp Leu Tyr Asp Lys Asp Ser Leu Arg Tyr Glu Lys Phe
    50                  55                  60

Arg Phe Met Leu Lys Met Thr Val Arg Ala Asn Lys Pro Phe Arg Ser
65                  70                  75                  80

Tyr Asp Asp Val Thr Ala Ala Val Ser Gln Trp Asp Asn Ser Tyr Ile
                85                  90                  95

Gly Met Val Gly Lys Arg Pro Phe Tyr Lys Ile Ile Ala Phe Ile Gly
            100                 105                 110

Ser Ser His Leu Gln Ala Thr Pro Ala Val Leu Ala Asp Leu Asn Gln
        115                 120                 125

Pro Glu Tyr Tyr Ala Thr Leu Thr Gly Arg Cys Phe Leu Pro His Arg
    130                 135                 140

Leu Gly Leu Ile Pro Pro Met Phe Asn Val Ser Glu Thr Phe Arg Lys
145                 150                 155                 160

Pro Phe Asn Ile Gly Ile Tyr Lys Gly Thr Leu Asp Phe Thr Phe Thr
                165                 170                 175

Val Ser Asp Asp Glu Ser Asn Glu Lys Val Pro His Val Trp Glu Tyr
            180                 185                 190

Met Asn Pro Lys Tyr Gln Ser Gln Ile Gln Lys Glu Gly Leu Lys Phe
        195                 200                 205

Gly Leu Ile Leu Ser Lys Lys Ala Thr Gly Thr Trp Val Leu Asp Gln
    210                 215                 220

Leu Ser Pro Phe Lys
225

<210> SEQ ID NO 11
<211> LENGTH: 9
<212> TYPE: PRT
<213> ORGANISM: Artificial Sequence
<220> FEATURE:
<223> OTHER INFORMATION: Synthetic: gp41 HXB2(337-345)

<400> SEQUENCE: 11

Ile Pro Arg Arg Ile Arg Gln Gly Leu
1               5

<210> SEQ ID NO 12
<211> LENGTH: 9
<212> TYPE: PRT
<213> ORGANISM: Artificial Sequence
<220> FEATURE:
<223> OTHER INFORMATION: Synthetic: Nef HXB2(92-100)

<400> SEQUENCE: 12

Lys Glu Lys Gly Gly Leu Asp Gly Leu
1               5

<210> SEQ ID NO 13
<211> LENGTH: 10
<212> TYPE: PRT
<213> ORGANISM: Artificial Sequence
<220> FEATURE:
<223> OTHER INFORMATION: Synthetic: Nef HXB2(128-137)

<400> SEQUENCE: 13

Thr Pro Gly Pro Gly Val Arg Tyr Pro Leu
1               5                   10

<210> SEQ ID NO 14
<211> LENGTH: 10
<212> TYPE: PRT
<213> ORGANISM: Artificial Sequence
<220> FEATURE:
<223> OTHER INFORMATION: Synthetic: gp120 HXB2(584-592)

<400> SEQUENCE: 14

Glu Arg Tyr Leu Lys Asp Gln Gln Leu Leu
1               5                   10

<210> SEQ ID NO 15
<211> LENGTH: 17
<212> TYPE: PRT
<213> ORGANISM: Artificial Sequence
<220> FEATURE:
<223> OTHER INFORMATION: Synthetic: gp120 HXB2(30-46)

<400> SEQUENCE: 15

Ala Ala Glu Asn Leu Trp Val Thr Val Tyr Tyr Gly Val Pro Val Trp
1               5                   10                  15

Lys

<210> SEQ ID NO 16
<211> LENGTH: 15
<212> TYPE: PRT
<213> ORGANISM: Artificial Sequence
<220> FEATURE:
<223> OTHER INFORMATION: Synthetic: Clade B gp120 V3 loop

<400> SEQUENCE: 16

Ser Ile Pro Ile Gly Pro Gly Arg Ala Phe Tyr Ala Thr Gly Asp
1               5                   10                  15

<210> SEQ ID NO 17
<211> LENGTH: 15
<212> TYPE: PRT
<213> ORGANISM: Artificial Sequence
<220> FEATURE:
<223> OTHER INFORMATION: Synthetic: Clade C gp120 V3 loop

<400> SEQUENCE: 17

Ser Val Arg Ile Gly Pro Gly Gln Thr Phe Tyr Ala Thr Gly Ala
1               5                   10                  15

<210> SEQ ID NO 18
<211> LENGTH: 15
<212> TYPE: PRT
<213> ORGANISM: Artificial Sequence
<220> FEATURE:
<223> OTHER INFORMATION: Synthetic: Clade E gp120 V3 loop

<400> SEQUENCE: 18

Ser Ile Arg Ile Gly Pro Gly Gln Val Phe Tyr Arg Thr Gly Asp
1               5                   10                  15

<210> SEQ ID NO 19
<211> LENGTH: 15
<212> TYPE: PRT
<213> ORGANISM: Artificial Sequence
<220> FEATURE:
<223> OTHER INFORMATION: Synthetic: Clade A gp120 V3 loop

<400> SEQUENCE: 19

Ser Val Arg Ile Gly Pro Gly Gln Thr Phe Tyr Ala Thr Gly Asp
1               5                   10                  15

<210> SEQ ID NO 20
<211> LENGTH: 15
<212> TYPE: PRT
<213> ORGANISM: Artificial Sequence
<220> FEATURE:
<223> OTHER INFORMATION: Synthetic: Clade D gp120 V3 loop

<400> SEQUENCE: 20

Arg Thr Pro Ile Gly Leu Gly Gln Ala Leu Tyr Thr Thr Arg Asp
1               5                   10                  15

<210> SEQ ID NO 21
<211> LENGTH: 15
<212> TYPE: PRT
<213> ORGANISM: Artificial Sequence
<220> FEATURE:
<223> OTHER INFORMATION: Synthetic: Clade F gp120 V3 loop

<400> SEQUENCE: 21

Arg Ile Ser Leu Gly Pro Gly Arg Val Phe Tyr Thr Ala Gly Glu
1               5                   10                  15

<210> SEQ ID NO 22
<211> LENGTH: 15
<212> TYPE: PRT
<213> ORGANISM: Artificial Sequence
<220> FEATURE:
<223> OTHER INFORMATION: Synthetic: Clade G gp120 V3 loop

<400> SEQUENCE: 22

Ser Ile Asn Leu Gly Pro Gly Gln Ala Ile Tyr Ala Thr Gly Ala
1               5                   10                  15

<210> SEQ ID NO 23
<211> LENGTH: 41
<212> TYPE: PRT
<213> ORGANISM: Artificial Sequence
<220> FEATURE:
<223> OTHER INFORMATION: Synthetic: Clade B gp120 C3 region

```
<400> SEQUENCE: 23

Pro Cys Arg Ile Lys Gln Ile Val Asn Met Trp Gln Glu Val Gly Lys
1               5                   10                  15

Ala Met Tyr Ala Pro Pro Ile Ser Gly Gln Ile Arg Cys Ser Ser Asn
            20                  25                  30

Ile Thr Gly Leu Leu Thr Arg Asp
        35                  40

<210> SEQ ID NO 24
<211> LENGTH: 20
<212> TYPE: PRT
<213> ORGANISM: Artificial Sequence
<220> FEATURE:
<223> OTHER INFORMATION: Synthetic: Clade C gp120 C3 region

<400> SEQUENCE: 24

Arg Ala Met Tyr Ala Pro Pro Ile Ala Gly Asn Ile Thr Cys Lys Ser
1               5                   10                  15

Asn Ile Arg Ser
            20

<210> SEQ ID NO 25
<211> LENGTH: 13
<212> TYPE: PRT
<213> ORGANISM: Artificial Sequence
<220> FEATURE:
<223> OTHER INFORMATION: Synthetic: Clade E gp120 C3 region

<400> SEQUENCE: 25

Gln Ala Asn Tyr Ala Pro Pro Ile Ser Gly Lys Ile Asn
1               5                   10

<210> SEQ ID NO 26
<211> LENGTH: 6
<212> TYPE: PRT
<213> ORGANISM: Artificial Sequence
<220> FEATURE:
<223> OTHER INFORMATION: Synthetic: Multi      gp 41CNE

<400> SEQUENCE: 26

Glu Leu Asp Lys Trp Ala
1               5

<210> SEQ ID NO 27
<211> LENGTH: 9
<212> TYPE: PRT
<213> ORGANISM: Artificial Sequence
<220> FEATURE:
<223> OTHER INFORMATION: Synthetic: RT HXB2(309-317)

<400> SEQUENCE: 27

Ile Leu Lys Glu Pro Val His Gly Val
1               5

<210> SEQ ID NO 28
<211> LENGTH: 20
<212> TYPE: PRT
<213> ORGANISM: Artificial Sequence
<220> FEATURE:
<223> OTHER INFORMATION: Synthetic: RT HXB2(171-190)

<400> SEQUENCE: 28

Phe Arg Lys Gln Asn Pro Asp Ile Val Ile Tyr Gln Tyr Met Asp Asp
1               5                   10                  15
```

```
Leu Tyr Val Gly
            20

<210> SEQ ID NO 29
<211> LENGTH: 9
<212> TYPE: PRT
<213> ORGANISM: Artificial Sequence
<220> FEATURE:
<223> OTHER INFORMATION: Synthetic: RT HXB2(156-166)

<400> SEQUENCE: 29

Ala Ile Phe Gln Ser Ser Met Thr Lys
1               5

<210> SEQ ID NO 30
<211> LENGTH: 10
<212> TYPE: PRT
<213> ORGANISM: Artificial Sequence
<220> FEATURE:
<223> OTHER INFORMATION: Synthetic: Tat HXB2(2-11)

<400> SEQUENCE: 30

Glu Pro Val Asp Pro Arg Leu Glu Pro Trp
1               5                   10

<210> SEQ ID NO 31
<211> LENGTH: 9
<212> TYPE: PRT
<213> ORGANISM: Artificial Sequence
<220> FEATURE:
<223> OTHER INFORMATION: Synthetic: Rev HXB2(69-77)

<400> SEQUENCE: 31

Pro Ala Glu Pro Val Pro Leu Gln Leu
1               5

<210> SEQ ID NO 32
<211> LENGTH: 9
<212> TYPE: PRT
<213> ORGANISM: Artificial Sequence
<220> FEATURE:
<223> OTHER INFORMATION: Synthetic: VSV N275 (275-283)

<400> SEQUENCE: 32

Met Pro Tyr Leu Ile Asp Phe Gly Leu
1               5

<210> SEQ ID NO 33
<211> LENGTH: 9
<212> TYPE: PRT
<213> ORGANISM: Artificial Sequence
<220> FEATURE:
<223> OTHER INFORMATION: Synthetic: Gag

<400> SEQUENCE: 33

Ala Met Gln Met Leu Lys Glu Thr Ile
1               5

<210> SEQ ID NO 34
<211> LENGTH: 15
<212> TYPE: PRT
<213> ORGANISM: Artificial Sequence
<220> FEATURE:
<223> OTHER INFORMATION: Synthetic: Env P18-R15K (315-329)

<400> SEQUENCE: 34

Arg Ile Gln Arg Gly Pro Gly Arg Ala Phe Val Thr Ile Gly Lys
```

```
<210> SEQ ID NO 35
<211> LENGTH: 20
<212> TYPE: PRT
<213> ORGANISM: Artificial Sequence
<220> FEATURE:
<223> OTHER INFORMATION: Synthetic: RT354 (354-373)

<400> SEQUENCE: 35

Arg Thr Lys Ile Glu Glu Leu Arg Gln His Leu Leu Arg Trp Gly Leu
1               5                   10                  15

Thr Thr Pro Asp
            20

<210> SEQ ID NO 36
<211> LENGTH: 20
<212> TYPE: PRT
<213> ORGANISM: Artificial Sequence
<220> FEATURE:
<223> OTHER INFORMATION: Synthetic: RT364 (464-483)

<400> SEQUENCE: 36

Ile Leu Lys Glu Pro Val His Gly Val Tyr Tyr Asp Pro Ser Lys Asp
1               5                   10                  15

Leu Ile Ala Glu
            20

<210> SEQ ID NO 37
<211> LENGTH: 11
<212> TYPE: PRT
<213> ORGANISM: Artificial Sequence
<220> FEATURE:
<223> OTHER INFORMATION: Synthetic: RT472 (472-482)

<400> SEQUENCE: 37

Val Tyr Tyr Asp Pro Ser Lys Asp Leu Ile Ala
1               5                   10
```